(12) United States Patent
Young

(10) Patent No.: US 7,933,722 B2
(45) Date of Patent: Apr. 26, 2011

(54) METHODS OF ANALYSIS OF POLYMORPHISMS AND USES THEREOF

(75) Inventor: Robert Peter Young, Auckland (NZ)

(73) Assignee: Synergenz Bioscience Limited, Hong Kong (CN)

( * ) Notice: Subject to any disclaimer, the term of this patent is extended or adjusted under 35 U.S.C. 154(b) by 1161 days.

(21) Appl. No.: 11/432,770

(22) Filed: May 10, 2006

(65) Prior Publication Data

US 2006/0275808 A1     Dec. 7, 2006

(30) Foreign Application Priority Data

May 20, 2005  (NZ) .................................... 540249
Aug. 15, 2005 (NZ) .................................... 541842

(51) Int. Cl.
*G06F 7/00* (2006.01)
(52) U.S. Cl. ................ 702/19; 702/20; 703/11; 703/12; 707/700; 435/6; 536/24.5
(58) Field of Classification Search ........................ None
See application file for complete search history.

(56) References Cited

U.S. PATENT DOCUMENTS

| | | | |
|---|---|---|---|
| 4,829,052 A | 5/1989 | Glover et al. |
| 5,455,262 A | 10/1995 | Schwartz et al. |
| 5,674,754 A | 10/1997 | Ahrens et al. |
| 5,773,430 A | 6/1998 | Simon et al. |
| 5,827,662 A | 10/1998 | Rubin |
| 5,837,492 A | 11/1998 | Tavtigian |
| 5,840,698 A | 11/1998 | Campbell et al. |
| 5,844,108 A | 12/1998 | Meyer |
| 5,851,983 A | 12/1998 | Sugiyama et al. |
| 5,932,579 A | 8/1999 | Campbell et al. |
| 5,935,852 A | 8/1999 | Follettie |
| 6,022,893 A | 2/2000 | Sakaki et al. |
| 6,033,857 A | 3/2000 | Tavtigian |
| 6,057,292 A | 5/2000 | Cunningham et al. |
| 6,057,297 A | 5/2000 | Politi et al. |
| 6,060,283 A | 5/2000 | Okura |
| 6,117,869 A | 9/2000 | Picard et al. |
| 6,171,798 B1 | 1/2001 | Levine |
| 6,183,963 B1 | 2/2001 | Sinnett |
| 6,184,022 B1 | 2/2001 | Seiki et al. |
| 6,187,587 B1 | 2/2001 | Popoff et al. |
| 6,211,209 B1 | 4/2001 | Baragi et al. |
| 6,268,142 B1 | 7/2001 | Duff |
| 6,346,385 B1 | 2/2002 | Eguchi et al. |
| 6,387,615 B2 | 5/2002 | Cookson et al. |
| 6,610,510 B1 | 8/2003 | Valenzuela |
| 6,673,549 B1 | 1/2004 | Furness |
| 6,677,442 B1 | 1/2004 | Wang |
| 6,706,478 B2 | 3/2004 | Duff |
| 6,716,581 B2 | 4/2004 | Lenz |
| 7,054,758 B2 | 5/2006 | Gill-Garrison et al. |
| 2002/0197646 A1 | 12/2002 | Nogee et al. |
| 2004/0106120 A1 | 6/2004 | Tazi-Ahnini et al. |
| 2004/0152124 A1 | 8/2004 | Duff |
| 2004/0219548 A1 | 11/2004 | Young |
| 2004/0241714 A1 | 12/2004 | Branch |
| 2005/0064454 A1 | 3/2005 | Young |
| 2005/0196754 A1 | 9/2005 | Drmanac |
| 2005/0272054 A1 | 12/2005 | Cargill |
| 2005/0282198 A1 | 12/2005 | Duff |
| 2006/0122373 A1 | 6/2006 | Mccarthy |

FOREIGN PATENT DOCUMENTS

| | | |
|---|---|---|
| EP | 0 854 191 A2 | 7/1998 |
| EP | 1 043 406 B1 | 6/2006 |
| JP | 2005328707 | 12/2005 |
| WO | WO 02/097127 | 12/2002 |
| WO | WO 2006121351 | 11/2006 |
| WO | WO 2006123943 | 11/2006 |
| WO | WO 2006123954 | 11/2006 |
| WO | WO 2006123955 | 11/2006 |

OTHER PUBLICATIONS

Barnes, "Molecular genetics of chronic obstructive pulmonary disease," *Thorax* 54:245-252 (1999).
Butkiewicz et al., "TSTM1, TSTP1, CYP1A1 and CYP2D6 polymorphisms in lung cancer patients from an environmentally polluted region of Poland: correlation with lung DNA adduct levels," *European Journal of Cancer Prevention*, (abstract) 8:315-323 (1999).
Cambien et al., "Polymorphisms of the Transforming Growth Factor-β1 Gene in Relation to Myocardial Infarction and Blood Pressure," *Hypertension* 28:881-887 (1996).
Cantlay et al., "Heterogeneous express and polymorphic genotype of glutathione S-transferase in human lung," *Thorax* 49:1010-1014 (1994).
Dunleavey et al., "Rapid genotype analysis of the matrix metalloproteinase-1 gene 1G/2G polymorphism that is associated with risk of cancer," *Matrix Biology*, 19:175-177 (2000).
Folz et al., "Elevated Levels of Extracellular Superoxide Dismutase in Chronic Lung Disease and Characterization of Genetic Variants," *Chest*, 111:74S (1997).
Greisenbach et al., "Anti-inflammatory gene therapy directed at the airway epithelium," *Gene Therapy*, vol. 7, No. 4, pp. 306-313 (Feb. 2000).
Harrison et al., "Frequency of glutathione S-transferase M1 deletion in smokers with emphysema and lung cancer," *Human & Experimental Toxicology* 16:356-360 (1997).
Hirano et al., "Tissue inhibitor of metalloproteinase-2 gene polymorphisms in chronic obstructive pulmonary disease," *European Respiratory Journal*, vol. 18, pp. 748-752 (2001).
Joos et al., "The role of matrix metalloproteinase polymorphisms in the rate of decline in lung function," *Human Molecular Genetics*, vol. 11, pp. 569-576 (2002).
Jormsjö et al., "Allele-Specific Regulation of Matrix Metlaloproteinase-12 Gene Activity is Associated with Coronary Artery Luminal Dimensions in Diabetic Patients with Manifest Coronary Artery Disease," *Cir. Res.* 86:998-1003 (2000).

(Continued)

*Primary Examiner* — Mark K Zeman

(74) *Attorney, Agent, or Firm* — Davis Wright Tremaine LLP

(57) ABSTRACT

The present invention provides methods for the assessment of diseases that result from the combined or interactive effects of two or more genetic variants, and in particular for diagnosing risk of developing such diseases in subjects using an analysis of genetic polymorphisms. Methods for the derivation of a net score indicative of a subject's risk of developing a disease are provided.

33 Claims, 3 Drawing Sheets

OTHER PUBLICATIONS

Kalsheker et al., "Deoxyribonucleic acid (DNA) polymorphism of the $a_1$-antitrypsin gene in chronic lung disease," *British Medical Journal*, 294:1511-1514 (1987).

Marklund et al., "Two variants of extracellular-superoxide dismutase: relationship to cardiovascular risk factors in an unselected middle-aged population," *Journal of Internal Medicine*, 242:5-14 (1997).

Minematsu et al. "Genetic polymorphism in Matrix Metalloproteinase-9 and pulmonary emphysema," *Biochemical and Biophysical Research Communication* vol. 289, pp. 116-119 (Nov. 2001).

Poller et al., "DNA polymorphisms of the $a_1$-antitrypsin gene region in patients with chronic obstructive pulmonary disease," *European Journal of Clinical Investigation*, 20:1-7 (1990).

Rinehart et al., "Human Alpha(1)-Proteinase Inhibitor Binds to Extracellular-Matrix In-Vitro," *American Journal of Respiratory Cell and Molecular Biology*, vol. 9, No. 6, pp. 666-679 (Dec. 1993).

Sandford et al, "Mutation in the 3' region of the α-1 antitrypsin gene and chronic obstructive pulmonary disease," *J. Med. Genet.*, 34:874-875 (1997).

Sandford et al., "Genetic risk factors for chronic obstructive pulmonary disease," *Eur. Respir. J.*, 10:1380-1391 (1997).

Shapiro, "Diverse Roles of Macrophage Matrix Metalloproteinases in Tissue Destruction and Tumor Growth," *Thromb Haemost.*, 82:846-849 (1999).

Sorsa et al., "Doxycycline in the Protection of Serum Alpha-1-Antitrypsin from Human Neutrophil Collagenase and Gelatinase," *Antimicrobial Agents and Chemotherapy*, vol. 37, No. 3, pp. 592-594 (1993).

Syrris et al., "Transforming growth factor-β1 gene polymorphisms and coronary artery disease," *Clinical Science*, 95:659-667 (1998).

Walter et al., "Environmental and genetic risk factors and gene-environment interactions in the pathogenesis of chronic lung disease," *Environmental Health Perspectives*, vol. 108, Suppl. 4, pp. 733-742 (2000).

Ye, S., *Matrix Biology* vol. 19, pp. 623-629 (2000).

Yim et al., "Genetic susceptibility to chronic obstructive pulmonary disease in Koreans: combined analysis of polymorphic genotypes for microsomal epoxide hydrolase and glutathione S-transferase M1 and T1," *Thorax*, 55:121-125 (2000).

Zhang et al., "Genetic variation at the matrix metalloproteinase-9 locus on chromosome 20q12.2-13.1," *Hum. Genet.*, 105:418-423 (1999).

Zhang et al., "Functional polymorphism in the regulatory region of gelatinase B gene in relation to severity of coronary artherosclerosis," *Circulation*, vol. 99, pp. 1788-1794 (1999).

U.S. Appl. No. 11/432,736, filed May 10, 2006, Young.
U.S. Appl. No. 11/432,770, filed May 2006.
U.S. Appl. No. 11/438,082, filed May 19, 2006, Young.
U.S. Appl. No. 11/437,823, filed May 19, 2006, Young.

SEQUENCE LISTING

<160> NUMBER OF SEQ ID NOS: 336

<210> SEQ ID NO 1
<211> LENGTH: 30
<212> TYPE: DNA
<213> ORGANISM: Artificial Sequence

```
<220> FEATURE:
<223> OTHER INFORMATION: Synthetic nucleic acid sequence

<400> SEQUENCE: 1
acgttggatg gcttgttaac cagctttgcc                                          30

<210> SEQ ID NO 2
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 2
acgttggatg ttttcagac tggcagagcg                                           30

<210> SEQ ID NO 3
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 3
acgttggatg ttttcagac tggcagagcg                                           30

<210> SEQ ID NO 4
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 4
acgttggatg gcttgttaac cagctttgcc                                          30

<210> SEQ ID NO 5
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 5
acgttggatg catgtcgcct tttcctgctc                                          30

<210> SEQ ID NO 6
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 6
acgttggatg caacacccaa caggcaaatg                                          30

<210> SEQ ID NO 7
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 7
acgttggatg tggtggacat ggtgaatgac                                          30
```

```
<210> SEQ ID NO 8
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 8
acgttggatg tggtgcagat gctcacatag                                          30

<210> SEQ ID NO 9
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 9
acgttggatg cacagagaga gtctggacac                                          30

<210> SEQ ID NO 10
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 10
acgttggatg ctcttggtct ttccctcatc                                          30

<210> SEQ ID NO 11
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 11
acgttggatg acagctctgc attcagcacg                                          30

<210> SEQ ID NO 12
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 12
acgttggatg agtcaatccc tttggtgctc                                          30

<210> SEQ ID NO 13
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 13
acgttggatg gttttccagc ttgcatgtcc                                          30

<210> SEQ ID NO 14
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 14
```

```
acgttggatg caatagtcag gtcctgtctc                                    30

<210> SEQ ID NO 15
<211> LENGTH: 29
<212> TYPE: DNA
<213> ORGANISM: Artificial Sequence
<220> FEATURE:
<223> OTHER INFORMATION: Synthetic nucleic acid sequence

<400> SEQUENCE: 15
acgttggatg gaacggcagc gccttcttg                                     29

<210> SEQ ID NO 16
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 16
acgttggatg acttggcaat ggctgtgatg                                    30

<210> SEQ ID NO 17
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 17
acgttggatg cagacattca caattgattt                                    30

<210> SEQ ID NO 18
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 18
acgttggatg gatagttcca aacatgtgcg                                    30

<210> SEQ ID NO 19
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 19
acgttggatg gggtattcat aagctgaaac                                    30

<210> SEQ ID NO 20
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 20
acgttggatg ccttcaagtt cagtggtcag                                    30

<210> SEQ ID NO 21
<211> LENGTH: 30
<212> TYPE: DNA
<213> ORGANISM: Artificial Sequence
```

```
<220> FEATURE:
<223> OTHER INFORMATION: Synthetic nucleic acid sequence

<400> SEQUENCE: 21
acgttggatg ggtcaatgaa gagaacttgg                                    30

<210> SEQ ID NO 22
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 22
acgttggatg aatgtttatt gtagaaaacc                                    30

<210> SEQ ID NO 23
<211> LENGTH: 15
<212> TYPE: DNA
<213> ORGANISM: Artificial Sequence
<220> FEATURE:
<223> OTHER INFORMATION: Synthetic nucleic acid sequence

<400> SEQUENCE: 23
agctttgcca gttcc                                                    15

<210> SEQ ID NO 24
<211> LENGTH: 18
<212> TYPE: DNA
<213> ORGANISM: Artificial Sequence
<220> FEATURE:
<223> OTHER INFORMATION: Synthetic nucleic acid sequence

<400> SEQUENCE: 24
aaaagcaaaa ttgcctga                                                 18

<210> SEQ ID NO 25
<211> LENGTH: 15
<212> TYPE: DNA
<213> ORGANISM: Artificial Sequence
<220> FEATURE:
<223> OTHER INFORMATION: Synthetic nucleic acid sequence

<400> SEQUENCE: 25
tcctgctctt ccctc                                                    15

<210> SEQ ID NO 26
<211> LENGTH: 17
<212> TYPE: DNA
<213> ORGANISM: Artificial Sequence
<220> FEATURE:
<223> OTHER INFORMATION: Synthetic nucleic acid sequence

<400> SEQUENCE: 26
acctccgctg caaatac                                                  17

<210> SEQ ID NO 27
<211> LENGTH: 18
<212> TYPE: DNA
<213> ORGANISM: Artificial Sequence
<220> FEATURE:
<223> OTHER INFORMATION: Synthetic nucleic acid sequence

<400> SEQUENCE: 27
gagtctggac acgtgggg                                                 18
```

```
<210> SEQ ID NO 28
<211> LENGTH: 19
<212> TYPE: DNA
<213> ORGANISM: Artificial Sequence
<220> FEATURE:
<223> OTHER INFORMATION: Synthetic nucleic acid sequence

<400> SEQUENCE: 28
tgctgcaggc cccagatga                                                    19

<210> SEQ ID NO 29
<211> LENGTH: 21
<212> TYPE: DNA
<213> ORGANISM: Artificial Sequence
<220> FEATURE:
<223> OTHER INFORMATION: Synthetic nucleic acid sequence

<400> SEQUENCE: 29
agaaactttt tcgcgaggga c                                                 21

<210> SEQ ID NO 30
<211> LENGTH: 24
<212> TYPE: DNA
<213> ORGANISM: Artificial Sequence
<220> FEATURE:
<223> OTHER INFORMATION: Synthetic nucleic acid sequence

<400> SEQUENCE: 30
agcgccttct tgctggcacc caat                                              24

<210> SEQ ID NO 31
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 31
tcttacaaca caaaatcaaa tc                                                22

<210> SEQ ID NO 32
<211> LENGTH: 15
<212> TYPE: DNA
<213> ORGANISM: Artificial Sequence
<220> FEATURE:
<223> OTHER INFORMATION: Synthetic nucleic acid sequence

<400> SEQUENCE: 32
agctgaaact tctgg                                                        15

<210> SEQ ID NO 33
<211> LENGTH: 20
<212> TYPE: DNA
<213> ORGANISM: Artificial Sequence
<220> FEATURE:
<223> OTHER INFORMATION: Synthetic nucleic acid sequence

<400> SEQUENCE: 33
tcaagcttgc caaagtaatc                                                   20

<210> SEQ ID NO 34
<211> LENGTH: 16
<212> TYPE: DNA
<213> ORGANISM: Artificial Sequence
<220> FEATURE:
<223> OTHER INFORMATION: Synthetic nucleic acid sequence

<400> SEQUENCE: 34
```
agctttgcca gttcct    16

<210> SEQ ID NO 35
<211> LENGTH: 17
<212> TYPE: DNA
<213> ORGANISM: Artificial Sequence
<220> FEATURE:
<223> OTHER INFORMATION: Synthetic nucleic acid sequence

<400> SEQUENCE: 35
agctttgcca gttccgt    17

<210> SEQ ID NO 36
<211> LENGTH: 19
<212> TYPE: DNA
<213> ORGANISM: Artificial Sequence
<220> FEATURE:
<223> OTHER INFORMATION: Synthetic nucleic acid sequence

<400> SEQUENCE: 36
aaaagcaaaa ttgcctgat    19

<210> SEQ ID NO 37
<211> LENGTH: 21
<212> TYPE: DNA
<213> ORGANISM: Artificial Sequence
<220> FEATURE:
<223> OTHER INFORMATION: Synthetic nucleic acid sequence

<400> SEQUENCE: 37
aaaagcaaaa ttgcctgagg c    21

<210> SEQ ID NO 38
<211> LENGTH: 16
<212> TYPE: DNA
<213> ORGANISM: Artificial Sequence
<220> FEATURE:
<223> OTHER INFORMATION: Synthetic nucleic acid sequence

<400> SEQUENCE: 38
tcctgctctt ccctca    16

<210> SEQ ID NO 39
<211> LENGTH: 17
<212> TYPE: DNA
<213> ORGANISM: Artificial Sequence
<220> FEATURE:
<223> OTHER INFORMATION: Synthetic nucleic acid sequence

<400> SEQUENCE: 39
tcctgctctt ccctcgt    17

<210> SEQ ID NO 40
<211> LENGTH: 18
<212> TYPE: DNA
<213> ORGANISM: Artificial Sequence
<220> FEATURE:
<223> OTHER INFORMATION: Synthetic nucleic acid sequence

<400> SEQUENCE: 40
acctccgctg caaataca    18

<210> SEQ ID NO 41
<211> LENGTH: 19
<212> TYPE: DNA
<213> ORGANISM: Artificial Sequence

```
<220> FEATURE:
<223> OTHER INFORMATION: Synthetic nucleic acid sequence

<400> SEQUENCE: 41
acctccgctg caaatacgt                                                    19

<210> SEQ ID NO 42
<211> LENGTH: 19
<212> TYPE: DNA
<213> ORGANISM: Artificial Sequence
<220> FEATURE:
<223> OTHER INFORMATION: Synthetic nucleic acid sequence

<400> SEQUENCE: 42
gagtctggac acgtgggga                                                    19

<210> SEQ ID NO 43
<211> LENGTH: 20
<212> TYPE: DNA
<213> ORGANISM: Artificial Sequence
<220> FEATURE:
<223> OTHER INFORMATION: Synthetic nucleic acid sequence

<400> SEQUENCE: 43
gagtctggac acgtggggga                                                   20

<210> SEQ ID NO 44
<211> LENGTH: 20
<212> TYPE: DNA
<213> ORGANISM: Artificial Sequence
<220> FEATURE:
<223> OTHER INFORMATION: Synthetic nucleic acid sequence

<400> SEQUENCE: 44
tgctgcaggc cccagatgat                                                   20

<210> SEQ ID NO 45
<211> LENGTH: 21
<212> TYPE: DNA
<213> ORGANISM: Artificial Sequence
<220> FEATURE:
<223> OTHER INFORMATION: Synthetic nucleic acid sequence

<400> SEQUENCE: 45
tgctgcaggc cccagatgag c                                                 21

<210> SEQ ID NO 46
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 46
agaaactttt tcgcgaggga ca                                                22

<210> SEQ ID NO 47
<211> LENGTH: 24
<212> TYPE: DNA
<213> ORGANISM: Artificial Sequence
<220> FEATURE:
<223> OTHER INFORMATION: Synthetic nucleic acid sequence

<400> SEQUENCE: 47
agaaactttt tcgcgaggga cggt                                              24
```

```
<210> SEQ ID NO 48
<211> LENGTH: 25
<212> TYPE: DNA
<213> ORGANISM: Artificial Sequence
<220> FEATURE:
<223> OTHER INFORMATION: Synthetic nucleic acid sequence

<400> SEQUENCE: 48
agcgccttct tgctggcacc caata                                        25

<210> SEQ ID NO 49
<211> LENGTH: 27
<212> TYPE: DNA
<213> ORGANISM: Artificial Sequence
<220> FEATURE:
<223> OTHER INFORMATION: Synthetic nucleic acid sequence

<400> SEQUENCE: 49
agcgccttct tgctggcacc caatgga                                      27

<210> SEQ ID NO 50
<211> LENGTH: 23
<212> TYPE: DNA
<213> ORGANISM: Artificial Sequence
<220> FEATURE:
<223> OTHER INFORMATION: Synthetic nucleic acid sequence

<400> SEQUENCE: 50
tcttacaaca caaaatcaaa tct                                          23

<210> SEQ ID NO 51
<211> LENGTH: 24
<212> TYPE: DNA
<213> ORGANISM: Artificial Sequence
<220> FEATURE:
<223> OTHER INFORMATION: Synthetic nucleic acid sequence

<400> SEQUENCE: 51
tcttacaaca caaaatcaaa tcac                                         24

<210> SEQ ID NO 52
<211> LENGTH: 16
<212> TYPE: DNA
<213> ORGANISM: Artificial Sequence
<220> FEATURE:
<223> OTHER INFORMATION: Synthetic nucleic acid sequence

<400> SEQUENCE: 52
agctgaaact tctggc                                                  16

<210> SEQ ID NO 53
<211> LENGTH: 17
<212> TYPE: DNA
<213> ORGANISM: Artificial Sequence
<220> FEATURE:
<223> OTHER INFORMATION: Synthetic nucleic acid sequence

<400> SEQUENCE: 53
agctgaaact tctggga                                                 17

<210> SEQ ID NO 54
<211> LENGTH: 21
<212> TYPE: DNA
<213> ORGANISM: Artificial Sequence
<220> FEATURE:
<223> OTHER INFORMATION: Synthetic nucleic acid sequence

<400> SEQUENCE: 54
```
tcaagcttgc caaagtaatc t                                           21

<210> SEQ ID NO 55
<211> LENGTH: 23
<212> TYPE: DNA
<213> ORGANISM: Artificial Sequence
<220> FEATURE:
<223> OTHER INFORMATION: Synthetic nucleic acid sequence

<400> SEQUENCE: 55
tcaagcttgc caaagtaatc gga                                         23

<210> SEQ ID NO 56
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 56
acgttggatg gaagtcagag atgatggcag                                  30

<210> SEQ ID NO 57
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 57
acgttggatg atgaatcctg gacccaagac                                  30

<210> SEQ ID NO 58
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 58
acgttggatg gaaagatgtg cgctgatagg                                  30

<210> SEQ ID NO 59
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 59
acgttggatg gccacatctc tttctgcatc                                  30

<210> SEQ ID NO 60
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 60
acgttggatg ttgcaggtgt cccatcggaa                                  30

<210> SEQ ID NO 61
<211> LENGTH: 30
<212> TYPE: DNA
<213> ORGANISM: Artificial Sequence

```
<220> FEATURE:
<223> OTHER INFORMATION: Synthetic nucleic acid sequence

<400> SEQUENCE: 61
acgttggatg tagctcgtgg tggctgtgca                                              30

<210> SEQ ID NO 62
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 62
acgttggatg gtgatcaccc aaggcttcag                                              30

<210> SEQ ID NO 63
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 63
acgttggatg gtctgttgac tcttttggcc                                              30

<210> SEQ ID NO 64
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 64
acgttggatg gtagctctcc aggcatcaac                                              30

<210> SEQ ID NO 65
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 65
acgttggatg gtacctggtt cccccttttc                                              30

<210> SEQ ID NO 66
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 66
acgttggatg tgatcttgtt caccttgccg                                              30

<210> SEQ ID NO 67
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 67
acgttggatg agatcgaggt gacgtttgac                                              30
```

```
<210> SEQ ID NO 68
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 68
acgttggatg agacacagaa ccctagatgc                                    30

<210> SEQ ID NO 69
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 69
acgttggatg gcaatgaagg atgtttcagg                                    30

<210> SEQ ID NO 70
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 70
acgttggatg taagacagct ccacagcatc                                    30

<210> SEQ ID NO 71
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 71
acgttggatg ttccatttcc tcaccctcag                                    30

<210> SEQ ID NO 72
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 72
acgttggatg gatttgtgtg taggaccctg                                    30

<210> SEQ ID NO 73
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 73
acgttggatg ggtccccaaa agaaatggag                                    30

<210> SEQ ID NO 74
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 74
```
acgttggatg ggattggaga acaaactcac					30

<210> SEQ ID NO 75
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 75
acgttggatg ggcagctgtt acaccaaaag					30

<210> SEQ ID NO 76
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 76
acgttggatg ctggcgtttt gcaaacatac					30

<210> SEQ ID NO 77
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 77
acgttggatg ttgactggaa gaagcaggtg					30

<210> SEQ ID NO 78
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 78
acgttggatg cctgccaaag aagaaacacc					30

<210> SEQ ID NO 79
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 79
acgttggatg acgtctgcag gtatgtattc					30

<210> SEQ ID NO 80
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 80
acgttggatg acttcatcca cgtgaagccc					30

<210> SEQ ID NO 81
<211> LENGTH: 30
<212> TYPE: DNA
<213> ORGANISM: Artificial Sequence

```
<220> FEATURE:
<223> OTHER INFORMATION: Synthetic nucleic acid sequence

<400> SEQUENCE: 81
acgttggatg aaactcgtag aaagagccgg                                     30

<210> SEQ ID NO 82
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 82
acgttggatg attttctcct cagaggctcc                                     30

<210> SEQ ID NO 83
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 83
acgttggatg tgtctgtatt gagggtgtgg                                     30

<210> SEQ ID NO 84
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 84
acgttggatg ttgctggcac ccaatggaag                                     30

<210> SEQ ID NO 85
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 85
acgttggatg atgagagaca tgacgatgcc                                     30

<210> SEQ ID NO 86
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 86
acgttggatg actcacagag cacattcacg                                     30

<210> SEQ ID NO 87
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 87
acgttggatg tgtcactcga gatcttgagg                                     30
```

```
<210> SEQ ID NO 88
<211> LENGTH: 17
<212> TYPE: DNA
<213> ORGANISM: Artificial Sequence
<220> FEATURE:
<223> OTHER INFORMATION: Synthetic nucleic acid sequence

<400> SEQUENCE: 88
gtgcctgtgc tgggctc                                                    17

<210> SEQ ID NO 89
<211> LENGTH: 18
<212> TYPE: DNA
<213> ORGANISM: Artificial Sequence
<220> FEATURE:
<223> OTHER INFORMATION: Synthetic nucleic acid sequence

<400> SEQUENCE: 89
ggatggagag aaaaaaac                                                   18

<210> SEQ ID NO 90
<211> LENGTH: 17
<212> TYPE: DNA
<213> ORGANISM: Artificial Sequence
<220> FEATURE:
<223> OTHER INFORMATION: Synthetic nucleic acid sequence

<400> SEQUENCE: 90
ccctcatgtc atctact                                                    17

<210> SEQ ID NO 91
<211> LENGTH: 17
<212> TYPE: DNA
<213> ORGANISM: Artificial Sequence
<220> FEATURE:
<223> OTHER INFORMATION: Synthetic nucleic acid sequence

<400> SEQUENCE: 91
gtcacccact ctgttgc                                                    17

<210> SEQ ID NO 92
<211> LENGTH: 17
<212> TYPE: DNA
<213> ORGANISM: Artificial Sequence
<220> FEATURE:
<223> OTHER INFORMATION: Synthetic nucleic acid sequence

<400> SEQUENCE: 92
caaagatggg cgtgatg                                                    17

<210> SEQ ID NO 93
<211> LENGTH: 20
<212> TYPE: DNA
<213> ORGANISM: Artificial Sequence
<220> FEATURE:
<223> OTHER INFORMATION: Synthetic nucleic acid sequence

<400> SEQUENCE: 93
ccttgccggt gctcttgtcc                                                 20

<210> SEQ ID NO 94
<211> LENGTH: 20
<212> TYPE: DNA
<213> ORGANISM: Artificial Sequence
<220> FEATURE:
<223> OTHER INFORMATION: Synthetic nucleic acid sequence

<400> SEQUENCE: 94
```
cagaatcctt cctgttacgg                                              20

<210> SEQ ID NO 95
<211> LENGTH: 23
<212> TYPE: DNA
<213> ORGANISM: Artificial Sequence
<220> FEATURE:
<223> OTHER INFORMATION: Synthetic nucleic acid sequence

<400> SEQUENCE: 95
tccaccaaga cttaagtttt gct                                          23

<210> SEQ ID NO 96
<211> LENGTH: 17
<212> TYPE: DNA
<213> ORGANISM: Artificial Sequence
<220> FEATURE:
<223> OTHER INFORMATION: Synthetic nucleic acid sequence

<400> SEQUENCE: 96
gaggctgaac cccgtcc                                                 17

<210> SEQ ID NO 97
<211> LENGTH: 19
<212> TYPE: DNA
<213> ORGANISM: Artificial Sequence
<220> FEATURE:
<223> OTHER INFORMATION: Synthetic nucleic acid sequence

<400> SEQUENCE: 97 cttttcata gagtcctgt                                                19

<210> SEQ ID NO 98
<211> LENGTH: 19
<212> TYPE: DNA
<213> ORGANISM: Artificial Sequence
<220> FEATURE:
<223> OTHER INFORMATION: Synthetic nucleic acid sequence

<400> SEQUENCE: 98
ttagtcttga agtgagggt                                               19

<210> SEQ ID NO 99
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 99
tacttattta cgcttgaacc tc                                           22

<210> SEQ ID NO 100
<211> LENGTH: 17
<212> TYPE: DNA
<213> ORGANISM: Artificial Sequence
<220> FEATURE:
<223> OTHER INFORMATION: Synthetic nucleic acid sequence

<400> SEQUENCE: 100
ccagctgccc gcaggcc                                                 17

<210> SEQ ID NO 101
<211> LENGTH: 17
<212> TYPE: DNA
<213> ORGANISM: Artificial Sequence

```
<220> FEATURE:
<223> OTHER INFORMATION: Synthetic nucleic acid sequence

<400> SEQUENCE: 101
aattgacaga gagctcc                                                  17

<210> SEQ ID NO 102
<211> LENGTH: 15
<212> TYPE: DNA
<213> ORGANISM: Artificial Sequence
<220> FEATURE:
<223> OTHER INFORMATION: Synthetic nucleic acid sequence

<400> SEQUENCE: 102
cacgacgtca cgcag                                                    15

<210> SEQ ID NO 103
<211> LENGTH: 17
<212> TYPE: DNA
<213> ORGANISM: Artificial Sequence
<220> FEATURE:
<223> OTHER INFORMATION: Synthetic nucleic acid sequence

<400> SEQUENCE: 103
cacattcacg gtcacct                                                  17

<210> SEQ ID NO 104
<211> LENGTH: 18
<212> TYPE: DNA
<213> ORGANISM: Artificial Sequence
<220> FEATURE:
<223> OTHER INFORMATION: Synthetic nucleic acid sequence

<400> SEQUENCE: 104
gtgcctgtgc tgggctca                                                 18

<210> SEQ ID NO 105
<211> LENGTH: 19
<212> TYPE: DNA
<213> ORGANISM: Artificial Sequence
<220> FEATURE:
<223> OTHER INFORMATION: Synthetic nucleic acid sequence

<400> SEQUENCE: 105
gtgcctgtgc tgggctcgt                                                19

<210> SEQ ID NO 106
<211> LENGTH: 19
<212> TYPE: DNA
<213> ORGANISM: Artificial Sequence
<220> FEATURE:
<223> OTHER INFORMATION: Synthetic nucleic acid sequence

<400> SEQUENCE: 106
ggatggagag aaaaaaaca                                                19

<210> SEQ ID NO 107
<211> LENGTH: 20
<212> TYPE: DNA
<213> ORGANISM: Artificial Sequence
<220> FEATURE:
<223> OTHER INFORMATION: Synthetic nucleic acid sequence

<400> SEQUENCE: 107
ggatggagag aaaaaaacgt                                               20
```

```
<210> SEQ ID NO 108
<211> LENGTH: 18
<212> TYPE: DNA
<213> ORGANISM: Artificial Sequence
<220> FEATURE:
<223> OTHER INFORMATION: Synthetic nucleic acid sequence

<400> SEQUENCE: 108
ccctcatgtc atctacta                                                 18

<210> SEQ ID NO 109
<211> LENGTH: 19
<212> TYPE: DNA
<213> ORGANISM: Artificial Sequence
<220> FEATURE:
<223> OTHER INFORMATION: Synthetic nucleic acid sequence

<400> SEQUENCE: 109
ccctcatgtc atctactgc                                                19

<210> SEQ ID NO 110
<211> LENGTH: 18
<212> TYPE: DNA
<213> ORGANISM: Artificial Sequence
<220> FEATURE:
<223> OTHER INFORMATION: Synthetic nucleic acid sequence

<400> SEQUENCE: 110
gtcacccact ctgttgcc                                                 18

<210> SEQ ID NO 111
<211> LENGTH: 19
<212> TYPE: DNA
<213> ORGANISM: Artificial Sequence
<220> FEATURE:
<223> OTHER INFORMATION: Synthetic nucleic acid sequence

<400> SEQUENCE: 111
gtcacccact ctgttgcgc                                                19

<210> SEQ ID NO 112
<211> LENGTH: 18
<212> TYPE: DNA
<213> ORGANISM: Artificial Sequence
<220> FEATURE:
<223> OTHER INFORMATION: Synthetic nucleic acid sequence

<400> SEQUENCE: 112
caaagatggg cgtgatga                                                 18

<210> SEQ ID NO 113
<211> LENGTH: 19
<212> TYPE: DNA
<213> ORGANISM: Artificial Sequence
<220> FEATURE:
<223> OTHER INFORMATION: Synthetic nucleic acid sequence

<400> SEQUENCE: 113
caaagatggg cgtgatggc                                                19

<210> SEQ ID NO 114
<211> LENGTH: 21
<212> TYPE: DNA
<213> ORGANISM: Artificial Sequence
<220> FEATURE:
<223> OTHER INFORMATION: Synthetic nucleic acid sequence

<400> SEQUENCE: 114
```
ccttgccggt gctcttgtcc a                                              21

<210> SEQ ID NO 115
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 115
ccttgccggt gctcttgtcc gt                                             22

<210> SEQ ID NO 116
<211> LENGTH: 21
<212> TYPE: DNA
<213> ORGANISM: Artificial Sequence
<220> FEATURE:
<223> OTHER INFORMATION: Synthetic nucleic acid sequence

<400> SEQUENCE: 116
cagaatcctt cctgttacgg c                                              21

<210> SEQ ID NO 117
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 117
cagaatcctt cctgttacgg tc                                             22

<210> SEQ ID NO 118
<211> LENGTH: 24
<212> TYPE: DNA
<213> ORGANISM: Artificial Sequence
<220> FEATURE:
<223> OTHER INFORMATION: Synthetic nucleic acid sequence

<400> SEQUENCE: 118
tccaccaaga cttaagtttt gctc                                           24

<210> SEQ ID NO 119
<211> LENGTH: 25
<212> TYPE: DNA
<213> ORGANISM: Artificial Sequence
<220> FEATURE:
<223> OTHER INFORMATION: Synthetic nucleic acid sequence

<400> SEQUENCE: 119
tccaccaaga cttaagtttt gcttc                                          25

<210> SEQ ID NO 120
<211> LENGTH: 18
<212> TYPE: DNA
<213> ORGANISM: Artificial Sequence
<220> FEATURE:
<223> OTHER INFORMATION: Synthetic nucleic acid sequence

<400> SEQUENCE: 120
gaggctgaac cccgtccc                                                  18

<210> SEQ ID NO 121
<211> LENGTH: 19
<212> TYPE: DNA
<213> ORGANISM: Artificial Sequence

```
<220> FEATURE:
<223> OTHER INFORMATION: Synthetic nucleic acid sequence

<400> SEQUENCE: 121
gaggctgaac cccgtcctc                                                        19

<210> SEQ ID NO 122
<211> LENGTH: 20
<212> TYPE: DNA
<213> ORGANISM: Artificial Sequence
<220> FEATURE:
<223> OTHER INFORMATION: Synthetic nucleic acid sequence

<400> SEQUENCE: 122 cttttcata gagtcctgtt                                                        20

<210> SEQ ID NO 123
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 123 cttttcata gagtcctgta ac                                                     22

<210> SEQ ID NO 124
<211> LENGTH: 20
<212> TYPE: DNA
<213> ORGANISM: Artificial Sequence
<220> FEATURE:
<223> OTHER INFORMATION: Synthetic nucleic acid sequence

<400> SEQUENCE: 124
ttagtcttga agtgagggta                                                       20

<210> SEQ ID NO 125
<211> LENGTH: 21
<212> TYPE: DNA
<213> ORGANISM: Artificial Sequence
<220> FEATURE:
<223> OTHER INFORMATION: Synthetic nucleic acid sequence

<400> SEQUENCE: 125
ttagtcttga agtgagggtg t                                                     21

<210> SEQ ID NO 126
<211> LENGTH: 23
<212> TYPE: DNA
<213> ORGANISM: Artificial Sequence
<220> FEATURE:
<223> OTHER INFORMATION: Synthetic nucleic acid sequence

<400> SEQUENCE: 126
tacttattta cgcttgaacc tca                                                   23

<210> SEQ ID NO 127
<211> LENGTH: 24
<212> TYPE: DNA
<213> ORGANISM: Artificial Sequence
<220> FEATURE:
<223> OTHER INFORMATION: Synthetic nucleic acid sequence

<400> SEQUENCE: 127
tacttattta cgcttgaacc tcga                                                  24
```

-continued

```
<210> SEQ ID NO 128
<211> LENGTH: 18
<212> TYPE: DNA
<213> ORGANISM: Artificial Sequence
<220> FEATURE:
<223> OTHER INFORMATION: Synthetic nucleic acid sequence

<400> SEQUENCE: 128
ccagctgccc gcaggcca                                                 18

<210> SEQ ID NO 129
<211> LENGTH: 19
<212> TYPE: DNA
<213> ORGANISM: Artificial Sequence
<220> FEATURE:
<223> OTHER INFORMATION: Synthetic nucleic acid sequence

<400> SEQUENCE: 129
ccagctgccc gcaggccgt                                                19

<210> SEQ ID NO 130
<211> LENGTH: 18
<212> TYPE: DNA
<213> ORGANISM: Artificial Sequence
<220> FEATURE:
<223> OTHER INFORMATION: Synthetic nucleic acid sequence

<400> SEQUENCE: 130
aattgacaga gagctccc                                                 18

<210> SEQ ID NO 131
<211> LENGTH: 19
<212> TYPE: DNA
<213> ORGANISM: Artificial Sequence
<220> FEATURE:
<223> OTHER INFORMATION: Synthetic nucleic acid sequence

<400> SEQUENCE: 131
aattgacaga gagctcctg                                                19

<210> SEQ ID NO 132
<211> LENGTH: 16
<212> TYPE: DNA
<213> ORGANISM: Artificial Sequence
<220> FEATURE:
<223> OTHER INFORMATION: Synthetic nucleic acid sequence

<400> SEQUENCE: 132
cacgacgtca cgcagc                                                   16

<210> SEQ ID NO 133
<211> LENGTH: 17
<212> TYPE: DNA
<213> ORGANISM: Artificial Sequence
<220> FEATURE:
<223> OTHER INFORMATION: Synthetic nucleic acid sequence

<400> SEQUENCE: 133
cacgacgtca cgcagga                                                  17

<210> SEQ ID NO 134
<211> LENGTH: 18
<212> TYPE: DNA
<213> ORGANISM: Artificial Sequence
<220> FEATURE:
<223> OTHER INFORMATION: Synthetic nucleic acid sequence

<400> SEQUENCE: 134
```
cacattcacg gtcacctc                                          18

<210> SEQ ID NO 135
<211> LENGTH: 19
<212> TYPE: DNA
<213> ORGANISM: Artificial Sequence
<220> FEATURE:
<223> OTHER INFORMATION: Synthetic nucleic acid sequence

<400> SEQUENCE: 135
cacattcacg gtcaccttg                                         19

<210> SEQ ID NO 136
<211> LENGTH: 21
<212> TYPE: DNA
<213> ORGANISM: Artificial Sequence
<220> FEATURE:
<223> OTHER INFORMATION: Synthetic nucleic acid sequence

<400> SEQUENCE: 136
ctaccaggaa tggccttgtc c                                      21

<210> SEQ ID NO 137
<211> LENGTH: 21
<212> TYPE: DNA
<213> ORGANISM: Artificial Sequence
<220> FEATURE:
<223> OTHER INFORMATION: Synthetic nucleic acid sequence

<400> SEQUENCE: 137
ctctcaggtc tggtgtcatc c                                      21

<210> SEQ ID NO 138
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 138
gattagcata cttagactac tacctccatg                             30

<210> SEQ ID NO 139
<211> LENGTH: 27
<212> TYPE: DNA
<213> ORGANISM: Artificial Sequence
<220> FEATURE:
<223> OTHER INFORMATION: Synthetic nucleic acid sequence

<400> SEQUENCE: 139
gatcaacttc tgaaaagca ttcccac                                 27

<210> SEQ ID NO 140
<211> LENGTH: 21
<212> TYPE: DNA
<213> ORGANISM: Artificial Sequence
<220> FEATURE:
<223> OTHER INFORMATION: Synthetic nucleic acid sequence

<400> SEQUENCE: 140
tcgtgagaat gtcttcccat t                                      21

<210> SEQ ID NO 141
<211> LENGTH: 29
<212> TYPE: DNA
<213> ORGANISM: Artificial Sequence

```
<220> FEATURE:
<223> OTHER INFORMATION: Synthetic nucleic acid sequence

<400> SEQUENCE: 141
tcttggattg atttgagata agtgaaatc                                29

<210> SEQ ID NO 142
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 142
acgttggatg gcttgttaac cagctttgcc                               30

<210> SEQ ID NO 143
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 143
acgttggatg ttttcagac tggcagagcg                                30

<210> SEQ ID NO 144
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 144
acgttggatg ttttcagac tggcagagcg                                30

<210> SEQ ID NO 145
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 145
acgttggatg gcttgttaac cagctttgcc                               30

<210> SEQ ID NO 146
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 146
acgttggatg ttgctggcac ccaatggaag                               30

<210> SEQ ID NO 147
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 147
acgttggatg atgagagaca tgacgatgcc                               30
```

```
<210> SEQ ID NO 148
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 148
acgttggatg tggtggacat ggtgaatgac                               30

<210> SEQ ID NO 149
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 149
acgttggatg tggtgcagat gctcacatag                               30

<210> SEQ ID NO 150
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 150
acgttggatg cacagagaga gtctggacac                               30

<210> SEQ ID NO 151
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 151
acgttggatg ctcttggtct ttccctcatc                               30

<210> SEQ ID NO 152
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 152
acgttggatg cctctgatcc tctttgcttc                               30

<210> SEQ ID NO 153
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 153
acgttggatg aagagggagt ggaagggaag                               30

<210> SEQ ID NO 154
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 154
```
acgttggatg acagctctgc attcagcacg            30

<210> SEQ ID NO 155
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 155
acgttggatg agtcaatccc tttggtgctc            30

<210> SEQ ID NO 156
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 156
acgttggatg actgaagctc cacaatttgg            30

<210> SEQ ID NO 157
<211> LENGTH: 31
<212> TYPE: DNA
<213> ORGANISM: Artificial Sequence
<220> FEATURE:
<223> OTHER INFORMATION: Synthetic nucleic acid sequence

<400> SEQUENCE: 157
acgttggatg gccactctag tactatatct g          31

<210> SEQ ID NO 158
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 158
acgttggatg gggtattcat aagctgaaac            30

<210> SEQ ID NO 159
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 159
acgttggatg ccttcaagtt cagtggtcag            30

<210> SEQ ID NO 160
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 160
acgttggatg ggtcaatgaa gagaacttgg            30

<210> SEQ ID NO 161
<211> LENGTH: 30
<212> TYPE: DNA
<213> ORGANISM: Artificial Sequence

```
<220> FEATURE:
<223> OTHER INFORMATION: Synthetic nucleic acid sequence

<400> SEQUENCE: 161
acgttggatg aatgtttatt gtagaaaacc                                              30

<210> SEQ ID NO 162
<211> LENGTH: 15
<212> TYPE: DNA
<213> ORGANISM: Artificial Sequence
<220> FEATURE:
<223> OTHER INFORMATION: Synthetic nucleic acid sequence

<400> SEQUENCE: 162
agctttgcca gttcc                                                              15

<210> SEQ ID NO 163
<211> LENGTH: 18
<212> TYPE: DNA
<213> ORGANISM: Artificial Sequence
<220> FEATURE:
<223> OTHER INFORMATION: Synthetic nucleic acid sequence

<400> SEQUENCE: 163
aaaagcaaaa ttgcctga                                                           18

<210> SEQ ID NO 164
<211> LENGTH: 15
<212> TYPE: DNA
<213> ORGANISM: Artificial Sequence
<220> FEATURE:
<223> OTHER INFORMATION: Synthetic nucleic acid sequence

<400> SEQUENCE: 164
cacgacgtca cgcag                                                              15

<210> SEQ ID NO 165
<211> LENGTH: 17
<212> TYPE: DNA
<213> ORGANISM: Artificial Sequence
<220> FEATURE:
<223> OTHER INFORMATION: Synthetic nucleic acid sequence

<400> SEQUENCE: 165
acctccgctg caaatac                                                            17

<210> SEQ ID NO 166
<211> LENGTH: 18
<212> TYPE: DNA
<213> ORGANISM: Artificial Sequence
<220> FEATURE:
<223> OTHER INFORMATION: Synthetic nucleic acid sequence

<400> SEQUENCE: 166
gagtctggac acgtgggg                                                           18

<210> SEQ ID NO 167
<211> LENGTH: 19
<212> TYPE: DNA
<213> ORGANISM: Artificial Sequence
<220> FEATURE:
<223> OTHER INFORMATION: Synthetic nucleic acid sequence

<400> SEQUENCE: 167
tccatctctg tggatctcc                                                          19
```

```
<210> SEQ ID NO 168
<211> LENGTH: 19
<212> TYPE: DNA
<213> ORGANISM: Artificial Sequence
<220> FEATURE:
<223> OTHER INFORMATION: Synthetic nucleic acid sequence

<400> SEQUENCE: 168
tgctgcaggc cccagatga                                         19

<210> SEQ ID NO 169
<211> LENGTH: 21
<212> TYPE: DNA
<213> ORGANISM: Artificial Sequence
<220> FEATURE:
<223> OTHER INFORMATION: Synthetic nucleic acid sequence

<400> SEQUENCE: 169
cacaatttgg tgaattatca a                                      21

<210> SEQ ID NO 170
<211> LENGTH: 15
<212> TYPE: DNA
<213> ORGANISM: Artificial Sequence
<220> FEATURE:
<223> OTHER INFORMATION: Synthetic nucleic acid sequence

<400> SEQUENCE: 170
agctgaaact tctgg                                             15

<210> SEQ ID NO 171
<211> LENGTH: 20
<212> TYPE: DNA
<213> ORGANISM: Artificial Sequence
<220> FEATURE:
<223> OTHER INFORMATION: Synthetic nucleic acid sequence

<400> SEQUENCE: 171
tcaagcttgc caaagtaatc                                        20

<210> SEQ ID NO 172
<211> LENGTH: 16
<212> TYPE: DNA
<213> ORGANISM: Artificial Sequence
<220> FEATURE:
<223> OTHER INFORMATION: Synthetic nucleic acid sequence

<400> SEQUENCE: 172
agctttgcca gttcct                                            16

<210> SEQ ID NO 173
<211> LENGTH: 17
<212> TYPE: DNA
<213> ORGANISM: Artificial Sequence
<220> FEATURE:
<223> OTHER INFORMATION: Synthetic nucleic acid sequence

<400> SEQUENCE: 173
agctttgcca gttccgt                                           17

<210> SEQ ID NO 174
<211> LENGTH: 19
<212> TYPE: DNA
<213> ORGANISM: Artificial Sequence
<220> FEATURE:
<223> OTHER INFORMATION: Synthetic nucleic acid sequence

<400> SEQUENCE: 174
```
aaaagcaaaa ttgcctgat                                              19

<210> SEQ ID NO 175
<211> LENGTH: 21
<212> TYPE: DNA
<213> ORGANISM: Artificial Sequence
<220> FEATURE:
<223> OTHER INFORMATION: Synthetic nucleic acid sequence

<400> SEQUENCE: 175
aaaagcaaaa ttgcctgagg c                                           21

<210> SEQ ID NO 176
<211> LENGTH: 16
<212> TYPE: DNA
<213> ORGANISM: Artificial Sequence
<220> FEATURE:
<223> OTHER INFORMATION: Synthetic nucleic acid sequence

<400> SEQUENCE: 176
cacgacgtca cgcagc                                                 16

<210> SEQ ID NO 177
<211> LENGTH: 17
<212> TYPE: DNA
<213> ORGANISM: Artificial Sequence
<220> FEATURE:
<223> OTHER INFORMATION: Synthetic nucleic acid sequence

<400> SEQUENCE: 177
cacgacgtca cgcagga                                                17

<210> SEQ ID NO 178
<211> LENGTH: 18
<212> TYPE: DNA
<213> ORGANISM: Artificial Sequence
<220> FEATURE:
<223> OTHER INFORMATION: Synthetic nucleic acid sequence

<400> SEQUENCE: 178
acctccgctg caaataca                                               18

<210> SEQ ID NO 179
<211> LENGTH: 19
<212> TYPE: DNA
<213> ORGANISM: Artificial Sequence
<220> FEATURE:
<223> OTHER INFORMATION: Synthetic nucleic acid sequence

<400> SEQUENCE: 179
acctccgctg caaatacgt                                              19

<210> SEQ ID NO 180
<211> LENGTH: 19
<212> TYPE: DNA
<213> ORGANISM: Artificial Sequence
<220> FEATURE:
<223> OTHER INFORMATION: Synthetic nucleic acid sequence

<400> SEQUENCE: 180
gagtctggac acgtgggga                                              19

<210> SEQ ID NO 181
<211> LENGTH: 20
<212> TYPE: DNA
<213> ORGANISM: Artificial Sequence

```
<220> FEATURE:
<223> OTHER INFORMATION: Synthetic nucleic acid sequence

<400> SEQUENCE: 181
gagtctggac acgtggggga                                              20

<210> SEQ ID NO 182
<211> LENGTH: 20
<212> TYPE: DNA
<213> ORGANISM: Artificial Sequence
<220> FEATURE:
<223> OTHER INFORMATION: Synthetic nucleic acid sequence

<400> SEQUENCE: 182
tccatctctg tggatctcca                                              20

<210> SEQ ID NO 183
<211> LENGTH: 21
<212> TYPE: DNA
<213> ORGANISM: Artificial Sequence
<220> FEATURE:
<223> OTHER INFORMATION: Synthetic nucleic acid sequence

<400> SEQUENCE: 183
tccatctctg tggatctccg t                                            21

<210> SEQ ID NO 184
<211> LENGTH: 20
<212> TYPE: DNA
<213> ORGANISM: Artificial Sequence
<220> FEATURE:
<223> OTHER INFORMATION: Synthetic nucleic acid sequence

<400> SEQUENCE: 184
tgctgcaggc cccagatgat                                              20

<210> SEQ ID NO 185
<211> LENGTH: 21
<212> TYPE: DNA
<213> ORGANISM: Artificial Sequence
<220> FEATURE:
<223> OTHER INFORMATION: Synthetic nucleic acid sequence

<400> SEQUENCE: 185
tgctgcaggc cccagatgag c                                            21

<210> SEQ ID NO 186
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 186
cacaatttgg tgaattatca at                                           22

<210> SEQ ID NO 187
<211> LENGTH: 23
<212> TYPE: DNA
<213> ORGANISM: Artificial Sequence
<220> FEATURE:
<223> OTHER INFORMATION: Synthetic nucleic acid sequence

<400> SEQUENCE: 187
cacaatttgg tgaattatca aat                                          23
```

```
<210> SEQ ID NO 188
<211> LENGTH: 16
<212> TYPE: DNA
<213> ORGANISM: Artificial Sequence
<220> FEATURE:
<223> OTHER INFORMATION: Synthetic nucleic acid sequence

<400> SEQUENCE: 188
agctgaaact tctggc                                               16

<210> SEQ ID NO 189
<211> LENGTH: 17
<212> TYPE: DNA
<213> ORGANISM: Artificial Sequence
<220> FEATURE:
<223> OTHER INFORMATION: Synthetic nucleic acid sequence

<400> SEQUENCE: 189
agctgaaact tctggga                                              17

<210> SEQ ID NO 190
<211> LENGTH: 21
<212> TYPE: DNA
<213> ORGANISM: Artificial Sequence
<220> FEATURE:
<223> OTHER INFORMATION: Synthetic nucleic acid sequence

<400> SEQUENCE: 190
tcaagcttgc caaagtaatc t                                         21

<210> SEQ ID NO 191
<211> LENGTH: 23
<212> TYPE: DNA
<213> ORGANISM: Artificial Sequence
<220> FEATURE:
<223> OTHER INFORMATION: Synthetic nucleic acid sequence

<400> SEQUENCE: 191
tcaagcttgc caaagtaatc gga                                       23

<210> SEQ ID NO 192
<211> LENGTH: 20
<212> TYPE: DNA
<213> ORGANISM: Artificial Sequence
<220> FEATURE:
<223> OTHER INFORMATION: Synthetic nucleic acid sequence

<400> SEQUENCE: 192
ctgccctact tgattgatgg                                           20

<210> SEQ ID NO 193
<211> LENGTH: 20
<212> TYPE: DNA
<213> ORGANISM: Artificial Sequence
<220> FEATURE:
<223> OTHER INFORMATION: Synthetic nucleic acid sequence

<400> SEQUENCE: 193
atcttctcct cttctgtctc                                           20

<210> SEQ ID NO 194
<211> LENGTH: 20
<212> TYPE: DNA
<213> ORGANISM: Artificial Sequence
<220> FEATURE:
<223> OTHER INFORMATION: Synthetic nucleic acid sequence

<400> SEQUENCE: 194
```
ttctggattg tagcagatca                                                    20

<210> SEQ ID NO 195
<211> LENGTH: 21
<212> TYPE: DNA
<213> ORGANISM: Artificial Sequence
<220> FEATURE:
<223> OTHER INFORMATION: Synthetic nucleic acid sequence

<400> SEQUENCE: 195
tcgtgagaat gtcttcccat t                                                  21

<210> SEQ ID NO 196
<211> LENGTH: 29
<212> TYPE: DNA
<213> ORGANISM: Artificial Sequence
<220> FEATURE:
<223> OTHER INFORMATION: Synthetic nucleic acid sequence

<400> SEQUENCE: 196
tcttggattg atttgagata agtgaaatc                                          29

<210> SEQ ID NO 197
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 197
acgttggatg aaaccagagg gaagcaaagg                                         30

<210> SEQ ID NO 198
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 198
acgttggatg tcattggttg tgctgcacct                                         30

<210> SEQ ID NO 199
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 199
acgttggatg caccaggaac cgtttatggc                                         30

<210> SEQ ID NO 200
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 200
acgttggatg agcagctaga atcagaggag                                         30

<210> SEQ ID NO 201
<211> LENGTH: 31
<212> TYPE: DNA
<213> ORGANISM: Artificial Sequence

```
<220> FEATURE:
<223> OTHER INFORMATION: Synthetic nucleic acid sequence

<400> SEQUENCE: 201
acgttggatg gtcaatgaag agaacttggt c                              31

<210> SEQ ID NO 202
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 202
acgttggatg aatgtttatt gtagaaaacc                                30

<210> SEQ ID NO 203
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 203
acgttggatg gggtattcat aagctgaaac                                30

<210> SEQ ID NO 204
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 204
acgttggatg ccttcaagtt cagtggtcag                                30

<210> SEQ ID NO 205
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 205
acgttggatg gtgattatct ttggcatggg                                30

<210> SEQ ID NO 206
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 206
acgttggatg ggatagccag gaagagaaag                                30

<210> SEQ ID NO 207
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 207
acgttggatg ccctatttct ttgtcttcac                                30
```

```
<210> SEQ ID NO 208
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 208
acgttggatg cttgggataa tttggctctg                                         30

<210> SEQ ID NO 209
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 209
acgttggatg ggaaccettt ctgcgctttg                                         30

<210> SEQ ID NO 210
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 210
acgttggatg cctacaggtg ctgttcagtg                                         30

<210> SEQ ID NO 211
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 211
acgttggatg cctgccaaag aagaaacacc                                         30

<210> SEQ ID NO 212
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 212
acgttggatg acgtctgcag gtatgtattc                                         30

<210> SEQ ID NO 213
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 213
acgttggatg gttcttaatt cataggttgc                                         30

<210> SEQ ID NO 214
<211> LENGTH: 32
<212> TYPE: DNA
<213> ORGANISM: Artificial Sequence
<220> FEATURE:
<223> OTHER INFORMATION: Synthetic nucleic acid sequence

<400> SEQUENCE: 214
```
acgttggatg cttcatttct catcatattt tc                                    32

<210> SEQ ID NO 215
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 215
acgttggatg taggtgtctc cccctgtaag                                       30

<210> SEQ ID NO 216
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 216
acgttggatg tcctctccag agtgatcaag                                       30

<210> SEQ ID NO 217
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 217
acgttggatg attttctcct cagaggctcc                                       30

<210> SEQ ID NO 218
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 218
acgttggatg tgtctgtatt gagggtgtgg                                       30

<210> SEQ ID NO 219
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 219
acgttggatg ttgtggctgc aacatgagag                                       30

<210> SEQ ID NO 220
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 220
acgttggatg ctatggcgca acatctgtac                                       30

<210> SEQ ID NO 221
<211> LENGTH: 30
<212> TYPE: DNA
<213> ORGANISM: Artificial Sequence

```
<220> FEATURE:
<223> OTHER INFORMATION: Synthetic nucleic acid sequence

<400> SEQUENCE: 221
acgttggatg actgtagttt ccctagtccc                                    30

<210> SEQ ID NO 222
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 222
acgttggatg agtcagcaga gagactaggg                                    30

<210> SEQ ID NO 223
<211> LENGTH: 31
<212> TYPE: DNA
<213> ORGANISM: Artificial Sequence
<220> FEATURE:
<223> OTHER INFORMATION: Synthetic nucleic acid sequence

<400> SEQUENCE: 223
acgttggatg gagttgagaa tggagagaat g                                  31

<210> SEQ ID NO 224
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 224
acgttggatg tcaagtgggc tgttagggtg                                    30

<210> SEQ ID NO 225
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 225
acgttggatg tgctgcgtgg tgggcgtgtg                                    30

<210> SEQ ID NO 226
<211> LENGTH: 29
<212> TYPE: DNA
<213> ORGANISM: Artificial Sequence
<220> FEATURE:
<223> OTHER INFORMATION: Synthetic nucleic acid sequence

<400> SEQUENCE: 226
acgttggatg ggccttgcac tcgctctcg                                     29

<210> SEQ ID NO 227
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 227
acgttggatg aaacggtcgc ttcgacgtgc                                    30
```

```
<210> SEQ ID NO 228
<211> LENGTH: 29
<212> TYPE: DNA
<213> ORGANISM: Artificial Sequence
<220> FEATURE:
<223> OTHER INFORMATION: Synthetic nucleic acid sequence

<400> SEQUENCE: 228
acgttggatg acctcaagga ccagctcgg                                29

<210> SEQ ID NO 229
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 229
acgttggatg actgaagctc cacaatttgg                               30

<210> SEQ ID NO 230
<211> LENGTH: 31
<212> TYPE: DNA
<213> ORGANISM: Artificial Sequence
<220> FEATURE:
<223> OTHER INFORMATION: Synthetic nucleic acid sequence

<400> SEQUENCE: 230
acgttggatg gccactctag tactatatct g                             31

<210> SEQ ID NO 231
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 231
acgttggatg cagacattca caattgattt                               30

<210> SEQ ID NO 232
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 232
acgttggatg gatagttcca aacatgtgcg                               30

<210> SEQ ID NO 233
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 233
acgttggatg taaggagtgg gtgctggact                               30

<210> SEQ ID NO 234
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 234
```

```
acgttggatg aggataagga gcagggttgg                                    30

<210> SEQ ID NO 235
<211> LENGTH: 17
<212> TYPE: DNA
<213> ORGANISM: Artificial Sequence
<220> FEATURE:
<223> OTHER INFORMATION: Synthetic nucleic acid sequence

<400> SEQUENCE: 235
ttcttggttc aggagag                                                  17

<210> SEQ ID NO 236
<211> LENGTH: 18
<212> TYPE: DNA
<213> ORGANISM: Artificial Sequence
<220> FEATURE:
<223> OTHER INFORMATION: Synthetic nucleic acid sequence

<400> SEQUENCE: 236
ttcttggttc aggagagc                                                 18

<210> SEQ ID NO 237
<211> LENGTH: 19
<212> TYPE: DNA
<213> ORGANISM: Artificial Sequence
<220> FEATURE:
<223> OTHER INFORMATION: Synthetic nucleic acid sequence

<400> SEQUENCE: 237
gcaatctgct ctatcctct                                                19

<210> SEQ ID NO 238
<211> LENGTH: 20
<212> TYPE: DNA
<213> ORGANISM: Artificial Sequence
<220> FEATURE:
<223> OTHER INFORMATION: Synthetic nucleic acid sequence

<400> SEQUENCE: 238
gcaatctgct ctatcctctt                                               20

<210> SEQ ID NO 239
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 239
attcaagctt gccaaagtaa tc                                            22

<210> SEQ ID NO 240
<211> LENGTH: 23
<212> TYPE: DNA
<213> ORGANISM: Artificial Sequence
<220> FEATURE:
<223> OTHER INFORMATION: Synthetic nucleic acid sequence

<400> SEQUENCE: 240
attcaagctt gccaaagtaa tct                                           23

<210> SEQ ID NO 241
<211> LENGTH: 19
<212> TYPE: DNA
<213> ORGANISM: Artificial Sequence
```

```
<220> FEATURE:
<223> OTHER INFORMATION: Synthetic nucleic acid sequence

<400> SEQUENCE: 241
cataagctga aacttctgg                                              19

<210> SEQ ID NO 242
<211> LENGTH: 20
<212> TYPE: DNA
<213> ORGANISM: Artificial Sequence
<220> FEATURE:
<223> OTHER INFORMATION: Synthetic nucleic acid sequence

<400> SEQUENCE: 242
cataagctga aacttctggc                                             20

<210> SEQ ID NO 243
<211> LENGTH: 20
<212> TYPE: DNA
<213> ORGANISM: Artificial Sequence
<220> FEATURE:
<223> OTHER INFORMATION: Synthetic nucleic acid sequence

<400> SEQUENCE: 243
ggaagtgtat cggtgagacc                                             20

<210> SEQ ID NO 244
<211> LENGTH: 21
<212> TYPE: DNA
<213> ORGANISM: Artificial Sequence
<220> FEATURE:
<223> OTHER INFORMATION: Synthetic nucleic acid sequence

<400> SEQUENCE: 244
ggaagtgtat cggtgagacc a                                           21

<210> SEQ ID NO 245
<211> LENGTH: 23
<212> TYPE: DNA
<213> ORGANISM: Artificial Sequence
<220> FEATURE:
<223> OTHER INFORMATION: Synthetic nucleic acid sequence

<400> SEQUENCE: 245
tgacaaatac tggttaatta gca                                         23

<210> SEQ ID NO 246
<211> LENGTH: 24
<212> TYPE: DNA
<213> ORGANISM: Artificial Sequence
<220> FEATURE:
<223> OTHER INFORMATION: Synthetic nucleic acid sequence

<400> SEQUENCE: 246
tgacaaatac tggttaatta gcaa                                        24

<210> SEQ ID NO 247
<211> LENGTH: 17
<212> TYPE: DNA
<213> ORGANISM: Artificial Sequence
<220> FEATURE:
<223> OTHER INFORMATION: Synthetic nucleic acid sequence

<400> SEQUENCE: 247
gctcctgagc atggcgg                                                17
```

<210> SEQ ID NO 248
<211> LENGTH: 18
<212> TYPE: DNA
<213> ORGANISM: Artificial Sequence
<220> FEATURE:
<223> OTHER INFORMATION: Synthetic nucleic acid sequence

<400> SEQUENCE: 248
gctcctgagc atggcggc                                              18

<210> SEQ ID NO 249
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 249
tacttattta cgcttgaacc tc                                         22

<210> SEQ ID NO 250
<211> LENGTH: 23
<212> TYPE: DNA
<213> ORGANISM: Artificial Sequence
<220> FEATURE:
<223> OTHER INFORMATION: Synthetic nucleic acid sequence

<400> SEQUENCE: 250
tacttattta cgcttgaacc tca                                        23

<210> SEQ ID NO 251
<211> LENGTH: 23
<212> TYPE: DNA
<213> ORGANISM: Artificial Sequence
<220> FEATURE:
<223> OTHER INFORMATION: Synthetic nucleic acid sequence

<400> SEQUENCE: 251
cttaattcat aggttgcaat ttt                                        23

<210> SEQ ID NO 252
<211> LENGTH: 24
<212> TYPE: DNA
<213> ORGANISM: Artificial Sequence
<220> FEATURE:
<223> OTHER INFORMATION: Synthetic nucleic acid sequence

<400> SEQUENCE: 252
cttaattcat aggttgcaat ttta                                       24

<210> SEQ ID NO 253
<211> LENGTH: 17
<212> TYPE: DNA
<213> ORGANISM: Artificial Sequence
<220> FEATURE:
<223> OTHER INFORMATION: Synthetic nucleic acid sequence

<400> SEQUENCE: 253
acatcaccct cacttac                                               17

<210> SEQ ID NO 254
<211> LENGTH: 18
<212> TYPE: DNA
<213> ORGANISM: Artificial Sequence
<220> FEATURE:
<223> OTHER INFORMATION: Synthetic nucleic acid sequence

<400> SEQUENCE: 254

```
acatcaccct cacttacc                                                 18

<210> SEQ ID NO 255
<211> LENGTH: 17
<212> TYPE: DNA
<213> ORGANISM: Artificial Sequence
<220> FEATURE:
<223> OTHER INFORMATION: Synthetic nucleic acid sequence

<400> SEQUENCE: 255
aattgacaga gagctcc                                                  17

<210> SEQ ID NO 256
<211> LENGTH: 18
<212> TYPE: DNA
<213> ORGANISM: Artificial Sequence
<220> FEATURE:
<223> OTHER INFORMATION: Synthetic nucleic acid sequence

<400> SEQUENCE: 256
aattgacaga gagctccc                                                 18

<210> SEQ ID NO 257
<211> LENGTH: 20
<212> TYPE: DNA
<213> ORGANISM: Artificial Sequence
<220> FEATURE:
<223> OTHER INFORMATION: Synthetic nucleic acid sequence

<400> SEQUENCE: 257
atgagaggct cacagacgtt                                               20

<210> SEQ ID NO 258
<211> LENGTH: 21
<212> TYPE: DNA
<213> ORGANISM: Artificial Sequence
<220> FEATURE:
<223> OTHER INFORMATION: Synthetic nucleic acid sequence

<400> SEQUENCE: 258
atgagaggct cacagacgtt c                                             21

<210> SEQ ID NO 259
<211> LENGTH: 21
<212> TYPE: DNA
<213> ORGANISM: Artificial Sequence
<220> FEATURE:
<223> OTHER INFORMATION: Synthetic nucleic acid sequence

<400> SEQUENCE: 259
ggcatcaagc tcttccctgg c                                             21

<210> SEQ ID NO 260
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 260
ggcatcaagc tcttccctgg cc                                            22

<210> SEQ ID NO 261
<211> LENGTH: 17
<212> TYPE: DNA
<213> ORGANISM: Artificial Sequence
```

```
<220> FEATURE:
<223> OTHER INFORMATION: Synthetic nucleic acid sequence

<400> SEQUENCE: 261
gaatgttacc tctcctg                                                  17

<210> SEQ ID NO 262
<211> LENGTH: 18
<212> TYPE: DNA
<213> ORGANISM: Artificial Sequence
<220> FEATURE:
<223> OTHER INFORMATION: Synthetic nucleic acid sequence

<400> SEQUENCE: 262
gaatgttacc tctcctga                                                 18

<210> SEQ ID NO 263
<211> LENGTH: 19
<212> TYPE: DNA
<213> ORGANISM: Artificial Sequence
<220> FEATURE:
<223> OTHER INFORMATION: Synthetic nucleic acid sequence

<400> SEQUENCE: 263
gcactcagag cgcaagaag                                                19

<210> SEQ ID NO 264
<211> LENGTH: 20
<212> TYPE: DNA
<213> ORGANISM: Artificial Sequence
<220> FEATURE:
<223> OTHER INFORMATION: Synthetic nucleic acid sequence

<400> SEQUENCE: 264
gcactcagag cgcaagaagc                                               20

<210> SEQ ID NO 265
<211> LENGTH: 21
<212> TYPE: DNA
<213> ORGANISM: Artificial Sequence
<220> FEATURE:
<223> OTHER INFORMATION: Synthetic nucleic acid sequence

<400> SEQUENCE: 265
gctgctgcag gccccagatg a                                             21

<210> SEQ ID NO 266
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 266
gctgctgcag gccccagatg at                                            22

<210> SEQ ID NO 267
<211> LENGTH: 21
<212> TYPE: DNA
<213> ORGANISM: Artificial Sequence
<220> FEATURE:
<223> OTHER INFORMATION: Synthetic nucleic acid sequence

<400> SEQUENCE: 267
cacaatttgg tgaattatca a                                             21
```

```
<210> SEQ ID NO 268
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 268
cacaatttgg tgaattatca at                                              22

<210> SEQ ID NO 269
<211> LENGTH: 23
<212> TYPE: DNA
<213> ORGANISM: Artificial Sequence
<220> FEATURE:
<223> OTHER INFORMATION: Synthetic nucleic acid sequence

<400> SEQUENCE: 269
ttcttacaac acaaaatcaa atc                                             23

<210> SEQ ID NO 270
<211> LENGTH: 24
<212> TYPE: DNA
<213> ORGANISM: Artificial Sequence
<220> FEATURE:
<223> OTHER INFORMATION: Synthetic nucleic acid sequence

<400> SEQUENCE: 270
ttcttacaac acaaaatcaa atct                                            24

<210> SEQ ID NO 271
<211> LENGTH: 17
<212> TYPE: DNA
<213> ORGANISM: Artificial Sequence
<220> FEATURE:
<223> OTHER INFORMATION: Synthetic nucleic acid sequence

<400> SEQUENCE: 271
tcggcggctg ccctccc                                                    17

<210> SEQ ID NO 272
<211> LENGTH: 18
<212> TYPE: DNA
<213> ORGANISM: Artificial Sequence
<220> FEATURE:
<223> OTHER INFORMATION: Synthetic nucleic acid sequence

<400> SEQUENCE: 272
tcggcggctg ccctccca                                                   18

<210> SEQ ID NO 273
<211> LENGTH: 19
<212> TYPE: DNA
<213> ORGANISM: Artificial Sequence
<220> FEATURE:
<223> OTHER INFORMATION: Synthetic nucleic acid sequence

<400> SEQUENCE: 273
ttcttggttc aggagaggt                                                  19

<210> SEQ ID NO 274
<211> LENGTH: 21
<212> TYPE: DNA
<213> ORGANISM: Artificial Sequence
<220> FEATURE:
<223> OTHER INFORMATION: Synthetic nucleic acid sequence

<400> SEQUENCE: 274
```
gcaatctgct ctatcctctg c                                      21

<210> SEQ ID NO 275
<211> LENGTH: 25
<212> TYPE: DNA
<213> ORGANISM: Artificial Sequence
<220> FEATURE:
<223> OTHER INFORMATION: Synthetic nucleic acid sequence

<400> SEQUENCE: 275
attcaagctt gccaaagtaa tcgga                                  25

<210> SEQ ID NO 276
<211> LENGTH: 21
<212> TYPE: DNA
<213> ORGANISM: Artificial Sequence
<220> FEATURE:
<223> OTHER INFORMATION: Synthetic nucleic acid sequence

<400> SEQUENCE: 276
cataagctga aacttctggg a                                      21

<210> SEQ ID NO 277
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 277
ggaagtgtat cggtgagacc gt                                     22

<210> SEQ ID NO 278
<211> LENGTH: 25
<212> TYPE: DNA
<213> ORGANISM: Artificial Sequence
<220> FEATURE:
<223> OTHER INFORMATION: Synthetic nucleic acid sequence

<400> SEQUENCE: 278
tgacaaatac tggttaatta gcagt                                  25

<210> SEQ ID NO 279
<211> LENGTH: 19
<212> TYPE: DNA
<213> ORGANISM: Artificial Sequence
<220> FEATURE:
<223> OTHER INFORMATION: Synthetic nucleic acid sequence

<400> SEQUENCE: 279
gctcctgagc atggcggga                                         19

<210> SEQ ID NO 280
<211> LENGTH: 24
<212> TYPE: DNA
<213> ORGANISM: Artificial Sequence
<220> FEATURE:
<223> OTHER INFORMATION: Synthetic nucleic acid sequence

<400> SEQUENCE: 280
tacttattta cgcttgaacc tcga                                   24

<210> SEQ ID NO 281
<211> LENGTH: 25
<212> TYPE: DNA
<213> ORGANISM: Artificial Sequence

```
<220> FEATURE:
<223> OTHER INFORMATION: Synthetic nucleic acid sequence

<400> SEQUENCE: 281
cttaattcat aggttgcaat tttgt                                           25

<210> SEQ ID NO 282
<211> LENGTH: 19
<212> TYPE: DNA
<213> ORGANISM: Artificial Sequence
<220> FEATURE:
<223> OTHER INFORMATION: Synthetic nucleic acid sequence

<400> SEQUENCE: 282
acatcaccct cacttactg                                                  19

<210> SEQ ID NO 283
<211> LENGTH: 19
<212> TYPE: DNA
<213> ORGANISM: Artificial Sequence
<220> FEATURE:
<223> OTHER INFORMATION: Synthetic nucleic acid sequence

<400> SEQUENCE: 283
aattgacaga gagctcctg                                                  19

<210> SEQ ID NO 284
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 284
atgagaggct cacagacgtt tc                                              22

<210> SEQ ID NO 285
<211> LENGTH: 23
<212> TYPE: DNA
<213> ORGANISM: Artificial Sequence
<220> FEATURE:
<223> OTHER INFORMATION: Synthetic nucleic acid sequence

<400> SEQUENCE: 285
ggcatcaagc tcttccctgg ctg                                             23

<210> SEQ ID NO 286
<211> LENGTH: 19
<212> TYPE: DNA
<213> ORGANISM: Artificial Sequence
<220> FEATURE:
<223> OTHER INFORMATION: Synthetic nucleic acid sequence

<400> SEQUENCE: 286
gaatgttacc tctcctggc                                                  19

<210> SEQ ID NO 287
<211> LENGTH: 23
<212> TYPE: DNA
<213> ORGANISM: Artificial Sequence
<220> FEATURE:
<223> OTHER INFORMATION: Synthetic nucleic acid sequence

<400> SEQUENCE: 287
gcactcagag cgcaagaagg ggc                                             23
```

```
<210> SEQ ID NO 288
<211> LENGTH: 23
<212> TYPE: DNA
<213> ORGANISM: Artificial Sequence
<220> FEATURE:
<223> OTHER INFORMATION: Synthetic nucleic acid sequence

<400> SEQUENCE: 288
gctgctgcag gccccagatg agc                                              23

<210> SEQ ID NO 289
<211> LENGTH: 23
<212> TYPE: DNA
<213> ORGANISM: Artificial Sequence
<220> FEATURE:
<223> OTHER INFORMATION: Synthetic nucleic acid sequence

<400> SEQUENCE: 289
cacaatttgg tgaattatca aat                                              23

<210> SEQ ID NO 290
<211> LENGTH: 25
<212> TYPE: DNA
<213> ORGANISM: Artificial Sequence
<220> FEATURE:
<223> OTHER INFORMATION: Synthetic nucleic acid sequence

<400> SEQUENCE: 290
ttcttacaac acaaaatcaa atcac                                            25

<210> SEQ ID NO 291
<211> LENGTH: 20
<212> TYPE: DNA
<213> ORGANISM: Artificial Sequence
<220> FEATURE:
<223> OTHER INFORMATION: Synthetic nucleic acid sequence

<400> SEQUENCE: 291
tcggcggctg ccctcccgga                                                  20

<210> SEQ ID NO 292
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 292
acgttggatg aggtagctga agaggcaaac                                       30

<210> SEQ ID NO 293
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 293
acgttggatg gcctatagcc tctaaaacgc                                       30

<210> SEQ ID NO 294
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 294
```
acgttggatg ctttcaattt gtggaggctg        30

<210> SEQ ID NO 295
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 295
acgttggatg tgtgcactca tttgtggacg        30

<210> SEQ ID NO 296
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 296
acgttggatg gtagctctcc aggcatcaac        30

<210> SEQ ID NO 297
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 297
acgttggatg gtacctggtt ccccttttc        30

<210> SEQ ID NO 298
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 298
acgttggatg acaccaggcg tttgatgttg        30

<210> SEQ ID NO 299
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 299
acgttggatg aaaaacgcca acagcatcgg        30

<210> SEQ ID NO 300
<211> LENGTH: 29
<212> TYPE: DNA
<213> ORGANISM: Artificial Sequence
<220> FEATURE:
<223> OTHER INFORMATION: Synthetic nucleic acid sequence

<400> SEQUENCE: 300
acgttggatg aggcggagat gggtgtgtc        29

<210> SEQ ID NO 301
<211> LENGTH: 30
<212> TYPE: DNA
<213> ORGANISM: Artificial Sequence

```
<220> FEATURE:
<223> OTHER INFORMATION: Synthetic nucleic acid sequence

<400> SEQUENCE: 301
acgttggatg agtctagggt ggggtatgtg                                          30

<210> SEQ ID NO 302
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 302
acgttggatg atgtgtggat tcacagctcg                                          30

<210> SEQ ID NO 303
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 303
acgttggatg gggttggcaa ctctaaaagg                                          30

<210> SEQ ID NO 304
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 304
acgttggatg ctctgaaatc agtgctgctc                                          30

<210> SEQ ID NO 305
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 305
acgttggatg atggtcaaca gtgttgccag                                          30

<210> SEQ ID NO 306
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 306
acgttggatg cacctcttga ttgctttccc                                          30

<210> SEQ ID NO 307
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 307
acgttggatg acccggcctt cctgatcatg                                          30
```

```
<210> SEQ ID NO 308
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 308
acgttggatg attccatgga ggctggatag                                    30

<210> SEQ ID NO 309
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 309
acgttggatg gacaacacta ctaaggcttc                                    30

<210> SEQ ID NO 310
<211> LENGTH: 17
<212> TYPE: DNA
<213> ORGANISM: Artificial Sequence
<220> FEATURE:
<223> OTHER INFORMATION: Synthetic nucleic acid sequence

<400> SEQUENCE: 310
aaaaggtttc tcccccc                                                  17

<210> SEQ ID NO 311
<211> LENGTH: 18
<212> TYPE: DNA
<213> ORGANISM: Artificial Sequence
<220> FEATURE:
<223> OTHER INFORMATION: Synthetic nucleic acid sequence

<400> SEQUENCE: 311
aaaaggtttc tccccccc                                                 18

<210> SEQ ID NO 312
<211> LENGTH: 17
<212> TYPE: DNA
<213> ORGANISM: Artificial Sequence
<220> FEATURE:
<223> OTHER INFORMATION: Synthetic nucleic acid sequence

<400> SEQUENCE: 312
aggctgcttc ttggact                                                  17

<210> SEQ ID NO 313
<211> LENGTH: 18
<212> TYPE: DNA
<213> ORGANISM: Artificial Sequence
<220> FEATURE:
<223> OTHER INFORMATION: Synthetic nucleic acid sequence

<400> SEQUENCE: 313
aggctgcttc ttggactc                                                 18

<210> SEQ ID NO 314
<211> LENGTH: 17
<212> TYPE: DNA
<213> ORGANISM: Artificial Sequence
<220> FEATURE:
<223> OTHER INFORMATION: Synthetic nucleic acid sequence

<400> SEQUENCE: 314
```
caaagatggg cgtgatg                                              17

<210> SEQ ID NO 315
<211> LENGTH: 18
<212> TYPE: DNA
<213> ORGANISM: Artificial Sequence
<220> FEATURE:
<223> OTHER INFORMATION: Synthetic nucleic acid sequence

<400> SEQUENCE: 315
caaagatggg cgtgatga                                             18

<210> SEQ ID NO 316
<211> LENGTH: 17
<212> TYPE: DNA
<213> ORGANISM: Artificial Sequence
<220> FEATURE:
<223> OTHER INFORMATION: Synthetic nucleic acid sequence

<400> SEQUENCE: 316
gccagccccg ggacgga                                              17

<210> SEQ ID NO 317
<211> LENGTH: 18
<212> TYPE: DNA
<213> ORGANISM: Artificial Sequence
<220> FEATURE:
<223> OTHER INFORMATION: Synthetic nucleic acid sequence

<400> SEQUENCE: 317
gccagccccg ggacggac                                             18

<210> SEQ ID NO 318
<211> LENGTH: 17
<212> TYPE: DNA
<213> ORGANISM: Artificial Sequence
<220> FEATURE:
<223> OTHER INFORMATION: Synthetic nucleic acid sequence

<400> SEQUENCE: 318
atgggtgtgt ctgccgg                                              17

<210> SEQ ID NO 319
<211> LENGTH: 18
<212> TYPE: DNA
<213> ORGANISM: Artificial Sequence
<220> FEATURE:
<223> OTHER INFORMATION: Synthetic nucleic acid sequence

<400> SEQUENCE: 319
atgggtgtgt ctgccgga                                             18

<210> SEQ ID NO 320
<211> LENGTH: 19
<212> TYPE: DNA
<213> ORGANISM: Artificial Sequence
<220> FEATURE:
<223> OTHER INFORMATION: Synthetic nucleic acid sequence

<400> SEQUENCE: 320
ggctgtaagg aaatctggg                                            19

<210> SEQ ID NO 321
<211> LENGTH: 20
<212> TYPE: DNA
<213> ORGANISM: Artificial Sequence

```
<220> FEATURE:
<223> OTHER INFORMATION: Synthetic nucleic acid sequence

<400> SEQUENCE: 321
ggctgtaagg aaatctggga                                              20

<210> SEQ ID NO 322
<211> LENGTH: 20
<212> TYPE: DNA
<213> ORGANISM: Artificial Sequence
<220> FEATURE:
<223> OTHER INFORMATION: Synthetic nucleic acid sequence

<400> SEQUENCE: 322
ccttatcctc ctcctgggaa                                              20

<210> SEQ ID NO 323
<211> LENGTH: 21
<212> TYPE: DNA
<213> ORGANISM: Artificial Sequence
<220> FEATURE:
<223> OTHER INFORMATION: Synthetic nucleic acid sequence

<400> SEQUENCE: 323
ccttatcctc ctcctgggaa a                                            21

<210> SEQ ID NO 324
<211> LENGTH: 20
<212> TYPE: DNA
<213> ORGANISM: Artificial Sequence
<220> FEATURE:
<223> OTHER INFORMATION: Synthetic nucleic acid sequence

<400> SEQUENCE: 324
tgtttcattt ctataggcga                                              20

<210> SEQ ID NO 325
<211> LENGTH: 21
<212> TYPE: DNA
<213> ORGANISM: Artificial Sequence
<220> FEATURE:
<223> OTHER INFORMATION: Synthetic nucleic acid sequence

<400> SEQUENCE: 325
tgtttcattt ctataggcga t                                            21

<210> SEQ ID NO 326
<211> LENGTH: 17
<212> TYPE: DNA
<213> ORGANISM: Artificial Sequence
<220> FEATURE:
<223> OTHER INFORMATION: Synthetic nucleic acid sequence

<400> SEQUENCE: 326
cctatcccta cttcccc                                                 17

<210> SEQ ID NO 327
<211> LENGTH: 18
<212> TYPE: DNA
<213> ORGANISM: Artificial Sequence
<220> FEATURE:
<223> OTHER INFORMATION: Synthetic nucleic acid sequence

<400> SEQUENCE: 327
cctatcccta cttccccc                                                18
```

```
<210> SEQ ID NO 328
<211> LENGTH: 19
<212> TYPE: DNA
<213> ORGANISM: Artificial Sequence
<220> FEATURE:
<223> OTHER INFORMATION: Synthetic nucleic acid sequence

<400> SEQUENCE: 328
aaaaggtttc tcccccga                                          19

<210> SEQ ID NO 329
<211> LENGTH: 19
<212> TYPE: DNA
<213> ORGANISM: Artificial Sequence
<220> FEATURE:
<223> OTHER INFORMATION: Synthetic nucleic acid sequence

<400> SEQUENCE: 329
aggctgcttc ttggactga                                         19

<210> SEQ ID NO 330
<211> LENGTH: 19
<212> TYPE: DNA
<213> ORGANISM: Artificial Sequence
<220> FEATURE:
<223> OTHER INFORMATION: Synthetic nucleic acid sequence

<400> SEQUENCE: 330
caaagatggg cgtgatggc                                         19

<210> SEQ ID NO 331
<211> LENGTH: 19
<212> TYPE: DNA
<213> ORGANISM: Artificial Sequence
<220> FEATURE:
<223> OTHER INFORMATION: Synthetic nucleic acid sequence

<400> SEQUENCE: 331
gccagccccg ggacggagt                                         19

<210> SEQ ID NO 332
<211> LENGTH: 19
<212> TYPE: DNA
<213> ORGANISM: Artificial Sequence
<220> FEATURE:
<223> OTHER INFORMATION: Synthetic nucleic acid sequence

<400> SEQUENCE: 332
atgggtgtgt ctgccgggt                                         19

<210> SEQ ID NO 333
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 333
ggctgtaagg aaatctgggg gt                                     22

<210> SEQ ID NO 334
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 334
```

```
ccttatcctc ctcctgggaa ga                                              22

<210> SEQ ID NO 335
<211> LENGTH: 23
<212> TYPE: DNA
<213> ORGANISM: Artificial Sequence
<220> FEATURE:
<223> OTHER INFORMATION: Synthetic nucleic acid sequence

<400> SEQUENCE: 335
tgtttcattt ctataggcga gga                                             23

<210> SEQ ID NO 336
<211> LENGTH: 20
<212> TYPE: DNA
<213> ORGANISM: Artificial Sequence
<220> FEATURE:
<223> OTHER INFORMATION: Synthetic nucleic acid sequence

<400> SEQUENCE: 336 cctatccta cttccccttc                                                  20
```

METHODS OF ANALYSIS OF POLYMORPHISMS AND USES THEREOF

RELATED APPLICATIONS

This application claims priority to New Zealand Application Nos. 540249, filed May 20, 2005 and 541842, filed Aug. 15, 2005, both of which are incorporated by reference in their entireties.

FIELD OF THE INVENTION

The present invention is concerned with methods for the assessment of diseases that result from the combined or interactive effects of two or more genetic variants, and in particular for diagnosing risk of developing such diseases in subjects using an analysis of genetic polymorphisms.

BACKGROUND OF THE INVENTION

Diseases that result from the combined or interactive effects of two or more genetic variants, with or without environmental factors, are called complex diseases and include cancer, coronary artery disease, diabetes, stroke, and chronic obstructive pulmonary disease (COPD). Although combining non-genetic risk factors to determine a risk level of outcome has been in applied to coronary artery disease, (by combining individual factors such as blood pressure, gender, fasting cholesterol, and smoking status), there are no such methods in combining the effects of multiple genetic factors with non-genetic factors. There is a growing realization that the complex diseases, for which examples are given above, may result from the combined effects of common genetic variants or polymorphisms rather than mutations which are rare (believed to be present in less than 1% of the general population). Moreover, these relatively common polymorphisms can confer either susceptibility and/or protective effects on the development of these diseases. In addition, the likelihood that these polymorphisms are actually expressed (termed penetrance) as a disease or clinical manifestation requires a quantum of environmental exposure before such a genetic tendency can be clinically detected.

SUMMARY OF THE INVENTION

Recent studies have identified a number of genetic variants or polymorphisms that confer susceptibility to protection from COPD, occupational COPD (OCOPD), and lung cancer. The biological basis of just how these polymorphisms interact or combine to determine risk remains unclear.

Surprisingly, it has now been found that an assessment approach which determines a subject's net score following the balancing of the number of polymorphisms associated with protection from a disease against the number of polymorphisms associated with susceptibility to that disease present in the subject is indicative of that subject's risk quotient. Furthermore, it has presently been determined that this approach is widely applicable, on a disease-by-disease basis.

It is broadly to this approach to risk assessment that the present invention is directed.

Accordingly, in a first aspect, the present invention provides a method of assessing a subject's risk of developing a disease which includes:

analyzing a biological sample from said subject for the presence or absence of protective polymorphisms and for the presence or absence of susceptibility polymorphisms, wherein said protective and susceptibility polymorphisms are associated with said disease;

assigning a positive score for each protective polymorphism and a negative score for each susceptibility polymorphism or vice versa;

calculating a net score for said subject, said net score representing the balance between the combined value of the protective polymorphisms and the combined value of the susceptibility polymorphisms present in the subject sample;

wherein a net protective score is predictive of a reduced risk of developing said disease and a net susceptibility score is predictive of an increased risk of developing said disease.

The value assigned to each protective polymorphism can be the same or can be different. The value assigned to each susceptibility polymorphism can be the same or can be different, with either each protective polymorphism having a negative value and each susceptibility polymorphism having a positive value, or vice versa. When the disease is a lung disease, the protective polymorphisms analyzed can be selected from one or more of the group consisting of: +760GG or +760CG within the gene encoding superoxide dismutase 3 (SOD3); −1296TT within the promoter of the gene encoding tissue inhibitor of metalloproteinase 3 (TIMP3); CC (homozygous P allele) within codon 10 of the gene encoding transforming growth factor beta (TGFβ); 2G2G within the promoter of the gene encoding metalloproteinase 1 (MMP1); or one or more polymorphisms in linkage disequilibrium with one or more of these polymorphisms.

Linkage disequilibrium is a phenomenon in genetics whereby two or more mutations or polymorphisms are in such close genetic proximity that they are co-inherited. This means that in genotyping, detection of one polymorphism as present implies the presence of the other. (Reich, D. E. et al. Linkage disequilibrium in the human genome. *Nature* 411:199-204 (2001), herein incorporated by reference in its entirety).

Preferably, all polymorphisms of the group are analyzed.

Preferably, the susceptibility polymorphisms analyzed are selected from one or more of the group consisting of: −82AA within the promoter of the gene encoding human macrophage elastase (MMP12); −1562CT or −1562TT within the promoter of the gene encoding metalloproteinase 9 (MMP9); 1237AG or 1237AA (Tt or tt allele genotypes) within the 3' region of the gene encoding α1-antitrypsin (α1AT); or one or more polymorphisms in linkage disequilibrium with one or more of these polymorphisms.

Preferably, all polymorphisms of the group are analyzed.

In one embodiment each protective polymorphism is assigned a value of −1 and each susceptibility polymorphism is assigned a value of +1.

In another embodiment each protective polymorphism is assigned a value of +1 and each susceptibility polymorphism is assigned a value of −1.

When the disease is COPD, the protective polymorphisms analyzed can be selected from one or more of the group consisting of: −765 CC or CG in the promoter of the gene encoding cyclooxygenase 2 (COX2); Arg 130 Gln AA in the gene encoding Interleukin-13 (IL-13); Asp 298 Glu TT in the gene encoding nitric oxide synthase 3 (NOS3); Lys 420 Thr AA or AC in the gene encoding vitamin binding protein (VDBP); Glu 416 Asp TT or TG in the gene encoding VDBP; Ile 105 Val AA in the gene encoding glutathione S-transferase (GSTP1); MS in the gene encoding α1-antitrypsin (α1AT); the +489 GG genotype in the gene encoding Tumor Necrosis factor α (TNFα); the −308 GG genotype in the gene encoding TNFα; the C89Y AA or AG genotype in the gene encoding SMAD3; the 161 GG genotype in the gene encoding Mannose binding lectin 2 (MBL2); the −1903 AA genotype in the gene encoding Chymase 1 (CMA1); the Arg 197 Gln AA genotype in the gene encoding N-Acetyl transferase 2 (NAT2); the His 139 Arg GG genotype in the gene encoding Microsomal epoxide hydrolase (MEH); the −366 AA or AG genotype in the gene encoding 5 Lipo-oxygenase (ALOX5); the HOM T2437C TT genotype in the gene encoding Heat Shock Protein 70 (HSP 70); the exon 1 +49 CT or TT genotype in the gene encoding Elafin; the Gln 27 Glu GG genotype in the gene encoding β2 Adrenergic receptor (ADBR); the −1607 1G1G or 1G2G genotype in the promoter of the gene encoding Matrix Metalloproteinase 1 (MMP1); or one or more polymorphisms in linkage disequilibrium with one or more of these polymorphisms. Preferably, all polymorphisms of the group are analysed.

Preferably, the susceptibility polymorphisms analysed are selected from one or more of the group consisting of: Arg 16 Gly GG in the gene encoding β2-adrenoreceptor (ADRB2); 105 AA in the gene encoding Interleukin-18 (IL-18); −133 CC in the promoter of the gene encoding IL-18; −675 5G5G in the promoter of the gene encoding plasminogen activator inhibitor 1 (PAI-1); −1055 TT in the promoter of the gene encoding IL-13; 874 TT in the gene encoding interferon gamma (IFN?); the +489 AA or AG genotype in the gene encoding TNFa; the −308 AA or AG genotype in the gene encoding TNFa; the C89Y GG genotype in the gene encoding SMAD3; the E469K GG genotype in the gene encoding Intracellular Adhesion molecule 1 (ICAM1); the Gly 881 Arg GC or CC genotype in the gene encoding Caspase (NOD2); the −511 GG genotype in the gene encoding IL1B; the Tyr 113 His TT genotype in the gene encoding MEH; the −366 GG genotype in the gene encoding ALOX5; the HOM T2437C CC or CT genotype in the gene encoding HSP 70; the +13924 AA genotype in the gene encoding Chloride Channel Calcium-activated 1 (CLCA1); the −159 CC genotype in the gene encoding Monocyte differentiation antigen CD-14 (CD-14); or one or more polymorphisms in linkage disequilibrium with one or more of these polymorphisms.

Preferably, all polymorphisms of the group are analysed.

In one embodiment each protective polymorphism is assigned a value of −1 and each susceptibility polymorphism is assigned a value of +1.

In one embodiment each protective polymorphism is assigned a value of +1 and each susceptibility polymorphism is assigned a value of −1.

When the disease is OCOPD, the protective polymorphisms analysed can be selected from one or more of the group consisting of: −765 CC or CG in the promoter of the gene encoding COX2; −251 AA In the promoter of the gene encoding interleukin-8 (IL-8); Lys 420 Thr AA in the gene encoding VDBP; Glu 416 Asp TT or TG in the gene encoding VDBP; exon 3 T/C RR in the gene encoding microsomal epoxide hydrolase (MEH); Arg 312 Gln AG or GG in the gene encoding SOD3; MS or SS in the gene encoding a1AT; Asp 299 Gly AG or GG in the gene encoding toll-like receptor 4 (TLR4); Gln 27 Glu CC in the gene encoding ADRB2; −518 AA in the gene encoding IL-11; Asp 298 Glu TT in the gene encoding NOS3; or one or more polymorphisms in linkage disequilibrium with one or more of these polymorphisms.

Preferably, all polymorphisms of the group are analysed.

Preferably, the susceptibility polymorphisms analysed are selected from one or more of the group consisting of: −765 GG in the promoter of the gene encoding COX2; 105 AA in the gene encoding IL-18; −133 CC in the promoter of the gene encoding IL-18; −675 5G5G in the promoter of the gene encoding PAI-1; Lys 420 Thr CC in the gene encoding VDBP; Glu 416 Asp GG in the gene encoding VDBP; Ile 105 Val GG in the gene encoding GSTP1; Arg 312 Gln AA in the gene encoding SOD3; −1055 TT in the promoter of the gene encoding IL-13; 3'1237 Tt or tt in the gene encoding a1AT; −1607 2G2G in the promoter of the gene encoding MMP1; or one or more polymorphisms in linkage disequilibrium with one or more of these polymorphisms.

Preferably, all polymorphisms of the group are analysed.

In one embodiment each protective polymorphism is assigned a value of −1 and each susceptibility polymorphism is assigned a value of +1.

In one embodiment each protective polymorphism is assigned a value of +1 and each susceptibility polymorphism is assigned a value of −1.

When the disease is lung cancer, the protective polymorphisms analysed can be selected from one or more of the group consisting of: the Asp 298 Glu TT genotype in the gene encoding NOS3; the Arg 312 Gln CG or GG genotype in the gene encoding SOD3; the Asn 357 Ser AG or GG genotype in the gene encoding MMP12; the 105 AC or CC genotype in the gene encoding IL-18; the −133 CG or GG genotype in the gene encoding IL-18; the −765 CC or CG genotype in the promoter of the gene encoding COX2; the −221 TT genotype in the gene encoding Mucin 5AC (MUC5AC); the intron 1 C/T TT genotype in the gene encoding Arginase 1 (Arg1); the Leu252Val GG genotype in the gene encoding Insulin-like growth factor II receptor (IGF2R); the −1082 GG genotype in the gene encoding Interleukin 10 (IL-10); the −251 AA genotype in the gene encoding Interleukin 8 (IL-8); the Arg 399 Gln AA genotype in the X-ray repair complementing defective in Chinese hamster 1 (XRCC1) gene; the A870G GG genotype in the gene encoding cyclin D (CCND1); the −751 GG genotype in the promoter of the xeroderma pigmentosum complementation group D (XPD) gene; the Ile 462 Val AG or GG genotype in the gene encoding cytochrome P450 1A1 (CYP1A1); the Ser 326 Cys GG genotype in the gene encoding 8-Oxoguanine DNA glycolase (OGG1); the Phe 257 Ser CC genotype in the gene encoding REV1; or one or more polymorphisms in linkage disequilibrium with any one or more of these polymorphisms.

Preferably, all polymorphisms of the group are analysed.

Preferably, the susceptibility polymorphisms analysed are selected from one or more of the group consisting of: the −786 TT genotype in the promoter of the gene encoding NOS3; the Ala 15 Thr GG genotype in the gene encoding anti-chymotrypsin (ACT); the 105 AA genotype in the gene encoding IL-18; the −133 CC genotype in the promoter of the gene encoding IL-18; the 874 AA genotype in the gene encoding IFN?; the −765 GG genotype in the promoter of the gene encoding COX2; the −447 CC or GC genotype in the gene encoding Connective tissue growth factor (CTGF); and the +161 AA or AG genotype in the gene encoding MBL2; −511 GG genotype in the gene encoding IL-1B; the A-670G AA genotype in the gene encoding FAS (Apo-1/CD95); the Arg 197 Gln GG genotype in the gene encoding N-acetyltransferase 2 (NAT2); the Ile462 Val AA genotype in the gene encoding CYP1A1; the 1019 G/C Pst I CC or CG genotype in the gene encoding cytochrome P450 2E1 (CYP2E1); the C/T Rsa I TT or TC genotype in the gene encoding CYP2E1; the GSTM null genotype in the gene encoding GSTM; the −1607 2G/2G genotype in the promoter of the gene encoding MMP1; the Gln 185 Glu CC genotype in the gene encoding Nibrin (NBS1); the Asp 148 Glu GG genotype in the gene encoding Apex nuclease (APE1); or one or more polymorphisms in linkage disequilibrium with any one or more of these polymorphisms.

Preferably, all polymorphisms of the group are analysed.

In one embodiment each protective polymorphism is assigned a value of −1 and each susceptibility polymorphism is assigned a value of +1.

In one embodiment each protective polymorphism is assigned a value of +1 and each susceptibility polymorphism is assigned a value of −1.

In various embodiments the subject is or has been a smoker.

Preferably, the methods of the invention are performed in conjunction with an analysis of one or more risk factors, including one or more epidemiological risk factors, associated with the risk of developing a lung disease including COPD, emphysema, OCOPD, and lung cancer. Such epidemiological risk factors include but are not limited to smoking or exposure to tobacco smoke, age, sex, and familial history.

In another aspect, the invention provides a method of determining a subject's risk of developing a disease, said method comprising obtaining the result of one or more analyses of a sample from said subject to determine the presence or absence of protective polymorphisms and the presence or absence of susceptibility polymorphisms, and wherein said protective and susceptibility polymorphisms are associated with said disease;

assigning a positive score for each protective polymorphism and a negative score for each susceptibility polymorphism or vice versa;

calculating a net score for said subject, said net score representing the balance between the combined value of the protective polymorphisms and the combined value of the susceptibility polymorphisms present in the subject sample;

wherein a net protective score is predictive of a reduced risk of developing said disease and a net susceptibility score is predictive of an increased risk of developing said disease.

In a further aspect the present invention provides a method for assessing the risk of a subject developing a disease which includes determining a net score for said subject in accordance with the methods of the invention described above, in combination with a score based on the presence or absence of one or more epidemiological risk factors, wherein a net protective score is predictive of a reduced risk of developing said disease and a net susceptibility score is predictive of an increased predisposition and/or susceptibility to said disease.

In another aspect, the present invention provides a kit for assessing a subject's risk of developing a disease, said kit comprising a means of analyzing a sample from said subject for the presence or absence of one or more protective polymorphisms and one or more susceptibility polymorphisms as described herein.

In yet a further aspect, the present invention provides a method of prophylactic or therapeutic intervention in relation to a subject having a net susceptibility score for a disease as determined by a method as defined above which includes the steps of communicating to said subject said net susceptibility score, and advising on changes to the subject's lifestyle that could reduce the risk of developing said disease.

In still a further aspect, the present invention provides a method of treatment of a subject to decrease to the risk of developing a disease through alteration of the net score for said subject as determined by a method as defined above, wherein said method of treatment includes reversing, genotypically or phenotypically, the presence and/or functional effect of one or more susceptibility polymorphisms associated with said disease; and/or replicating and/or mimicking, genotypically or phenotypically, the presence and/or functional effect of one or more protective polymorphisms associated with said disease.

DESCRIPTION OF THE PREFERRED EMBODIMENTS

Figure 1:
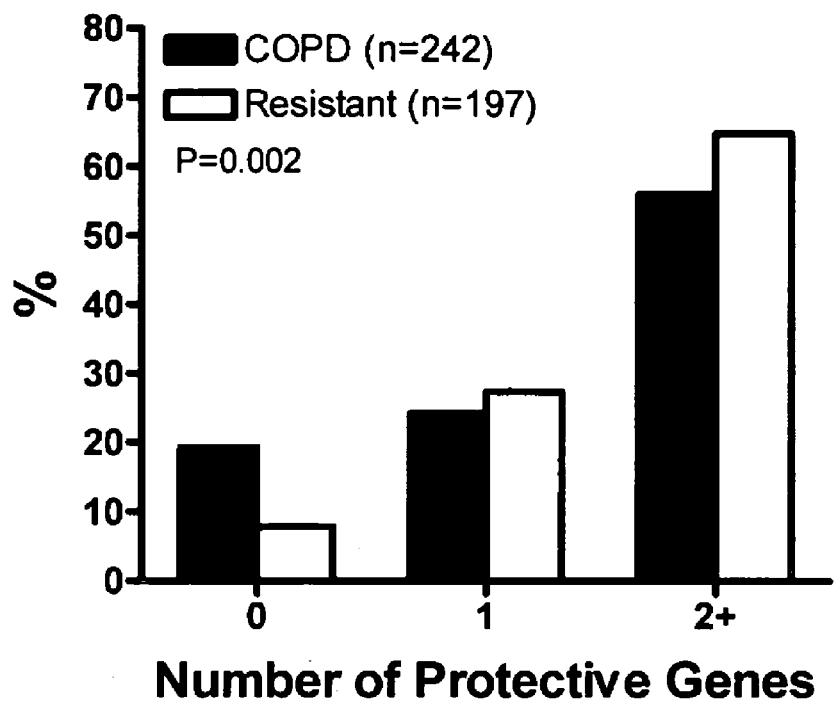
FIG. 1: depicts a graph showing combined frequencies of the presence or absence of selected protective genotypes in the COPD subjects and in resistant smokers.

There is a need for a method for assessing a subject's risk of developing a disease using genetic (and optionally non-genetic) risk factors. In some embodiments, it is an object of the present invention to go some way towards meeting this need and/or to provide the public with a useful choice.

The present invention is directed to methods for the assessment of the genetic risk quotient of a particular subject with respect to a particular disease. The methods rely upon the recognition that for many (if not all) diseases there exist genetic polymorphisms which fall into two categories— namely those indicative of a reduced risk of developing a particular disease (which can be termed "protective polymorphisms" or "protective SNPs") and those indicative of an increased risk of developing a particular disease (which can be termed "susceptibility polymorphisms" or "susceptibility SNPs").

As used herein, the phrase "risk of developing [a] disease" means the likelihood that a subject to whom the risk applies will develop the disease, and includes predisposition to, and potential onset of the disease. Accordingly, the phrase "increased risk of developing [a] disease" means that a subject having such an increased risk possesses an hereditary inclination or tendency to develop the disease. This does not mean that such a person will actually develop the disease at any time, merely that he or she has a greater likelihood of developing the disease compared to the general population of individuals that either does not possess a polymorphism associated with increased disease risk, or does possess a polymorphism associated with decreased disease risk. Subjects with an increased risk of developing the disease include those with a predisposition to the disease, for example in the case of COPD, a tendency or predilection regardless of their lung function at the time of assessment, for example, a subject who is genetically inclined to COPD but who has normal lung function, those at potential risk, for example in the case of COPD, subjects with a tendency to mildly reduced lung function who are likely to go on to suffer COPD if they keep smoking, and subjects with potential onset of the disease, for example in the case of COPD, subjects who have a tendency to poor lung function on spirometry etc., consistent with COPD at the time of assessment.

Similarly, the phrase "decreased risk of developing [a] disease" means that a subject having such a decreased risk possesses an hereditary disinclination or reduced tendency to develop the disease. This does not mean that such a person will not develop the disease at any time, merely that he or she has a decreased likelihood of developing the disease compared to the general population of individuals that either does possess one or more polymorphisms associated with increased disease risk, or does not possess a polymorphism associated with decreased disease risk.

It will be understood that in the context of the present invention the term "polymorphism" means the occurrence together in the same population at a rate greater than that attributable to random mutation (usually greater than 1%) of two or more alternate forms (such as alleles or genetic markers) of a chromosomal locus that differ in nucleotide sequence or have variable numbers of repeated nucleotide units. See www<dot>ornl<dot>gov/sci/techresources/Human_Genome/publicat/97pr/09gloss<dot>html#p. Accordingly, the term "polymorphisms" is used herein contemplates genetic variations, including single nucleotide substitutions, insertions and deletions of nucleotides, repetitive sequences (such as microsatellites), and the total or partial absence of genes (eg. null mutations). As used herein, the term "polymorphisms" also includes genotypes and haplotypes. A genotype is the genetic composition at a specific locus or set of loci. A haplotype is a set of closely linked genetic markers present on one chromosome which are not easily separable by recombination, tend to be inherited together, and can be in linkage disequilibrium. A haplotype can be identified by patterns of polymorphisms such as SNPs. Similarly, the term "single nucleotide polymorphism" or "SNP" in the context of the present invention includes single base nucleotide substitutions and short deletion and insertion polymorphisms. It will further be understood that the term "disease" is used herein in its widest possible sense, and includes conditions which can be considered disorders and/or illnesses which have a genetic basis or to which the genetic makeup of the subject contributes.

Using case-control studies, the frequencies of several genetic variants (polymorphisms) of candidate genes have been compared in disease sufferers, for example, in chronic obstructive pulmonary disease (COPD) sufferers, in occupational chronic obstructive pulmonary disease (OCOPD) sufferers, and in lung cancer sufferers, and in control subjects not suffering from the relevant disease, for example smokers without lung cancer and with normal lung function. The majority of these candidate genes have confirmed (or likely) functional effects on gene expression or protein function.

In various specific embodiments, the frequencies of polymorphisms between blood donor controls, resistant subjects and those with COPD, the frequencies of polymorphisms between blood donor controls, resistant subjects and those with OCOPD, and the frequencies of polymorphisms between blood donor controls, resistant subjects and those with lung cancer, have been compared. This has resulted in both protective and susceptibility polymorphisms being identified for each disease.

The surprising finding relevant to this invention is that a combined analysis of protective and susceptibility polymorphisms discriminatory for a given disease yields a result that is indicative of that subject's risk quotient for that disease. This approach is widely applicable, on a disease-by-disease basis.

The present invention identifies methods of assessing the risk of a subject developing a disease which includes determining in said subject the presence or absence of protective and susceptibility polymorphisms associated with said disease. A net score for said subject is derived, said score representing the balance between the combined value of the protective polymorphisms present in said subject and the combined value of the susceptibility polymorphisms present in said subject. A net protective score is predictive of a reduced risk of developing said disease, and a net susceptibility score is predictive of an increased risk of developing said disease.

Within each category (protective polymorphisms, susceptibility polymorphisms, respectively) the polymorphisms can each be assigned the same value. For example, in the analyses presented in the Examples herein, each protective polymorphism associated with a given disease is assigned a value of +1, and each susceptibility polymorphism is assigned a value of −1. Alternatively, polymorphisms discriminatory for a disease within the same category can each be assigned a different value to reflect their discriminatory value for said disease. For example, a polymorphism highly discriminatory of risk of developing a disease can be assigned a high weighting, for example a polymorphism with a high Odd's ratio can be considered highly discriminatory of disease, and can be assigned a high weighting.

Accordingly, in a first aspect, the present invention provides a method of assessing a subject's risk of developing a disease which includes:

analyzing a biological sample from said subject for the presence or absence of protective polymorphisms and for the presence or absence of susceptibility polymorphisms, wherein said protective and susceptibility polymorphisms are associated with said disease;

assigning a positive score for each protective polymorphism and a negative score for each susceptibility polymorphism or vice versa;

calculating a net score for said subject, said net score representing the balance between the combined value of the protective polymorphisms and the combined value of the susceptibility polymorphisms present in the subject sample;

wherein a net protective score is predictive of a reduced risk of developing said disease and a net susceptibility score is predictive of an increased risk of developing said disease.

The subject sample can have already been analysed for the presence or absence of one or more protective or susceptibility polymorphisms, and the method includes the steps of assigning a positive score for each protective polymorphism and a negative score for each susceptibility polymorphism or vice versa;

calculating a net score for said subject, said net score representing the balance between the combined value of the protective polymorphisms and the combined value of the susceptibility polymorphisms present in the subject sample;

wherein a net protective score is predictive of a reduced risk of developing said disease and a net susceptibility score is predictive of an increased risk of developing said disease.

In one embodiment described herein in Example 1, 17 susceptibility genetic polymorphisms and 19 protective genetic polymorphisms identified as discriminatory for COPD were analysed using methods of the invention. These analyses can be used to determine the risk quotient of any subject for COPD, and in particular to identify subjects at greater risk of developing lung cancer.

In another embodiment described herein in Example 2, 11 susceptibility genetic polymorphisms and 11 protective genetic polymorphisms identified as discriminatory for OCOPD are analysed using methods of the invention. These analyses can be used to determine the risk quotient of any subject for OCOPD, and in particular to identify subjects at greater risk of developing OCOPD.

In a further embodiment described herein in Example 3, 19 susceptibility genetic polymorphisms and 17 protective genetic polymorphisms identified as discriminatory for lung cancer are analysed using methods of the invention. These analyses can be used to determine the risk quotient of any subject for lung cancer, and in particular to identify subjects at greater risk of developing lung cancer.

Susceptibility and protective polymorphisms can readily be identified for other diseases using approaches similar to those described in the Examples, as well as in PCT International Application No. PCT/NZ02/00106 (published as WO 02/099134 and herein incorporated by reference in its entirety) via which four susceptibility and three protective polymorphisms discriminatory for lung disease were identified.

The one or more polymorphisms can be detected directly or by detection of one or more polymorphisms which are in linkage disequilibrium with said one or more polymorphisms. As discussed above, linkage disequilibrium is a phenomenon in genetics whereby two or more mutations or polymorphisms are in such close genetic proximity that they are co-inherited. This means that in genotyping, detection of one polymorphism as present implies the presence of the other. (Reich D E et al; Linkage disequilibrium in the human genome, Nature 2001, 411:199-204.)

Examples of polymorphisms reported to be in linkage disequilibrium are presented herein, and include the Interleukin-18 −133 C/G and 105 A/C polymorphisms, and the Vitamin D binding protein Glu 416 Asp and Lys 420 Thr polymorphisms, as shown below.

| Gene | SNPs | rs numbers | Alleles in LD | LD between alleles | Phenotype in COPD |
|---|---|---|---|---|---|
| Interleukin-18 | IL18 −133 C/G | rs360721 | C allele | Strong LD | CC susceptible |
| | IL18 105 A/C | rs549908 | A allele | | AA susceptible |
| Vitamin D binding protein | VDBP Lys 420 Thr | rs4588 | A allele | Strong LD | AA/AC protective |
| | VDBP Glu 416 Asp | rs7041 | T allele | | TT/TG protective |

It will be apparent that polymorphisms in linkage disequilibrium with one or more other polymorphism associated with increased or decreased risk of developing COPD, emphysema, or both COPD and emphysema will also provide utility as biomarkers for risk of developing COPD, emphysema, or both COPD and emphysema. The data presented herein shows that the frequency for SNPs in linkage disequilibrium is very similar. Accordingly, these genetically linked SNPs can be utilized in combined polymorphism analyses to derive a level of risk comparable to that calculated from the original SNP.

It will therefore be apparent that one or more polymorphisms in linkage disequilibrium with the polymorphisms specified herein can be identified, for example, using public data bases. Examples of such polymorphisms reported to be in linkage disequilibrium with the polymorphisms specified herein are presented herein in Table 21.

The methods of the invention are primarily reliant on genetic information such as that derived from methods suitable to the detection and identification of single nucleotide polymorphisms (SNPs) associated with the specific disease for which a risk assessment is desired. In some embodiments, a SNP is a single base change or point mutation resulting in genetic variation between individuals. SNPs occur in the human genome approximately once every 100 to 300 bases, and can occur in coding or non-coding regions. Due to the redundancy of the genetic code, a SNP in the coding region may or may not change the amino acid sequence of a protein product. A SNP in a non-coding region can, for example, alter gene expression by, for example, modifying control regions such as promoters, transcription factor binding sites, processing sites, ribosomal binding sites, and affect gene transcription, processing, and translation.

SNPs can facilitate large-scale association genetics studies, and there has recently been great interest in SNP discovery and detection. SNPs show great promise as markers for a number of phenotypic traits (including latent traits), such as for example, disease propensity and severity, wellness propensity, and drug responsiveness including, for example, susceptibility to adverse drug reactions. Knowledge of the association of a particular SNP with a phenotypic trait, coupled with the knowledge of whether an individual has said particular SNP, can enable the targeting of diagnostic, preventative and therapeutic applications to allow better disease management, to enhance understanding of disease states and to ultimately facilitate the discovery of more effective treatments, such as personalized treatment regimens.

Indeed, a number of databases have been constructed of known SNPs, and for some such SNPs, the biological effect associated with a SNP. For example, the NCBI SNP database "dbSNP" is incorporated into NCBI's Entrez system and can be queried using the same approach as the other Entrez databases such as PubMed and GenBank. This database has records for over 1.5 million SNPs mapped onto the human genome sequence. Each dbSNP entry includes the sequence context of the polymorphism (i.e., the surrounding sequence), the occurrence frequency of the polymorphism (by population or individual), and the experimental method(s), protocols, and conditions used to assay the variation, and can include information associating a SNP with a particular phenotypic trait.

At least in part because of the potential impact on health and wellness, there has been and continues to be a great deal of effort to develop methods that reliably and rapidly identify SNPs. This is no trivial task, at least in part because of the complexity of human genomic DNA, with a haploid genome of $3 \times 10^9$ base pairs, and the associated sensitivity and discriminatory requirements.

Genotyping approaches to detect SNPs well-known in the art include DNA sequencing, methods that require allele specific hybridization of primers or probes, allele specific incorporation of nucleotides to primers bound close to or adjacent to the polymorphisms (often referred to as "single base extension", or "minisequencing"), allele-specific ligation (joining) of oligonucleotides (ligation chain reaction or ligation padlock probes), allele-specific cleavage of oligonucleotides or PCR products by restriction enzymes (restriction fragment length polymorphisms analysis or RFLP) or chemical or other agents, resolution of allele-dependent differences in electrophoretic or chromatographic mobilities, by structure specific enzymes including invasive structure specific enzymes, or mass spectrometry. Analysis of amino acid variation is also possible where the SNP lies in a coding region and results in an amino acid change.

DNA sequencing allows the direct determination and identification of SNPs. The benefits in specificity and accuracy are generally outweighed for screening purposes by the difficulties inherent in whole genome, or even targeted subgenome, sequencing.

Mini-sequencing involves allowing a primer to hybridize to the DNA sequence adjacent to the SNP site on the test sample under investigation. The primer is extended by one nucleotide using all four differentially tagged fluorescent dideoxynucleotides (A,C,G, or T), and a DNA polymerase. Only one of the four nucleotides (homozygous case) or two of the four nucleotides (heterozygous case) is incorporated. The base that is incorporated is complementary to the nucleotide at the SNP position.

A number of methods currently used for SNP detection involve site-specific and/or allele-specific hybridisation (Matsuzaki, H. et al. *Genome Res.* 14:414-425 (2004); Matsuzaki, H. et al. *Nat. Methods* 1:109-111 (2004); Sethi, A. A. et al. *Clin. Chem.* 50(2):443-446 (2004), each of the foregoing which is herein incorporated by reference in its entirety). These methods are largely reliant on the discriminatory binding of oligonucleotides to target sequences containing the SNP of interest. The techniques of Affymetrix (Santa Clara, Calif.) and Nanogen Inc. (San Diego, Calif.) are particularly well-known, and utilize the fact that DNA duplexes containing single base mismatches are much less stable than duplexes that are perfectly base-paired. The presence of a matched duplex is detected by fluorescence.

The majority of methods to detect or identify SNPs by site-specific hybridisation require target amplification by methods such as PCR to increase sensitivity and specificity (see, for example U.S. Pat. No. 5,679,524, PCT publication WO 98/59066, PCT publication WO 95/12607, each of the foregoing which is herein incorporated by reference in its entirety). US Application 20050059030 (incorporated herein in its entirety) describes a method for detecting a single nucleotide polymorphism in total human DNA without prior amplification or complexity reduction to selectively enrich for the target sequence, and without the aid of any enzymatic reaction. The method utilizes a single-step hybridization involving two hybridization events: hybridization of a first portion of the target sequence to a capture probe, and hybridization of a second portion of said target sequence to a detection probe. Both hybridization events happen in the same reaction, and the order in which hybridisation occurs is not critical.

US Application 20050042608 (herein incorporated by reference in its entirety) describes a modification of the method of electrochemical detection of nucleic acid hybridization of Thorp et al. (U.S. Pat. No. 5,871,918, herein incorporated by reference in its entirety). Briefly, capture probes are designed, each of which has a different SNP base and a sequence of probe bases on each side of the SNP base. The probe bases are complementary to the corresponding target sequence adjacent to the SNP site. Each capture probe is immobilized on a different electrode having a non-conductive outer layer on a conductive working surface of a substrate. The extent of hybridization between each capture probe and the nucleic acid target is detected by detecting the oxidation-reduction reaction at each electrode, utilizing a transition metal complex. These differences in the oxidation rates at the different electrodes are used to determine whether the selected nucleic acid target has a single nucleotide polymorphism at the selected SNP site.

The technique of Lynx Therapeutics (Hayward, Calif.) using MEGATYPE™ technology can genotype very large numbers of SNPs simultaneously from small or large pools of genomic material. This technology uses fluorescently labeled probes and compares the collected genomes of two populations, enabling detection and recovery of DNA fragments spanning SNPs that distinguish the two populations, without requiring prior SNP mapping or knowledge.

A number of other methods for detecting and identifying SNPs exist. These include the use of mass spectrometry, for example, to measure probes that hybridize to the SNP (Ross, P. L. et al. Discrimination of single-nucleotide polymorphisms in human DNA using peptide nucleic acid probes detected by MALDI-TOF mass spectrometry. *Anal. Chem.* 69, 4197-4202 (1997), herein incorporated by reference in its entirety). This technique varies in how rapidly it can be performed, from a few samples per day to a high throughput of 40,000 SNPs per day, using mass code tags. A preferred example is the use of mass spectrometric determination of a nucleic acid sequence which includes the polymorphisms of the invention, for example, which includes the promoter of the COX2 gene or a complementary sequence. Such mass spectrometric methods are known to those skilled in the art, and the genotyping methods of the invention are amenable to adaptation for the mass spectrometric detection of the polymorphisms of the invention, for example, the COX2 promoter polymorphisms of the invention.

SNPs can also be determined by ligation-bit analysis. This analysis requires two primers that hybridize to a target with a one nucleotide gap between the primers. Each of the four nucleotides is added to a separate reaction mixture containing DNA polymerase, ligase, target DNA and the primers. The polymerase adds a nucleotide to the 3' end of the first primer that is complementary to the SNP, and the ligase then ligates the two adjacent primers together. Upon heating of the sample, if ligation has occurred, the now larger primer will remain hybridized and a signal, for example, fluorescence, can be detected. A further discussion of these methods can be found in U.S. Pat. Nos. 5,919,626; 5,945,283; 5,242,794; and 5,952,174 (each of the foregoing which is herein incorporated by reference in its entirety).

U.S. Pat. No. 6,821,733 (herein incorporated by reference in its entirety) describes methods to detect differences in the sequence of two nucleic acid molecules that includes the steps of: contacting two nucleic acids under conditions that allow the formation of a four-way complex and branch migration; contacting the four-way complex with a tracer molecule and a detection molecule under conditions in which the detection molecule is capable of binding the tracer molecule or the four-way complex; and determining binding of the tracer molecule to the detection molecule before and after exposure to the four-way complex. Competition of the four-way complex with the tracer molecule for binding to the detection molecule indicates a difference between the two nucleic acids.

Protein— and proteomics-based approaches are also suitable for polymorphism detection and analysis. Polymorphisms which result in or are associated with variation in expressed proteins can be detected directly by analyzing said proteins. This typically requires separation of the various proteins within a sample, by, for example, gel electrophoresis or HPLC, and identification of said proteins or peptides derived therefrom, for example by NMR or protein sequencing such as chemical sequencing or more prevalently mass spectrometry. Proteomic methodologies are well known in the art, and have great potential for automation. For example, integrated systems, such as the ProteomIQ™ system from Proteome Systems, provide high throughput platforms for proteome analysis combining sample preparation, protein separation, image acquisition and analysis, protein processing, mass spectrometry and bioinformatics technologies.

The majority of proteomic methods of protein identification utilize mass spectrometry, including ion trap mass spectrometry, liquid chromatography (LC) and LC/MSn mass spectrometry, gas chromatography (GC) mass spectroscopy, Fourier transform-ion cyclotron resonance-mass spectrometer (FT-MS), MALDI-TOF mass spectrometry, and ESI mass spectrometry, and their derivatives. Mass spectrometric methods are also useful in the determination of post-translational modification of proteins, such as phosphorylation or glycosylation, and thus have utility in determining polymorphisms that result in or are associated with variation in post-translational modifications of proteins.

Associated technologies are also well known, and include, for example, protein processing devices such as the "Chemical Inkjet Printer" comprising piezoelectric printing technology that allows in situ enzymatic or chemical digestion of protein samples electroblotted from 2-D PAGE gels to membranes by jetting the enzyme or chemical directly onto the selected protein spots (Sloane, A. J. et al. High throughput peptide mass fingerprinting and protein macroarray analysis using chemical printing strategies. *Mol Cell Proteomics* 1(7): 490-9 (2002), herein incorporated by reference in its entirety). After in-situ digestion and incubation of the proteins, the membrane can be placed directly into the mass spectrometer for peptide analysis.

A large number of methods reliant on the conformational variability of nucleic acids have been developed to detect SNPs.

For example, Single Strand Conformational Polymorphism (SSCP, Orita et al., *PNAS* 86:2766-2770 (1989), herein incorporated by reference in its entirety) is a method reliant on the ability of single-stranded nucleic acids to form secondary structure in solution under certain conditions. The secondary structure depends on the base composition and can be altered by a single nucleotide substitution, causing differences in electrophoretic mobility under nondenaturing conditions. The various polymorphs are typically detected by autoradiography when radioactively labeled, by silver staining of bands, by hybridisation with detectably labeled probe fragments or the use of fluorescent PCR primers which are subsequently detected, for example by an automated DNA sequencer.

Modifications of SSCP are well known in the art, and include the use of differing gel running conditions, such as for example differing temperature, or the addition of additives, and different gel matrices. Other variations on SSCP are well known to the skilled artisan, including, RNA-SSCP (Gasparini, P. et al. Scanning the first part of the neurofibromatosis type 1 gene by RNA-SSCP: identification of three novel mutations and of two new polymorphisms. *Hum Genet.* 97(4):492-5 (1996), herein incorporated by reference in its entirety), restriction endonuclease fingerprinting-SSCP (Liu, Q. et al. Restriction endonuclease fingerprinting (REF): a sensitive method for screening mutations in long, contiguous segments of DNA. *Biotechniques* 18(3):470-7 (1995), herein incorporated by reference in its entirety), dideoxy fingerprinting (a hybrid between dideoxy sequencing and SSCP) (Sarkar, G. et al. Dideoxy fingerprinting (ddF): a rapid and efficient screen for the presence of mutations. *Genomics* 13:441-443 (1992), herein incorporated by reference in its entirety), bi-directional dideoxy fingerprinting (in which the dideoxy termination reaction is performed simultaneously with two opposing primers) (Liu, Q. et al. Bi-directional dideoxy fingerprinting (Bi-ddF): a rapid method for quantitative detection of mutations in genomic regions of 300-600 bp. *Hum Mol Genet.* 5(1):107-14 (1996), herein incorporated by reference in its entirety), and Fluorescent PCR-SSCP (in which PCR products are internally labeled with multiple fluorescent dyes, can be digested with restriction enzymes, followed by SSCP, and analysed on an automated DNA sequencer able to detect the fluorescent dyes) (Makino, R. et al. F-SSCP: fluorescence-based polymerase chain reaction-single-strand conformation polymorphism (PCR-SSCP) analysis. *PCR Methods Appl.* 2(1):10-13 (1992), herein incorporated by reference in its entirety).

Other methods which utilize the varying mobility of different nucleic acid structures include Denaturing Gradient Gel Electrophoresis (DGGE) (Cariello, N. F. et al. Resolution of a missense mutant in human genomic DNA by denaturing gradient gel electrophoresis and direct sequencing using in vitro DNA amplification: HPRT Munich. *Am J Hum Genet.* 42(5):726-34 (1988), herein incorporated by reference in its entirety), Temperature Gradient Gel Electrophoresis (TGGE) (Riesner, D. et al. Temperature-gradient gel electrophoresis for the detection of polymorphic DNA and for quantitative polymerase chain reaction. *Electrophoresis.* 13:632-6 (1992), herein incorporated by reference in its entirety), and Heteroduplex Analysis (HET) (Keen, J. et al. Rapid detection of single base mismatches as heteroduplexes on Hydrolink gels. *Trends Genet.* 7(1):5 (1991), herein incorporated by reference in its entirety). Here, variation in the dissociation of double stranded DNA (for example, due to base-pair mismatches) results in a change in electrophoretic mobility. These mobility shifts are used to detect nucleotide variations.

Denaturing High Pressure Liquid Chromatography (HPLC) is yet a further method utilized to detect SNPs, using HPLC methods well-known in the art as an alternative to the separation methods described above (such as gel electophoresis) to detect, for example, homoduplexes and heteroduplexes which elute from the HPLC column at different rates, thereby enabling detection of mismatch nucleotides and thus SNPs (Giordano, M. et al. Identification by denaturing high-performance liquid chromatography of numerous polymorphisms in a candidate region for multiple sclerosis susceptibility. *Genomics* 56(3):247-53 (1999), herein incorporated by reference in its entirety).

Yet further methods to detect SNPs rely on the differing susceptibility of single stranded and double stranded nucleic acids to cleavage by various agents, including chemical cleavage agents and nucleolytic enzymes. For example, cleavage of mismatches within RNA:DNA heteroduplexes by RNase A, of heteroduplexes by, for example bacteriophage T4 endonuclease YII or T7 endonuclease I, of the 5' end of the hairpin loops at the junction between single stranded and double stranded DNA by cleavase I, and the modification of mispaired nucleotides within heteroduplexes by chemical agents commonly used in Maxam-Gilbert sequencing chemistry, are all well known in the art.

Further examples include the Protein Translation Test (PTT), used to resolve stop codons generated by variations which lead to a premature termination of translation and to protein products of reduced size, and the use of mismatch binding proteins (Moore, W. et al. Mutation detection in the breast cancer gene BRCA1 using the protein truncation test. *Mol Biotechnol.* 14(2):89-97 (2000), herein incorporated by reference in its entirety). Variations are detected by binding of, for example, the MutS protein, a component of *Escherichia coli* DNA mismatch repair system, or the human hMSH2 and GTBP proteins, to double stranded DNA heteroduplexes containing mismatched bases. DNA duplexes are then incubated with the mismatch binding protein, and variations are detected by mobility shift assay. For example, a simple assay is based on the fact that the binding of the mismatch binding protein to the heteroduplex protects the heteroduplex from exonuclease degradation.

Those skilled in the art will know that a particular SNP, particularly when it occurs in a regulatory region of a gene such as a promoter, can be associated with altered expression of a gene. Altered expression of a gene can also result when the SNP is located in the coding region of a protein-encoding gene, for example where the SNP is associated with codons of varying usage and thus with tRNAs of differing abundance. Such altered expression can be determined by methods well known in the art, and can thereby be employed to detect such SNPs. Similarly, where a SNP occurs in the coding region of a gene and results in a non-synonomous amino acid substitution, such substitution can result in a change in the function of the gene product. Similarly, in cases where the gene product is an RNA, such SNPs can result in a change of function in the RNA gene product. Any such change in function, for example as assessed in an activity or functionality assay, can be employed to detect such SNPs.

The above methods of detecting and identifying SNPs are amenable to use in the methods of the invention.

In practicing the present invention to assess the risk a particular subject faces with respect to a particular disease, that subject will be assessed to determine the presence or absence of polymorphisms (preferably SNPs) which are either associated with protection from the disease or susceptibility to the disease.

In order to detect and identify SNPs in accordance with the invention, a sample containing material to be tested is obtained from the subject. The sample can be any sample potentially containing the target SNPs (or target polypeptides, as the case may be) and obtained from any bodily fluid (blood, urine, saliva, etc) biopsies or other tissue preparations.

DNA or RNA can be isolated from the sample according to any of a number of methods well known in the art. For example, methods of purification of nucleic acids are described in Tijssen; Laboratory Techniques in Biochemistry and Molecular Biology: Hybridization with nucleic acid probes Part 1: Theory and Nucleic acid preparation, Elsevier, New York, N.Y. 1993, as well as in Maniatis, T., Fritsch, E. F. and Sambrook, J., Molecular Cloning Manual 1989 (each of the foregoing which is herein incorporated by reference in its entirety).

Upon detection of the presence or absence of the polymorphisms tested for, the critical step is to determine a net susceptibility score for the subject. This score will represent the balance between the combined value of the protective polymorphisms present and the total value of the susceptibility polymorphisms present, with a net protective score (i.e., a greater weight of protective polymorphisms present than susceptibility polymorphisms) being predictive of a reduced risk of developing the disease in question. The reverse is true where there is a net susceptibility score. To calculate where the balance lies, the individual polymorphisms are assigned a value. In the simplest embodiment, each polymorphisms within a category (i.e. protective or susceptibility) is assigned an equal value, with each protective polymorphism being −1 and each susceptibility polymorphism being +1 (or vice versa). It is however contemplated that the values assigned to individual polymorphisms within a category can differ, with some polymorphisms being assigned a value that reflects their predictive or discriminatory value. For example, one particularly strong protective polymorphism can have a value of −2, whereas another more weakly protective polymorphism can have a value of −0.75.

The net score, and the associated predictive outcome in terms of the risk of the subject developing a particular disease, can be represented in a number of ways. One example is as a graph as more particularly exemplified herein.

Another example is a simple numerical score (eg +2 to represent a subject with a net susceptibility score or −2 to represent a subject with a net protective score). In each case, the result is communicated to the subject with an explanation of what that result means to that subject. Preferably, advice on ways the subject can change their lifestyle so as to reduce the risk of developing the disease is also communicated to the subject.

It will be appreciated that the methods of the invention can be performed in conjunction with an analysis of other risk factors known to be associated with a disease, such as COPD, emphysema, OCOPD, or lung cancer. Such risk factors include epidemiological risk factors associated with an increased risk of developing the disease. Such risk factors include, but are not limited to smoking and/or exposure to tobacco smoke, age, sex and familial history. These risk factors can be used to augment an analysis of one or more polymorphisms as herein described when assessing a subject's risk of developing a disease such as COPD, emphysema, OCOPD, or lung cancer.

The predictive methods of the invention allow a number of therapeutic interventions and/or treatment regimens to be assessed for suitability and implemented for a given subject, depending upon the disease and the overall risk quotient. The simplest of these can be the provision to a subject with a net susceptibility score of motivation to implement a lifestyle change, for example, in the case of OCOPD, to reduce exposure to aero-pollutants, for example, by an occupational change or by the use of safety equipment in the work place. Similarly where the subject is a current smoker, the methods of the invention can provide motivation to quit smoking. In this latter case, a 'quit smoking' program can be followed, which can include the use of anti-smoking medicaments (such as nicotine patches and the like) as well as anti-addiction medicaments.

Other therapeutic interventions can involve altering the balance between protective and susceptibility polymorphisms towards a protective state (such as by neutralizing or reversing a susceptibility polymorphism). The manner of therapeutic intervention or treatment will be predicated by the nature of the polymorphism(s) and the biological effect of said polymorphism(s). For example, where a susceptibility polymorphism is associated with a change in the expression of a gene, intervention or treatment is preferably directed to the restoration of normal expression of said gene, by, for example, administration of an agent capable of modulating the expression of said gene. Where a polymorphism, such as a SNP allele or genotype, is associated with decreased expression of a gene, therapy can involve administration of an agent capable of increasing the expression of said gene, and conversely, where a polymorphism is associated with increased expression of a gene, therapy can involve administration of an agent capable of decreasing the expression of said gene. Methods useful for the modulation of gene expression are well known in the art. For example, in situations were a polymorphism is associated with upregulated expression of a gene, therapy utilizing, for example, RNAi or antisense methodologies can be implemented to decrease the abundance of mRNA and so decrease the expression of said gene. Alternatively, therapy can involve methods directed to, for example, modulating the activity of the product of said gene, thereby compensating for the abnormal expression of said gene.

Where a susceptibility polymorphism is associated with decreased gene product function or decreased levels of expression of a gene product, therapeutic intervention or treatment can involve augmenting or replacing of said function, or supplementing the amount of gene product within the subject for example, by administration of said gene product or a functional analogue thereof. For example, where a polymorphism is associated with decreased enzyme function, therapy can involve administration of active enzyme or an enzyme analogue to the subject. Similarly, where a polymorphism is associated with increased gene product function, therapeutic intervention or treatment can involve reduction of said function, for example, by administration of an inhibitor of said gene product or an agent capable of decreasing the level of said gene product in the subject. For example, where a polymorphism is associated with increased enzyme function, therapy can involve administration of an enzyme inhibitor to the subject.

Likewise, when a protective polymorphism is associated with upregulation of a particular gene or expression of an enzyme or other protein, therapies can be directed to mimic such upregulation or expression in an individual lacking the resistive genotype, and/or delivery of such enzyme or other protein to such individual Further, when a protective polymorphism is associated with downregulation of a particular gene, or with diminished or eliminated expression of an enzyme or other protein, desirable therapies can be directed to mimicking such conditions in an individual that lacks the protective genotype.

EXAMPLES

The invention will now be described in more detail, with reference to non-limiting examples.

Example 1

Case Association Study—COPD

Methods
Subject Recruitment

Subjects of European descent who had smoked a minimum of fifteen pack years and diagnosed by a physician with chronic obstructive pulmonary disease (COPD) were recruited. Subjects met the following criteria: were over 50 years old and had developed symptoms of breathlessness after 40 years of age, had a Forced expiratory volume in one second (FEV1) as a percentage of predicted <70% and a FEV1/FVC ratio (Forced expiratory volume in one second/Forced vital capacity) of <79% (measured using American Thoracic Society criteria). Two hundred and ninety-four subjects were recruited, of these 58% were male, the mean FEV1/FVC (±95% confidence limits) was 51% (49-53), mean FEV1 as a percentage of predicted was 43 (41-45). Mean age, cigarettes per day and pack year history was 65 yrs (64-66), 24 cigarettes/day (22-25) and 50 pack years (41-55) respectively. Two hundred and seventeen European subjects who had smoked a minimum of twenty pack years and who had never suffered breathlessness and had not been diagnosed with an obstructive lung disease in the past, in particular childhood asthma or chronic obstructive lung disease, were also studied. This control group was recruited through clubs for the elderly and consisted of 63% male, the mean FEV1/FVC (95%CI) was 82% (81-83), mean FEV1 as a percentage of predicted was 96 (95-97). Mean age, cigarettes per day and pack year history was 59 yrs (57-61), 24 cigarettes/day (22-26) and 42 pack years (39-45) respectively. Using a PCR based method [1, incorporated herein in its entirety by reference], all subjects were genotyped for the α1-antitrypsin mutations (S and Z alleles) and those with the ZZ allele were excluded. The COPD and resistant smoker cohorts were matched for subjects with the MZ genotype (5% in each cohort). 190 European blood donors (smoking status unknown) were recruited consecutively through local blood donor services. Sixty-three percent were men and their mean age was 50 years. On regression analysis, the age difference and pack years difference observed between COPD sufferers and resistant smokers was found not to determine FEV or COPD.

This study shows that polymorphisms found in greater frequency in COPD patients compared to controls (and/or resistant smokers) can reflect an increased susceptibility to the development of impaired lung function and COPD. Similarly, polymorphisms found in greater frequency in resistant smokers compared to susceptible smokers (COPD patients and/or controls) can reflect a protective role.

| Summary of characteristics for the COPD, resistant smoker and healthy blood donors | | | |
|---|---|---|---|
| Parameter Median (IQR) | COPD N = 294 | Resistant smokers N = 217 | Differences |
| % male | 58% | 63% | ns |
| Age (yrs) | 65 (64-66) | 59 (57-61) | $P < 0.05$ |
| Pack years | 50 (46-53) | 42 (39-45) | $P < 0.05$ |
| Cigarettes/day | 24 (22-25) | 24 (22-26) | ns |
| FEV1 (L) | 1.6 (0.7-2.5) | 2.9 (2.8-3.0) | $P < 0.05$ |
| FEV1 % predict | 43 (41-45) | 96% (95-97) | $P < 0.05$ |
| FEV1/FVC | 51 (49-53) | 82 (81-83) | $P < 0.05$ |

Means and 95% confidence limits

Cyclo-oxygenase 2 (COX2) −765 G/C Promoter Polymorphism and α1-antitrypsin Genotyping Genomic DNA was extracted from whole blood samples [2, herein incorporated by reference in its entirety]. The Cyclo-oxygenase 2 −765 polymorphism was determined by minor modifications of a previously published method [3, herein incorporated by reference in its entirety]. The PCR reaction was carried out in a total volume of 25 ul and contained 20 ng genomic DNA, 500 pmol forward and reverse primers, 0.2 mM dNTPs, 10 mM Tris-HCL (pH 8.4), 150 mM KCl, 1.0 mM $MgCl_2$ and 1 unit of polymerase (Life Technologies). Cycling times were incubations for 3 min at 95° C. followed by 33 cycles of 50s at 94° C., 60s at 66° C. and 60s at 72° C. A final elongation of 10 min at 72° C. then followed. 4 ul of PCR products were visualized by ultraviolet transillumination of a 3% agarose gel stained with ethidium bromide. An aliquot of 3 ul of amplification product was digested for 1 hr with 4 units of AciI (Roche Diagnostics, New Zealand) at 37° C. Digested products were separated on a 2.5% agarose gel run for 2.0 hours at 80 mV with TBE buffer. The products were visualized against a 123 bp ladder using ultraviolet transillumination after ethidium bromide staining. Using a PCR based method referenced above [1, herein incorporated by reference in its entirety], all COPD and resistant smoker subjects were genotyped for the α1-antitrypsin S and Z alleles.

Other Polymorphism Genotyping

Genomic DNA was extracted from whole blood samples [2]. Purified genomic DNA was aliquoted (10 ng/ul concentration) into 96 well plates and genotyped on a Sequenom™ system (Sequenom™ Autoflex Mass Spectrometer and Samsung 24 pin nanodispenser) using the following sequences, amplification conditions and methods.

The following conditions were used for the PCR multiplex reaction: final concentrations were for 10× Buffer 15 mM MgCl$_2$ 1.25×, 25 mM MgCl$_2$ 1.625 mM, dNTP mix 25 mM 500 uM, primers 4 uM 100 nM, Taq polymerase (Qiagen hot start) 0.15 U/reaction, Genomic DNA 10 ng/ul. Cycling times were 95° C. for 15 min, (5° C. for 15 s, 56° C. 30 s, 72° C. 30 s for 45 cycles with a prolonged extension time of 3 min to finish. Shrimp alkaline phosphotase (SAP) treatment was used (2 ul to 5 ul per PCR reaction) incubated at 35° C. for 30 min and extension reaction (add 2 ul to 7 ul after SAP treatment) with the following volumes per reaction of: water, 0.76 ul; hME 10× termination buffer, 0.2 ul; hME primer (10 uM), 1 ul; MassEXTEND enzyme, 0.04 ul.

| SNP_ID | TERM | WELL | 2$^{nd}$-PCRP | 1$^{st}$-PCRP |
|---|---|---|---|---|
| Vitamin DBP-420 | ACT | W1 | ACGTTGGATGGCTTGTTAACCAGCTTTGCC [SEQ. ID. NO. 1] | ACGTTGGATGTTTTTCAGACTGGCAGAGCG [SEQ. ID. NO. 2] |
| Vitamin DBP-416 | ACT | W1 | ACGTTGGATGTTTTTCAGACTGGCAGAGCG [SEQ. ID. NO. 3] | ACGTTGGATGGCTTGTTAACCAGCTTTGCC [SEQ. ID. NO. 4] |
| IL13 C-1055T | ACT | W2 | ACGTTGGATGCATGTCGCCTTTTCCTGCTC [SEQ. ID. NO. 5] | ACGTTGGATGCAACACCCAACAGGCAAATG [SEQ. ID. NO. 6] |
| GSTP1-105 | ACT | W2 | ACGTTGGATGTGGTGGACATGGTGAATGAC [SEQ. ID. NO. 7] | ACGTTGGATGTGGTGCAGATGCTCACATAG [SEQ. ID. NO. 8] |
| PAI1 G-675G | ACT | W2 | ACGTTGGATGCACAGAGAGAGTCTGGACAC [SEQ. ID. NO. 9] | ACGTTGGATGCTCTTGGTCTTTCCCTCATC [SEQ. ID. NO. 10] |
| NOS3-298 | ACT | W3 | ACGTTGGATGACAGCTCTGCATTCAGCACG [SEQ. ID. NO. 11] | ACGTTGGATGAGTCAATCCCTTTGGTGCTC [SEQ. ID. NO. 12] |
| IL13-Arg130Gln | ACT | W3 | ACGTTGGATGGTTTTCCAGCTTGCATGTCC [SEQ. ID. NO.13] | ACGTTGGATGCAATAGTCAGGTCCTGTCTC [SEQ. ID. NO. 14] |
| ADRB2-Arg16Gly | ACT | W3 | ACGTTGGATGGAACGGCAGCGCCTTCTTG [SEQ. ID. NO. 15] | ACGTTGGATGACTTGGCAATGGCTGTGATG [SEQ. ID. NO. 16] |
| IFNG-A874T | CGT | W5 | ACGTTGGATGCAGACATTCACAATTGATTT [SEQ. ID. NO. 17] | ACGTTGGATGGATAGTTCCAAACATGTGCG [SEQ. ID. NO. 18] |
| IL18-C-133G | ACT | W6 | ACGTTGGATGGGGTATTCATAAGCTGAAAC [SEQ. ID. NO. 19] | ACGTTGGATGCCTTCAAGTTCAGTGGTCAG [SEQ. ID. NO. 20] |
| IL18-A105C | ACT | W8 | ACGTTGGATGGGTCAATGAAGAGAACTTGG [SEQ. ID. NO. 21] | ACGTTGGATGAATGTTTATTGTAGAAAACC [SEQ. ID. NO. 22] |

Sequenom conditions for the polymorphisms genotyping-2

| SNP_ID | AMP_LEN | UP_CONF | MP_CONF | Tm(NN) | PcGC | PWARN | UEP_DIR |
|---|---|---|---|---|---|---|---|
| Vitamin DBP - 420 | 99 | 99.7 | 99.7 | 46.2 | 53.3 | ML | R |
| Vitamin DBP - 416 | 99 | 99.7 | 99.7 | 45.5 | 33.3 | M | F |
| IL13 C-1055T | 112 | 97.5 | 80 | 48.2 | 60 | L | R |
| GSTP1 - 105 | 107 | 99.4 | 80 | 49.9 | 52.9 | | F |
| PAI1 G-675G | 109 | 97.9 | 80 | 59.3 | 66.7 | g | F |
| NOS3 -298 | 186 | 98.1 | 65 | 61.2 | 63.2 | | F |
| IL13-Arg130Gln | 171 | 99.3 | 65 | 55.1 | 47.6 | | F |
| ADRB2- Arg16Gly | 187 | 88.2 | 65 | 65.1 | 58.3 | | F |
| IFNG - A874T | 112 | 75.3 | 81.2 | 45.6 | 27.3 | | F |
| IL18- C-133G | 112 | 93.5 | 74.3 | 41.8 | 46.7 | L | F |
| IL18- A105C | 121 | 67.2 | 74.3 | 48.9 | 40 | | R |

| Sequenom conditions for the polymorphisms genotyping =3 | | | | |
|---|---|---|---|---|
| SNP_ID | UEP_MASS | UEP_SEQ | EXT1_CALL | EXT1_MASS |
| Vitamin DBP-420 | 4518.9 | AGCTTTGCCAGTTCC [SEQ. ID. NO. 23] | A | 4807.1 |
| Vitamin DBP-416 | 5524.6 | AAAAGCAAAATTGCCTGA [SEQ. ID. NO. 24] | T | 5812.8 |
| IL13 C-1055T | 4405.9 | TCCTGCTCTTCCCTC [SEQ. ID. NO. 25] | T | 4703.1 |
| GSTP1-105 | 5099.3 | ACCTCCGCTGCAAATAC [SEQ. ID. NO. 26] | A | 5396.5 |
| PAI1 G-675G | 5620.6 | GAGTCTGGACACGTGGGG [SEQ. ID. NO. 27] | DEL | 5917.9 |
| NOS3-298 | 5813.8 | TGCTGCAGGCCCCAGATGA [SEQ. ID. NO. 28] | T | 6102 |
| IL13-Arg130Gln | 6470.2 | AGAAACTTTTTCGCGAGGGAC [SEQ. ID. NO. 29] | A | 6767.4 |
| ADRB2-Arg16Gly | 7264.7 | AGCGCCTTCTTGCTGGCACCCAAT [SEQ. ID. NO. 30] | A | 7561.9 |
| IFNG-A874T | 6639.4 | TCTTACAACACAAAATCAAATC [SEQ. ID. NO. 31] | T | 6927.6 |
| IL18-C-133G | 4592 | AGCTGAAACTTCTGG [SEQ. ID. NO. 32] | C | 4865.2 |
| IL18-A105C | 6085 | TCAAGCTTGCCAAAGTAATC [SEQ. ID. NO. 33] | A | 6373.2 |

| Sequenom conditions for the polymorphisms genotyping -4 | | | | | |
|---|---|---|---|---|---|
| SNP_ID | EXT1_SEQ | EXT2_CALL | EXT2_MASS | EXT2_SEQ | 1st PAUSE |
| Vitamin DBP-420 | AGCTTTGCCAGTTCCT [SEQ. ID. NO. 34] | C | 5136.4 | AGCTTTGCCAGTTCCGT [SEQ. ID. NO. 35] | 4848.2 |
| Vitamin DBP-416 | AAAAGCAAAATTGCCTGAT [SEQ. ID. NO. 36] | G | 6456.2 | AAAAGCAAAATTGCCTGAGGC [SEQ. ID. NO. 37] | 5853.9 |
| IL13 C-1055T | TCCTGCTCTTCCCTCA [SEQ. ID. NO. 38] | C | 5023.3 | TCCTGCTCTTCCCTCGT [SEQ. ID. NO. 39] | 4735.1 |
| GSTP1-105 | ACCTCCGCTGCAAATACA [SEQ. ID. NO. 40] | G | 5716.7 | ACCTCCGCTGCAAATACGT [SEQ. ID. NO. 41] | 5428.5 |
| PAI1 G-675G | GAGTCTGGACACGTGGGGA [SEQ. ID. NO. 42] | G | 6247.1 | GAGTCTGGACACGTGGGGGA [SEQ. ID. NO. 43] | 5949.9 |
| NOS3-298 | TGCTGCAGGCCCCAGATGAT [SEQ. ID. NO. 44] | G | 6416.2 | TGCTGCAGGCCCCAGATGAGC [SEQ. ID. NO. 45] | 6143 |
| IL13-Arg130Gln | AGAAACTTTTTCGCGAGGGACA [SEQ. ID. NO. 46] | G | 7416.8 | AGAAACTTTTTCGCGAGGGACGGT [SEQ. ID. NO. 47] | 6799.4 |
| ADRB2-Arg16Gly | AGCGCCTTCTTGCTGGCACCCAATA [SEQ. ID. NO. 48] | G | 8220.3 | AGCGCCTTCTTGCTGGCACCCAATGGA [SEQ. ID. NO. 49] | 7593.9 |
| IFNG-A874T | TCTTACAACACAAAATCAAATCT [SEQ. ID. NO. 50] | A | 7225.8 | TCTTACAACACAAAATCAAATCAC [SEQ. ID. NO. 51] | 6952.6 |
| IL18-C-133G | AGCTGAAACTTCTGGC [SEQ. ID. NO. 52] | G | 5218.4 | AGCTGAAACTTCTGGGA [SEQ. ID. NO. 53] | 4921.2 |
| IL18-A105C | TCAAGCTTGCCAAAGTAATCT [SEQ. ID. NO. 54] | C | 7040.6 | TCAAGCTTGCCAAAGTAATCGGA [SEQ. ID. NO. 55] | 6414.2 |

Sequenom conditions for the polymorphisms genotyping -5

| SNP_ID | 2nd-PCRP | 1st-PCRP |
|---|---|---|
| Lipoxygenase5-366G/A | ACGTTGGATGGAAGTCAGAGATGATGGCAG [SEQ. ID. NO. 56] | ACGTTGGATGATGAATCCTGGACCCAAGAC [SEQ. ID. NO. 57] |
| TNFalpha +489G/A | ACGTTGGATGGAAAGATGTGCGCTGATAGG [SEQ. ID. NO. 58] | ACGTTGGATGGCCACATCTCTTTCTGCATC [SEQ. ID. NO. 59] |
| SMAD3C89Y | ACGTTGGATGTTGCAGGTGTCCCATCGGAA [SEQ. ID. NO. 60] | ACGTTGGATGTAGCTCGTGGTGGCTGTGCA [SEQ. ID. NO. 61] |
| Caspase Gly881ArgG/C | ACGTTGGATGGTGATCACCCAAGGCTTCAG [SEQ. ID. NO. 62] | ACGTTGGATGGTCTGTTGACTCTTTTGGCC [SEQ. ID. NO. 63] |
| MBL2 +161G/A | ACGTTGGATGGTAGCTCTCCAGGCATCAAC [SEQ. ID. NO. 64] | ACGTTGGATGGTACCTGGTTCCCCCTTTTC [SEQ. ID. NO. 65] |
| HSP70-HOM2437T/C | ACGTTGGATGTGATCTTGTTCACCTTGCCG [SEQ. ID. NO. 66] | ACGTTGGATGAGATCGAGGTGACGTTTGAC [SEQ. ID. NO. 67] |
| CD14-159C/T | ACGTTGGATGAGACACAGAACCCTAGATGC [SEQ. ID. NO. 68] | ACGTTGGATGGCAATGAAGGATGTTTCAGG [SEQ. ID. NO. 69] |
| Chymase1-1903G/A | ACGTTGGATGTAAGACAGCTCCACAGCATC [SEQ. ID. NO. 70] | ACGTTGGATGTTCCATTTCCTCACCCTCAG [SEQ. ID. NO. 71] |
| TNFalpha-308G/A | ACGTTGGATGGATTTGTGTGTAGGACCCTG [SEQ. ID. NO. 72] | ACGTTGGATGGGTCCCCAAAAGAAATGGAG [SEQ. ID. NO. 73] |
| CLCA1 +13924T/A | ACGTTGGATGGGATTGGAGAACAAACTCAC [SEQ. ID. NO. 74] | ACGTTGGATGGGCAGCTGTTACACCAAAAG [SEQ. ID. NO. 75] |
| MEHTyr113HisT/C | ACGTTGGATGCTGGCGTTTTGCAAACATAC [SEQ. ID. NO. 76] | ACGTTGGATGTTGACTGGAAGAAGCAGGTG [SEQ. ID. NO. 77] |
| NAT2Arg197GlnG/A | ACGTTGGATGCCTGCCAAAGAAGAAACACC [SEQ. ID. NO. 78] | ACGTTGGATGACGTCTGCAGGTATGTATTC [SEQ. ID. NO. 79] |
| MEHHis139ArgG/A | ACGTTGGATGACTTCATCCACGTGAAGCCC [SEQ. ID. NO. 80] | ACGTTGGATGAAACTCGTAGAAAGAGCCGG [SEQ. ID. NO. 81] |
| IL-1B-511A/G | ACGTTGGATGATTTTCTCCTCAGAGGCTCC [SEQ. ID. NO. 82] | ACGTTGGATGTGTCTGTATTGAGGGTGTGG [SEQ. ID. NO. 83] |
| ADRB2Gln27GluC/G | ACGTTGGATGTTGCTGGCACCCAATGGAAG [SEQ. ID. NO. 84] | ACGTTGGATGATGAGAGACATGACGATGCC [SEQ. ID. NO. 85] |
| ICAM1E469KA/G | ACGTTGGATGACTCACAGAGCACATTCACG [SEQ. ID. NO. 86] | ACGTTGGATGTGTCACTCGAGATCTTGAGG [SEQ. ID. NO. 87] |

45

Sequenom conditions for the polymorphisms genotyping-6

| SNP_ID | AMP_LEN | UP_CONF | MP_CONF | Tm(NN) | PcGC | UEP_DIR |
|---|---|---|---|---|---|---|
| Lipoxygenase5-366G/A | 104 | 99.6 | 73.4 | 59 | 70.6 | F |
| TNFalpha+489G/A | 96 | 99.6 | 73.4 | 45.5 | 38.9 | F |
| SMAD3C89Y | 107 | 87.3 | 71.7 | 45.7 | 47.1 | F |
| CaspaseGly881ArgG/C | 111 | 97.2 | 81 | 52.9 | 58.8 | R |
| MBL2+161G/A | 99 | 96.8 | 81 | 50.3 | 52.9 | F |
| HSP70-HOM2437T/C | 107 | 99.3 | 81 | 62.2 | 65 | R |
| CD14-159C/T | 92 | 98 | 76.7 | 53.3 | 50 | F |
| Chymase1-1903G/A | 105 | 99.6 | 76.7 | 53.6 | 39.1 | R |
| TNFalpha-308G/A | 100 | 99.7 | 81.6 | 59.9 | 70.6 | R |
| CLCA1+13924T/A | 101 | 98 | 98 | 45.3 | 36.8 | R |
| MEHTyr113HisT/C | 103 | 97.7 | 82.2 | 48.7 | 42.1 | R |
| NAT2Arg197GlnG/A | 115 | 97.4 | 70 | 48.5 | 36.4 | F |
| MEHHis139ArgG/A | 115 | 96.7 | 77.8 | 66 | 82.4 | F |
| IL-1B-511A/G | 111 | 99.2 | 83 | 46 | 47.1 | R |
| ADRB2Gln27GluC/G | 118 | 96.6 | 80 | 52.2 | 66.7 | F |
| ICAM1E469KA/G | 115 | 98.8 | 95.8 | 51.5 | 52.9 | R |

Sequenom conditions for the polymorphisms genotyping -7

| SNP_ID | UEP_MASS | UEP_SEQ | EXT1_CALL | EXT1_MASS |
|---|---|---|---|---|
| Lipoxygenase5-366G/A | 5209.4 | GTGCCTGTGCTGGGCTC [SEQ. ID. NO. 88] | A | 5506.6 |
| TNFalpha + 489G/A | 5638.7 | GGATGGAGAGAAAAAAAC [SEQ. ID. NO. 89] | A | 5935.9 |
| SMAD3C89Y | 5056.3 | CCCTCATGTCATCTACT [SEQ. ID. NO. 90] | A | 5353.5 |
| CaspaseGly881ArgG/C | 5097.3 | GTCACCCACTCTGTTGC [SEQ. ID. NO. 91] | G | 5370.5 |
| MBL2 + 161G/A | 5299.5 | CAAAGATGGGCGTGATG [SEQ. ID. NO. 92] | A | 5596.7 |
| HSP70-HOM2437T/C | 6026.9 | CCTTGCCGGTGCTCTTGTCC [SEQ. ID. NO. 93] | T | 6324.1 |
| CD14-159C/T | 6068 | CAGAATCCTTCCTGTTACGG [SEQ. ID. NO. 94] | C | 6341.1 |
| Chymase1-1903G/A | 6973.6 | TCCACCAAGACTTAAGTTTTGCT [SEQ. ID. NO. 95] | G | 7246.7 |
| TNFalpha-308G/A | 5156.4 | GAGGCTGAACCCCGTCC [SEQ. ID. NO. 96] | G | 5429.5 |
| CLCA1 + 13924T/A | 5759.8 | CTTTTTCATAGAGTCCTGT [SEQ. ID. NO. 97] | A | 6048 |
| MEHTyr113HisT/C | 5913.9 | TTAGTCTTGAAGTGAGGGT [SEQ. ID. NO. 98] | T | 6211.1 |
| NAT2Arg197GlnG/A | 6635.3 | TACTTATTTACGCTTGAACCTC [SEQ. ID. NO. 99] | A | 6932.5 |
| MEHHis139ArgG/A | 5117.3 | CCAGCTGCCCGCAGGCC [SEQ. ID. NO. 100] | A | 5414.5 |
| IL-1B-511A/G | 5203.4 | AATTGACAGAGAGCTCC [SEQ. ID. NO. 101] | G | 5476.6 |
| ADRB2Gln27GluC/G | 4547 | CACGACGTCACGCAG [SEQ. ID. NO. 102] | C | 4820.2 |
| ICAM1E469KA/G | 5090.3 | CACATTCACGGTCACCT [SEQ. ID. NO. 103] | G | 5363.5 |

Sequenom conditions for the polymorphisms genotyping -8

| SNP_ID | EXT1_SEQ | EXT2 CALL | EXT2 MASS | EXT2_SEQ | 1st PAUSE |
|---|---|---|---|---|---|
| Lipoxygenase5-366G/A | GTGCCTGTGCTGGGCTCA [SEQ. ID. NO. 104] | G | 5826.8 | GTGCCTGTGCTGGGCTCGT [SEQ. ID. NO. 105] | 5538.6 |
| TNFalpha + 489G/A | GGATGGAGAGAAAAAAACA [SEQ. ID. NO. 106] | G | 6256.1 | GGATGGAGAGAAAAAAACGT [SEQ. ID. NO. 107] | 5967.9 |
| SMAD3C89Y | CCCTCATGTCATCTACTA [SEQ. ID. NO. 108] | G | 5658.7 | CCCTCATGTCATCTACTGC [SEQ. ID. NO. 109] | 5385.5 |
| CaspaseGly881ArgG/C | GTCACCCACTCTGTTGCC [SEQ. ID. NO. 110] | C | 5699.7 | GTCACCCACTCTGTTGCGC [SEQ. ID. NO. 111] | 5426.5 |
| MBL2 + 161G/A | CAAAGATGGGCGTGATGA [SEQ. ID. NO. 112] | G | 5901.9 | CAAAGATGGGCGTGATGGC [SEQ. ID. NO. 113] | 5628.7 |
| HSP70-HOM2437T/C | CCTTGCCGGTGCTCTTGTCCA [SEQ. ID. NO. 114] | C | 6644.3 | CCTTGCCGGTGCTCTTGTCCGT [SEQ. ID. NO. 115] | 6356.1 |

-continued

Sequenom conditions for the polymorphisms genotyping -8

| SNP_ID | EXT1_SEQ | EXT2 CALL | EXT2 MASS | EXT2_SEQ | 1$^{st}$ PAUSE |
|---|---|---|---|---|---|
| CD14-159C/T | CAGAATCCTTCCTGTTACGGC [SEQ. ID. NO. 116] | T | 6645.3 | CAGAATCCTTCCTGTTACGGTC [SEQ. ID. NO. 117] | 6372.2 |
| Chymase1-1903G/A | TCCACCAAGACTTAAGTTTTGCTC [SEQ. ID. NO. 118] | A | 7550.9 | TCCACCAAGACTTAAGTTTTGCTTC [SEQ. ID. NO. 119] | 7277.8 |
| TNFalpha-308G/A | GAGGCTGAACCCCGTCCC [SEQ. ID. NO. 120] | A | 5733.7 | GAGGCTGAACCCCGTCCTC [SEQ. ID. NO. 121] | 5460.6 |
| CLCA1 + 13924T/A | CTTTTTCATAGAGTCCTGTT [SEQ. ID. NO. 122] | T | 6659.4 | CTTTTTCATAGAGTCCTGTAAC [SEQ. ID. NO. 123] | 6073 |
| MEHTyr113HisT/C | TTAGTCTTGAAGTGAGGGTA [SEQ. ID. NO. 124] | C | 6531.3 | TTAGTCTTGAAGTGAGGGTGT [SEQ. ID. NO. 125] | 6243.1 |
| NAT2Arg197GlnG/A | TACTTATTTACGCTTGAACCTCA [SEQ. ID. NO. 126] | G | 7261.8 | TACTTATTTACGCTTGAACCTCGA [SEQ. ID. NO. 127] | 6964.5 |
| MEHHis139ArgG/A | CCAGCTGCCCGCAGGCCA [SEQ. ID. NO. 128] | G | 5734.7 | CCAGCTGCCCGCAGGCCGT [SEQ. ID. NO. 129] | 5446.5 |
| IL-1B-511A/G | AATTGACAGAGAGCTCCC [SEQ. ID. NO. 130] | A | 5820.8 | AATTGACAGAGAGCTCCTG [SEQ. ID. NO. 131] | 5507.6 |
| ADRB2Gln27GluC/G | CACGACGTCACGCAGC [SEQ. ID. NO. 132] | G | 5173.4 | CACGACGTCACGCAGGA [SEQ. ID. NO. 133] | 4876.2 |
| ICAM1E469KA/G | CACATTCACGGTCACCTC [SEQ. ID. NO. 134] | A | 5707.7 | CACATTCACGGTCACCTTG [SEQ. ID. NO. 135] | 5394.5 |

Results

Frequencies of individual polymorphisms are as follows:

TABLE 1

Polymorphism allele and genotype frequencies in the COPD patients and resistant smokers.

Cyclo-oxygenase 2 −765 G/C

| | Allele* | | Genotype | | |
|---|---|---|---|---|---|
| Frequency | C | G | CC | CG | GG |
| Controls n = 94 (%) | 27 (14%) | 161 (86%) | 3 (3%) | 21 (22%) | 70 (75%) |
| COPD n = 202 (%) | 59 (15%) | 345 (85%) | 6 (3%) | 47 (23%) | 149 (74%) |
| Resistant n = 172 (%) | 85[2] (25%) | 259 (75%) | 14[1] (8%) | 57 (33%) | 101 (59%) |

Beta2-adrenoreceptor Arg 16 Gly

| | Allele* | | Genotype | | |
|---|---|---|---|---|---|
| Frequency | A | G | AA | AG | GG |
| Controls n = 182 (%) | 152 (42%) | 212 (58%) | 26 (14%) | 100 (55%) | 56 (31%) |
| COPD n = 236 (%) | 164 (34%) | 308 (66%) | 34 (14%) | 96 (41%) | 106[3] (45%) |
| Resistant n = 190 (%) | 135 (36%) | 245 (64%) | 34 (18%) | 67 (35%) | 89[4] (47%) |

Interleukin 18 105 A/C

| | Allele* | | Genotype | | |
|---|---|---|---|---|---|
| Frequency | C | A | CC | AC | AA |
| Controls n = 184 (%) | 118 (32%) | 250 (68%) | 22 (12%) | 74 (40%) | 88 (48%) |
| COPD n = 240 (%) | 122 (25%) | 377[6] (75%) | 21 (9%) | 80 (33%) | 139[5,7] (58%) |
| Resistant n = 196 (%) | 113 (29%) | 277 (71%) | 16 (8%) | 81 (41%) | 99 (50%) |

TABLE 1-continued

Polymorphism allele and genotype frequencies in the COPD patients and resistant smokers.

Interleukin 18 −133 C/G

| Frequency | Allele* | | Genotype | | |
|---|---|---|---|---|---|
| | G | C | GG | GC | CC |
| Controls n = 187 (%) | 120 (32%) | 254 (68%) | 23 (12%) | 74 (40%) | 90 (48%) |
| COPD n = 238 | 123 (26%) | 353[9] (74%) | 21 (9%) | 81 (34%) | 136[8] (57%) |
| Resistant n = 195 (%) | 113 (29%) | 277 (71%) | 16 (8%) | 81 (42%) | 98 (50%) |

Plasminogen activator inhibitor 1 −675 4G/5G

| Frequency | Allele* | | Genotype | | |
|---|---|---|---|---|---|
| | 5G | 4G | 5G5G | 5G4G | 4G4G |
| Controls n = 186 (%) | 158 (42%) | 214 (58%) | 31 (17%) | 96 (52%) | 59 (32%) |
| COPD n = 237 (%) | 219[12] (46%) | 255 (54%) | 54[10,11] (23%) | 111 (47%) | 72 (30%) |
| Resistant n = 194 (%) | 152 (39%) | 236 (61%) | 31 (16%) | 90 (46%) | 73[10,11] (38%) |

Nitric oxide synthase 3 Asp 298 Glu (T/G)

| Frequency | Allele* | | Genotype | | |
|---|---|---|---|---|---|
| | T | G | TT | TG | GG |
| Controls n = 183 (%) | 108 (30%) | 258 (70%) | 13 (7%) | 82 (45%) | 88 (48%) |
| COPD n = 238 (%) | 159 (42%) | 317 (58%) | 25 (10%) | 109 (47%) | 104 (43%) |
| Resistant n = 194 (%) | 136 (35%) | 252 (65%) | 28[13] (15%) | 80 (41%) | 86 (44%) |

Vitamin D Binding Protein Lys 420 Thr (A/C)

| Frequency | Allele* | | Genotype | | |
|---|---|---|---|---|---|
| | A | C | AA | AC | CC |
| Controls n = 189 (%) | 113 (30%) | 265 (70%) | 17 (9%) | 79 (42%) | 93 (49%) |
| COPD n = 250 (%) | 147 (29%) | 353 (71%) | 24 (10%) | 99 (40%) | 127 (50%) |
| Resistant n = 195 (%) | 140[15] (36%) | 250 (64%) | 25[14] (13%) | 90[14] (46%) | 80 (41%) |

Vitamin D Binding Protein Glu 416 Asp (T/G)

| Frequency | Allele* | | Genotype | | |
|---|---|---|---|---|---|
| | T | G | TT | TG | GG |
| Controls n = 188 (%) | 162 (43%) | 214 (57%) | 35 (19%) | 92 (49%) | 61 (32%) |
| COPD n = 240 (%) | 230 (48%) | 250 (52%) | 57 (24%) | 116 (48%) | 67 (28%) |
| Resistant n = 197 (%) | 193[17] (49%) | 201 (51%) | 43[16] (22%) | 107[16] (54%) | 47 (24%) |

Glutathione S Transferase P1 Ile 105 Val (A/G)

| Frequency | Allele* | | Genotype | | |
|---|---|---|---|---|---|
| | A | G | AA | AG | GG |
| Controls n = 185 (%) | 232 (63%) | 138 (37%) | 70 (38%) | 92 (50%) | 23 (12%) |
| COPD n = 238 (%) | 310 (65%) | 166 (35%) | 96 (40%) | 118 (50%) | 24 (10%) |
| Resistant n = 194 (%) | 269[19] (69%) | 119 (31%) | 91[18] (47%) | 87 (45%) | 16 (8%) |

Interferon-gamma 874 A/T

| Frequency | Allele* | | Genotype | | |
|---|---|---|---|---|---|
| | A | T | AA | AT | TT |
| Controls n = 186 (%) | 183 (49%) | 189 (51%) | 37 (20%) | 109 (58%) | 40 (22%) |
| COPD n = 235 (%) | 244 (52%) | 226 (48%) | 64[20] (27%) | 116 (49%) | 55 (24%) |
| Resistant n = 193 (%) | 208 (54%) | 178 (46%) | 51 (27%) | 106 (55%) | 36 (18%) |

TABLE 1-continued

Polymorphism allele and genotype frequencies in the COPD patients and resistant smokers.

Interleukin-13 Arg 130 Gln (G/A)

| Frequency | Allele* | | Genotype | | |
|---|---|---|---|---|---|
| | A | G | AA | AG | GG |
| Controls n = 184 (%) | 67 (18%) | 301 (82%) | 3 (2%) | 61 (33%) | 120 (65%) |
| COPD n = 237 (%) | 86 (18%) | 388 (82%) | 8 (3%) | 70 (30%) | 159 (67%) |
| Resistant n = 194 (%) | 74 (19%) | 314 (81%) | $9^{21}$ (5%) | 56 (28%) | 129 (67%) |

Interleukin-13 −1055 C/T

| Frequency | Allele* | | Genotype | | |
|---|---|---|---|---|---|
| | T | C | TT | TC | CC |
| Controls n = 182 (%) | 65 (18%) | 299 (82%) | 5 (3%) | 55 (30%) | 122 (67%) |
| COPD n = 234 (%) | 94 (20%) | 374 (80%) | $8^{22}$ (4%) | 78 (33%) | 148 (63%) |
| Resistant n = 192 (%) | 72 (19%) | 312 (81%) | 2 (1%) | 68 (35%) | 122 (64%) |

α1-antitrypsin S

| Frequency | Allele* | | Genotype | | |
|---|---|---|---|---|---|
| | M | S | MM | MS | SS |
| COPD n = 202 (%) | 391 (97%) | 13 (3%) | 189 (94%) | 13 (6%) | 0 (0%) |
| Resistant n = 189 (%) | 350 (93%) | 28 (7%) | 162 (85%) | $26^{23}$ (14%) | $1^{23}$ (1%) |

*number of chromosomes (2n)Genotype

[1] Genotype. CC/CG vs GG for resistant vs COPD, Odds ratio (OR) = 1.98, 95% confidence limits 1.3-3.1, $\chi^2$ (Yates corrected) = 8.82, p = 0.003, CC/CG = protective for COPD

[2] Allele. C vs G for resistant vs COPD, Odds ratio (OR) = 1.92, 95% confidence limits 1.3-2.8, $\chi^2$ (Yates corrected) = 11.56, p < 0.001, C = protective for COPD

[3] Genotype. GG vs AG/AA for COPD vs controls, Odds ratio (OR) = 1.83, 95% confidence limits 1.2-2.8, $\chi^2$ (Yates corrected) = 8.1, p = 0.004, GG = susceptible to COPD (depending on the presence of other snps)

[4] Genotype. GG vs AG/AA for resistant vs controls, Odds ratio (OR) = 1.98, 95% confidence limits 1.3-3.1, $\chi^2$ (Yates corrected) = 9.43, p = 0.002 GG = resistance (depending on the presence of other snps)

[5] Genotype. AA vs AC/CC for COPD vs controls, Odds ratio (OR) = 1.50, 95% confidence limits 1.0-2.3, $\chi^2$ (Yates uncorrected) = 4.26, p = 0.04, AA = susceptible to COPD

[6] Allele. A vs C for COPD vs control, Odds ratio (OR) = 1.46, 95% confidence limits 1.1-2.0, $\chi^2$ (Yates corrected) = 5.76, p = 0.02

[7] Genotype. AA vs AC/CC for COPD vs resistant, Odds ratio (OR) = 1.35, 95% confidence limits 0.9-2.0, $\chi^2$ (Yates uncorrected) = 2.39, p = 0.12 (trend), AA = susceptible to COPD

[8] Genotype. CC vs CG/GG for COPD vs controls, Odds ratio (OR) = 1.44, 95% confidence limits 1.0-2.2, $\chi^2$ (Yates corrected) = 3.4, p = 0.06, CC = susceptible to COPD

[9] Allele. C vs G for COPD vs control, Odds ratio (OR) = 1.36, 95% confidence limits 1.0-1.9, $\chi^2$ (Yates corrected) = 53.7, p = 0.05, C = susceptible to COPD

[10] Genotype. 5G5G vs rest for COPD vs resistant, Odds ratio (OR) = 1.55, 95% confidence limits 0.9-2.6, $\chi^2$ (Yates uncorrected) = 3.12, p = 0.08, 5G5G = susceptible to COPD

[11] Genotype. 5G5G vs rest for COPD vs control, Odds ratio (OR) = 1.48, 95% confidence limits 0.9-2.5, $\chi^2$ (Yates uncorrected) = 2.43, p = 0.12, 5G5G = susceptible to COPD

[12] Allele. 5G vs 4G for COPD vs resistant, Odds ratio (OR) = 1.33, 95% confidence limits 1.0-1.8, $\chi^2$ (Yates corrected) = 4.02, p = 0.05, 5G = susceptible to COPD

[13] Genotype. TT vs TG/GG for resistant vs controls, Odds ratio (OR) = 2.2, 95% confidence limits 1.0-4.7, $\chi^2$ (Yates corrected) = 4.49, p = 0.03, TT genotype = protective for COPD

[14] Genotype. AA/AC vs CC for resistant vs COPD, Odds ratio (OR) = 1.39, 95% confidence limits 0.9-2.1, $\chi^2$ (Yates uncorrected) = 2.59, p = 0.10, AA/AC genotype = protective for COPD

[15] Allele. A vs C for resistant vs COPD, Odds ratio (OR) = 1.34, 95% confidence limits 1.0-1.8, $\chi^2$ (Yates corrected) = 3.94, p = 0.05, A allele = protective for COPD

[16] Genotype. TT/TG vs GG for resistant vs controls, Odds ratio (OR) = 1.53, 95% confidence limits 1.0-2.5, $\chi^2$ (Yates uncorrected) = 3.52, p = 0.06, TT/TG genotype = protective for COPD

[17] Allele. T vs G for resistant vs control, Odds ratio (OR) = 1.27, 95% confidence limits 1.0-1.7, $\chi^2$ (Yates corrected) = 2.69, p = 0.1, T allele = protective for COPD

[18] Genotype. AA vs AG/GG for resistant vs controls, Odds ratio (OR) = 1.45, 95% confidence limits 0.9-2.2, $\chi^2$ (Yates uncorrected) = 3.19, p = 0.07, AA genotype = protective for COPD

[19] Allele. A vs G for resistant vs control, Odds ratio (OR) = 1.34, 95% confidence limits 1.0-1.8, $\chi^2$ (Yates uncorrected) = 3.71, p = 0.05, A allele = protective for COPD

[20] Genotype. AA vs AT/TT for COPD vs controls, Odds ratio (OR) = 1.51, 95% confidence limits 0.9-2.5, $\chi^2$ (Yates uncorrected) = 3.07, p = 0.08, AA genotype = susceptible to COPD

[21] Genotype. AA vs AG/GG for resistant vs controls, Odds ratio (OR) = 2.94, 95% confidence limits 0.7-14.0, $\chi^2$ (Yates uncorrected) = 2.78, p = 0.09, AA genotype = protective for COPD

[22] Genotype. TT vs TC/CC for COPD vs resistant, Odds ratio (OR) = 6.03, 95% confidence limits 1.1-42, $\chi^2$ (Yates corrected) = 4.9, p = 0.03, TT = susceptible to COPD

[23] Genotype. MS/SS vs MM for Resistant vs COPD, Odds ratio (OR) = 2.42, 95% confidence limits 1.2-5.1, $\chi^2$ (Yates corrected) = 5.7, p = 0.01, S = protective for COPD

Tumor Necrosis Factor α +489 G/A polymorphism allele and genotype frequency in the COPD patients and resistant smokers.

| Frequency | 1. Allele* A | G | 2. Genotype AA | AG | GG |
|---|---|---|---|---|---|
| COPD n = 242 (%) | 54 (11%) | 430 (89%) | 5 (2%) | 44 (18%) | 193 (80%) |
| Resistant n = 187 (%) | 27 (7%) | 347 (93%) | 1 (1%) | 25 (13%) | 161 (86%) |

*number of chromosomes (2n)
1. Genotype. AA/AG vs GG for COPD vs resistant, Odds ratio (OR) = 1.57, 95% confidence limits 0.9-2.7, $\chi^2$ (Yates corrected) = 2.52, p = 0.11, AA/AG = susceptible (GG = protective)
2. Allele. A vs G for COPD vs resistant, Odds ratio (OR) = 1.61, 95% confidence limits 1.0-2.7, $\chi^2$ (Yates corrected) = 3.38, p = 0.07, A = susceptible

Tumor Necrosis Factor α −308 G/A polymorphism allele and genotype frequency in the COPD patients and resistant smokers.

| Frequency | 3. Allele* A | G | 4. Genotype AA | AG | GG |
|---|---|---|---|---|---|
| COPD n = 242 (%) | 90 (19%) | 394 (81%) | 6 (2%) | 78 (32%) | 158 (65%) |
| Resistant n = 190 (%) | 58 (15%) | 322 (85%) | 3 (2%) | 52 (27%) | 135 (71%) |

*number of chromosomes (2n)
1. Genotype. GG vs AG/AA for COPD vs resistant, Odds ratio (OR) = 0.77, 95% confidence limits 0.5-1.2, $\chi^2$ (Yates uncorrected) = 1.62, p = 0.20, GG = protective (AA/AG = susceptible) trend
2. Allele. A vs G for COPD vs resistant, Odds ratio (OR) = 1.3, 95% confidence limits 0.9-1.9, $\chi^2$ (Yates uncorrected) = 1.7, p = 0.20, A = susceptible trend

SMAD3 C89Y polymorphism allele and genotype frequency in the COPD patients and resistant smokers.

| Frequency | 5. Allele* A | G | 6. Genotype AA | AG | GG |
|---|---|---|---|---|---|
| COPD n = 250 (%) | 2 (1%) | 498 (99%) | 0 (0%) | 2 (1%) | 248 (99%) |
| Resistant n = 196 (%) | 6 (2%) | 386 (98%) | 0 (0%) | 6 (3%) | 190 (97%) |

*number of chromosomes (2n)
1. Genotype. AA/AG vs GG for COPD vs resistant, Odds ratio (OR) = 0.26, 95% confidence limits 0.04-1.4, $\chi^2$ (Yates uncorrected) = 3.19, p = 0.07, AA/AG = protective (GG susceptible)

Intracellular Adhesion molecule 1 (ICAM1) A/G E469K (rs5498) polymorphism allele and genotype frequency in COPD patients and resistant smokers.

| Frequency | 7. Allele* A | G | 8. Genotype AA | AG | GG |
|---|---|---|---|---|---|
| COPD n = 242 (%) | 259 (54%) | 225 (46%) | 73 (30%) | 113 (47%) | 56 (23%) |
| Resistant n = 182 (%) | 217 (60%) | 147 (40%) | 64 (35%) | 89 (49%) | 29 (16%) |

*number of chromosomes (2n)
1. Genotype. GG vs AG/GG for COPD vs resistant, Odds ratio (OR) = 1.60, 95% confidence limits 0.9-2.7, $\chi^2$ (Yates corrected) = 3.37, p = 0.07, GG = susceptibility
2. Allele. G vs A for COPD vs resistant, Odds ratio (OR) = 1.3, 95% confidence limits 1.0-1.7, $\chi^2$ (Yates corrected) = 2.90, p = 0.09

Caspase (NOD2) Gly881Arg polymorphism allele and genotype frequencies in the COPD patients and resistant smokers.

| Frequency | 9. Allele* G | C | 10. Genotype GG | GC | CC |
|---|---|---|---|---|---|
| COPD n = 247 | 486 (98%) | 8 (2%) | 239 (97%) | 8 (3%) | 0 (0%) |
| Resistant n = 195 (%) | 388 (99.5%) | 2 0.5%) | 193 (99%) | 2 (1%) | 0 (0%) |

*number of chromosomes (2n)
1. Genotype. CC/CG vs GG for COPD vs resistant, Odds ratio (OR) = 3.2, 95% confidence limits 0.6-22, $\chi^2$ (Yates uncorrected) = 2.41, p = 0.11 (1-tailed), GC/CC = susceptibility (trend)

Mannose binding lectin 2(MBL2) +161 G/A polymorphism allele and genotype frequencies in the COPD patients and resistant smokers.

| Frequency | 11. Allele* A | G | 12. Genotype AA | AG | GG |
|---|---|---|---|---|---|
| COPD n = 218 (%) | 110 (25%) | 326 (75%) | 6 (3%) | 98 (45%) | 114 (52%) |
| Resistant n = 183 (%) | 66 (18%) | 300 (82%) | 6 (3%) | 54 (30%) | 123 (67%) |

*number of chromosomes (2n)
1. Genotype. GG vs rest for COPD vs resistant, Odds ratio (OR) = 0.53, 95% confidence limits 0.4-0.80, $\chi^2$ (Yates uncorrected) = 8.55, p = 0.003, GG = protective

Chymase 1 (CMA1) −1903 G/A promoter polymorphism allele and genotype frequencies in the COPD patients and resistant smokers.

| Frequency | 13. Allele* A | G | 14. Genotype AA | AG | GG |
|---|---|---|---|---|---|
| COPD n = 239 (%) | 259 (54%) | 219 (46%) | 67 (28%) | 125 (52%) | 47 (20%) |
| Resistant n = 181 (%) | 209 (58%) | 153 (42%) | 63 (35%) | 83 (46%) | 35 (19%) |

*number of chromosomes (2n)
1. Genotype. AA vs AG/GG for COPD vs resistant, Odds ratio (OR) = 0.73, 95% confidence limits 0.5-1.1, $\chi^2$ (Yates corrected) = 1.91, p = 0.17, AA genotype = protective trend

N-Acetyltransferase 2 Arg 197 Gln G/A polymorphism allele and genotype frequencies in COPD and resistant smokers.

| Frequency | 15. Allele* A | G | 16. Genotype AA | AG | GG |
|---|---|---|---|---|---|
| COPD n = 247 (%) | 136 (28%) | 358 (72%) | 14 (6%) | 108 (44%) | 125 (50%) |
| Resistant n = 196 (%) | 125 (32%) | 267 (68%) | 21 (11%) | 83 (42%) | 92 (47%) |

*number of chromosomes (2n)
1. Genotype. AA vs AG/GG for COPD vs resistant, Odds ratio (OR) = 0.50, 95% confidence limits 0.2-1.0, $\chi^2$ (Yates uncorrected) = 3.82, p = 0.05, AA genotype = protective

Interleukin 1B (IL-1b) −511 A/G polymorphism allele and genotype frequencies in COPD and resistant smokers.

| Frequency | 17. Allele* A | G | 18. Genotype AA | AG | GG |
|---|---|---|---|---|---|
| COPD n = 248 (%) | 160 (32%) | 336 (68%) | 31 (13%) | 98 (40%) | 119 (48%) |
| Resistant n = 195 (%) | 142 (36%) | 248 (64%) | 27 (14%) | 88 (45%) | 80 (41%) |

*number of chromosomes (2n)
1. Genotype. GG vs AA/AG for COPD vs resistant, Odds ratio (OR) = 1.3, 95% confidence limits 0.9-2.0, $\chi^2$ (Yates corrected) = 1.86, p = 0.17, GG genotype = susceptible trend

Microsomal epoxide hydrolase (MEH) Tyr 113 His T/C (exon 3) polymorphism allele and genotype frequency in COPD and resistant smokers.

| Frequency | 19. Allele* C | T | 20. Genotype CC | CT | TT |
|---|---|---|---|---|---|
| COPD n = 249 (%) | 137 (28%) | 361 (72%) | 18 (7%) | 101 (41%) | 130 (52%) |
| Resistant n = 194 (%) | 130 (34%) | 258 (66%) | 19 (10%) | 92 (47%) | 83 (43%) |

*number of chromosomes (2n)
1. Genotype. TT vs CT/CC for COPD vs resistant, Odds ratio (OR) = 1.5, 95% confidence limits 1.0-2.2, $\chi^2$ (Yates corrected) = 3.51, p = 0.06, TT genotype = susceptible

Microsomal epoxide hydrolase (MEH) His 139 Arg A/G (exon 4) polymorphism allele and genotype frequency in COPD and resistant smokers.

| Frequency | 21. Allele* A | G | 22. Genotype AA | AG | GG |
|---|---|---|---|---|---|
| COPD n = 238 (%) | 372 (78%) | 104 (22%) | 148 (62%) | 76 (32%) | 14 (6%) |
| Resistant n = 179 (%) | 277 (77%) | 81 (23%) | 114 (64%) | 49 (27%) | 16 (9%) |

*number of chromosomes (2n)
1. Genotype. GG vs AA/AG for COPD vs resistant, Odds ratio (OR) = 0.64, 95% confidence limits 0.3-1.4, $\chi^2$ (Yates uncorrected) = 1.43, p = 0.23, GG genotype = protective (trend)

Lipo-oxygenase −366 G/A polymorphism allele and genotype frequencies in the COPD patients and resistant smokers.

| Frequency | 23. Allele* A | G | 24. Genotype AA | AG | GG |
|---|---|---|---|---|---|
| COPD n = 247 (%) | 21 (4%) | 473 (96%) | 1 (0.5%) | 19 (7.5%) | 227 (92%) |
| Resistant n = 192 (%) | 25 (7%) | 359 (93%) | 0 (0%) | 25 (13%) | 167 (87%) |

*number of chromosomes (2n)
1. Genotype. AA/AG vs GG for COPD vs resistant, Odds ratio (OR) = 0.60, 95% confidence limits 0.3-1.1, $\chi^2$ (Yates corrected) = 2.34, p = 0.12, AA/AG genotype = protective (GG susceptible) trend

Heat Shock Protein 70 (HSP 70) HOM T2437C polymorphism allele and genotype frequencies in the COPD patients and resistant smokers.

| Frequency | 25. Allele* C | T | 26. Genotype CC | CT | TT |
|---|---|---|---|---|---|
| COPD n = 199 (%) | 127 (32%) | 271 (68%) | 5 (3%) | 117 (59%) | 77 (39%) |
| Resistant n = 166 (%) | 78 (23%) | 254 (77%) | 4 (2%) | 70 (42%) | 92 (56%) |

*number of chromosomes (2n)
1. Genotype. CC/CT vs TT for COPD vs resistant, Odds ratio (OR) = 2.0, 95% confidence limits 1.3-3.1, $\chi^2$ (Yates uncorrected) = 9.52, p = 0.002, CC/CT genotype = susceptible (TT = protective)

Chloride Channel Calcium-activated 1 (CLCA1) +13924 T/A polymorphism allele and genotype frequencies in the COPD patients and resistant smokers.

| Frequency | 27. Allele* A | T | 28. Genotype AA | AT | TT |
|---|---|---|---|---|---|
| COPD n = 224 (%) | 282 (63%) | 166 (37%) | 84 (38%) | 114 (51%) | 26 (12%) |
| Resistant n = 158 (%) | 178 (56%) | 138 (44%) | 42 (27%) | 94 (59%) | 22 (14%) |

*number of chromosomes (2n)
1. Genotype. AA vs AT/TT for COPD vs resistant, Odds ratio (OR) = 1.7, 95% confidence limits 1.0-2.7, $\chi^2$ (Yates corrected) = 4.51, p = 0.03, AA = susceptible

Monocyte differentiation antigen CD-14 −159 promoter polymorphism allele and genotype frequencies in the COPD patients and resistant smokers.

| Frequency | 29. Allele* C | T | 30. Genotype CC | CT | TT |
|---|---|---|---|---|---|
| COPD n = 240 (%) | 268 (56%) | 212 (44%) | 77 (32%) | 114 (48%) | 49 (20%) |
| Resistant n = 180 (%) | 182 (51%) | 178 (49%) | 46 (25%) | 90 (50%) | 44 (24%) |

*number of chromosomes (2n)
1. Genotype. CC vs CT/TT for COPD vs Resistant, Odds ratio (OR) = 1.4, 95% confidence limits 0.9-2.2, $\chi^2$ (Yates uncorrected) = 2.12, p = 0.15, CC = susceptible (trend)

Elafin +49 C/T polymorphism allele and genotype frequencies in the COPD patients, resistant smokers and controls.

| Frequency | 31. Allele* C | T | 32. Genotype CC | CT | TT |
|---|---|---|---|---|---|
| COPD n = 144 (%) | 247 (86%) | 41 (14%) | 105 (73%) | 37 (26%) | 2 (1%) |
| Resistant n = 75 (%) | 121 (81%) | 29 (19%) | 49 (65%) | 23 (31%) | 3 (4%) |

*number of chromosomes (2n)
1. Genotype. CT/TT vs CC for COPD vs resistant, Odds ratio (OR) = 0.70, 95% confidence limits = 0.4-1.3, $\chi^2$ (Yates uncorrected) = 1.36, p = 0.24, CT/TT genotype = protective (trend only)
2. Allele: T vs C for COPD vs resistant, Odds ratio (OR) = 0.69, 95% confidence limits = 0.4-1.2, $\chi^2$ (Yates uncorrected) = 1.91, p = 0.17, T genotype = protective (trend only)

Beta2-adrenoreceptor Glu 27 Glu polymorphism allele and genotype frequency in the COPD patients, resistant smokers and controls.

|  | 33. Allele* | | 34. Genotype | | |
| --- | --- | --- | --- | --- | --- |
| Frequency | C | G | CC | CG | GG |
| Controls n = 185 (%) | 204 (55%) | 168 (45%) | 57 (31%) | 89 (48%) | 39 (21%) |
| COPD n = 238 (%) | 268 (56%) | 208 (44%) | 67 (28%) | 134 (56%) | 37 (16%) |
| Resistant n = 195 (%) | 220 (56%) | 170 (44%) | 64 (33%) | 92 (47%) | 39 (20%) |

*number of chromosomes (2n)

1. Genotype. GG vs CG/CC for COPD vs resistant, Odds ratio (OR) = 0.74, 95% confidence limits = 0.4-1.2, $\chi^2$ (Yates uncorrected) = 1.47, p = 0.23, GG = protective (trend)
2. Genotype. GG vs CG/CC for COPD vs controls, Odds ratio (OR) = 0.69, 95% confidence limits = 0.4-1.2, $\chi^2$ (Yates uncorrected) = 2.16, p = 0.14, GG = protective (trend)

Maxtrix metalloproteinase 1 (MMP1) −1607 1G/2G polymorphism allele and genotype frequencies in COPD patients, resistant smokers and controls.

|  | 35. Allele* | | 36. Genotype | | |
| --- | --- | --- | --- | --- | --- |
| Frequency | 1G | 2G | 1G1G | 1G2G | 2G2G |
| Controls n = 174 (%) | 214 (61%) | 134 (39%) | 68 (39%) | 78 (45%) | 28 (16%) |
| COPD n = 217 (%) | 182 (42%) | 252 (58%) | 47 (22%) | 88 (41%) | 82 (38%) |
| Resistant n = 187 (%) | 186 (50%) | 188 (50%) | 46 (25%) | 94 (50%) | 47 (25%) |

*number of chromosomes (2n)

1. Genotype. 1G1G vs rest for COPD vs controls, Odds ratio (OR) = 0.43, 95% confidence limits 0.3-0.7, $\chi^2$ (Yates uncorrected) = 13.3, p = 0.0003 1G1G genotype = protective
2. Allele. 1G vs 2G for COPD vs controls, Odds ration (OR) = 0.45, 95% confidence limits 0.3-0.6, $\chi^2$ (Yates corrected) = 28.8, p < 0.0001, 1G = protective
3. Genotype. 1G1G/1G2G vs rest for COPD vs resistant smokers, Odds ratio (OR) = 0.55, 95% confidence limits 0.4-0.9, $\chi^2$ (Yates uncorrected) = 6.83, p = 0.009 1G1G/1G2G genotypes = protective
4. Allele. 1G vs 2G for COPD vs resistant smokers, Odds ratio (OR) = 0.73, 95% confidence limits 0.6-1.0, $\chi^2$ (Yates corrected) = 4.61, p = 0.03, 1G = protective
5. Genotype. 2G2G vs 1G1G/1G2G for COPD vs controls, Odds ratio (OR) = 3.17, 95% confidence limits 1.9-5.3, $\chi^2$ (Yates uncorrected) = 21.4, p < 0.0001 2G2G genotype = susceptible
6. Allele. 2G vs 1G for COPD vs controls, Odds ratio (OR) = 2.2, 95% confidence limits 1.6-3.0, $\chi^2$ (Yates corrected) = 28.8, p < 0.00001, 2G = susceptible
7. Genotype. 2G2G vs 1G1G/1G2G for COPD vs resistant, Odds ratio (OR) = 1.81, 95% confidence limits 1.2-2.9, $\chi^2$ (Yates uncorrected) = 6.83, p = 0.009 2G2G genotype = susceptible
8. Allele. 2G vs 1G for COPD vs resistant, Odds ratio (OR) = 1.4, 95% confidence limits 1.0-1.8, $\chi^2$ (Yates corrected) = 4.61, p = 0.0.03, 2G = susceptible Table 2 below provides a summary of the protective and susceptibility polymorphisms determined for COPD.

TABLE 2

Summary of protective and susceptibility polymorphisms for COPD

| Gene | Polymorphism | Role |
| --- | --- | --- |
| Cyclo-oxygenase 2 (COX2) | COX2 −765 G/C | CC/CG protective |
| β2-adrenoreceptor (ADBR) | ADBR Arg16Gly | GG susceptible |
| Interleukin-18 (IL18) | IL18 −133 C/G | CC susceptible |
| Interleukin-18 (IL18) | IL18 105 A/C | AA susceptible |
| Plasminogen activator inhibitor 1 (PAI-1) | PAI-1 −675 4G/5G | 5G5G susceptible |
| Nitric Oxide synthase 3 (NOS3) | NOS3 298 Asp/Glu | TT protective |
| Vitamin D Binding Protein (VDBP) | VDBP Lys 420 Thr | AA/AC protective |
| Vitamin D Binding Protein (VDBP) | VDBP Glu 416 Asp | TT/TG protective |
| Glutathione S Transferase (GSTP-1) | GSTP1 Ile105Val | AA protective |
| Interferon ? (IFN-?) | IFN-γ 874 A/T | AA susceptible |
| Interleukin-13 (IL13) | IL13 Arg 130 Gln | AA protective |
| Interleukin-13 (IL13) | Il13 −1055C/T | TT susceptible |
| α1-antitrypsin (α1-AT) | α1-AT S allele | MS protective |
| Tumor Necrosis Factor α TNFa | TNFα +489 G/A | AA/AG susceptible GG protective |
| Tumor Necrosis Factor α TNFa | TNFα −308 G/A | GG protective AA/AG susceptible |
| SMAD3 | SMAD3 C89Y AG | AA/AG protective GG susceptible |
| Intracellular adhesion molecule 1 (ICAM1) | ICAM E469K A/G | GG susceptible |
| Caspase (NOD2) | NOD2 Gly 881Arg G/C | GC/CC susceptible |
| Mannose binding lectin 2 (MBL2) | MBL2 161 G/A | GG protective |
| Chymase 1 (CMA1) | CMA1 −1903 G/A | AA protective |
| N-Acetyl transferase 2 (NAT2) | NAT2 Arg 197 Gln G/A | AA protective |
| Interleukin 1B (IL1B) | (IL1B) −511 A/G | GG susceptible |
| Microsomal epoxide hydrolase (MEH) | MEH Tyr 113 His T/C | TT susceptible |
| Microsomal epoxide hydrolase (MEH) | MEH His 139 Arg G/A | GG protective |
| 5 Lipo-oxygenase (ALOX5) | ALOX5 −366 G/A | AA/AG protective GG susceptible |
| Heat Shock Protein 70 (HSP 70) | HSP 70 HOM T2437C | CC/CT susceptible TT protective |
| Chloride Channel Calcium-activated 1 (CLCA1) | CLCA1 +13924 T/A | AA susceptible |
| Monocyte differentiation antigen CD-14 | CD-14 −159 C/T | CC susceptible |
| Elafin | Elafin Exon 1 +49 C/T | CT/TT protective |
| B2-adrenergic receptor (ADBR) | ADBR Gln 27 Glu G/G | GG protective |
| Matrix metalloproteinase 1 (MMP1) | MMP1 −1607 1G/2G | 1G1G/1G2G protective |

The combined frequencies of the presence or absence of the selected protective genotypes COX2 (−765) CC/CG, β2 adreno-receptor AA, Interleukin-13 AA, Nitic Oxide Synthase 3 TT, and Vitamin D Binding Protein AA observed in the COPD subjects and in resistant smokers is presented below in Table 3.

TABLE 3

Combined frequencies of the presence or absence of selected protective genotypes in COPD subjects and in resistant smokers.

| Cohorts | Number of protective polymorphisms | | | |
|---|---|---|---|---|
| | 0 | 1 | =2 | Total |
| COPD | 136 (54%) | 100 (40%) | 16 (7%) | 252 |
| Resistant smokers | 79 (40%) | 83 (42%) | 34 (17%) | 196 |
| % of smokers with COPD | 136/215 (63%) | 100/183 (55%) | 16/50 (32%) | |

| Comparison | Odd's ratio | 95% CI | ?2 | P value |
|---|---|---|---|---|
| 0 vs 1 vs 2+, Resist vs COPD | — | — | 16.43 | 0.0003 |
| 2+ vs 0-1, Resist vs COPD | 3.1 | 1.6-6.1 | 12.36 | 0.0004 |
| 1+ vs 0, Resist vs COPD | 1.74 | 1.2-2.6 | 7.71 | 0.006 |

The combined frequencies of the presence or absence of the selected susceptibility genotypes Interleukin-18 105 AA, PAI-1 −675 5G5G, Interleukin-13 −1055 TT, and Interferon-? −874 AA observed in the COPD subjects and in resistant smokers is presented below in Table 4.

TABLE 4

Combined frequencies of the presence or absence of selected susceptibility genotypes in the COPD subjects and in resistant smokers.

| Cohorts | Number of protective polymorphisms | | | |
|---|---|---|---|---|
| | 0 | 1 | =2 | Total |
| COPD | 66 (26%) | 113 (45%) | 73 (29%) | 252 |
| Resistant smokers | 69 (35%) | 92 (47%) | 35 (18%) | 196 |
| % of smokers with COPD | 66/135 (49%) | 113/205 (55%) | 73/108 (68%) | |

| Comparison | Odd's ratio | 95% CI | ?2 | P value |
|---|---|---|---|---|
| 0 vs 1 vs 2+, COPD vs Resist | — | — | 8.72 | 0.01 |
| 2+ vs 0-1, COPD vs Resist | 1.9 | 1.2-3.0 | 6.84 | 0.009 |
| 1+ vs 0, COPD vs Resist | 1.5 | 1.0-3.5 | 3.84 | 0.05 |

The combined frequencies of the presence or absence of the protective genotypes COX2 (−765) CC/CG, Interleukin-13 AA, Nitic Oxide Synthase 3 TT, Vitamin D Binding Protein AA/AC, GSTP 1 AA, and α1-antitypsin MS/SS, observed in the COPD subjects and in resistant smokers is presented below in Table 5 and in FIG. 1.

TABLE 5

Combined frequencies of the presence or absence of selected protective genotypes in the COPD subjects and in resistant smokers.

| Cohorts | Number of protective polymorphisms | | | |
|---|---|---|---|---|
| | 0 | 1 | =2 | Total |
| COPD | 51 (19%) | 64 (24%) | 150 (57%) | 265 |
| Resistant smokers | 16 (8%) | 56 (27%) | 133 (65%) | 205 |
| % of smokers with COPD | 51/76 (76%) | 64/120 (53%) | 150/283 (53%) | |

| Comparison | Odd's ratio | 95% CI | ?2 | P value |
|---|---|---|---|---|
| 0 vs 1 vs 2+, Resist vs COPD | — | — | 12.14 | 0.0005 |
| 1+ vs 0, Resist vs COPD | 2.82 | 1.5-5.3 | 11.46 | 0.0004 |

Figure 2:
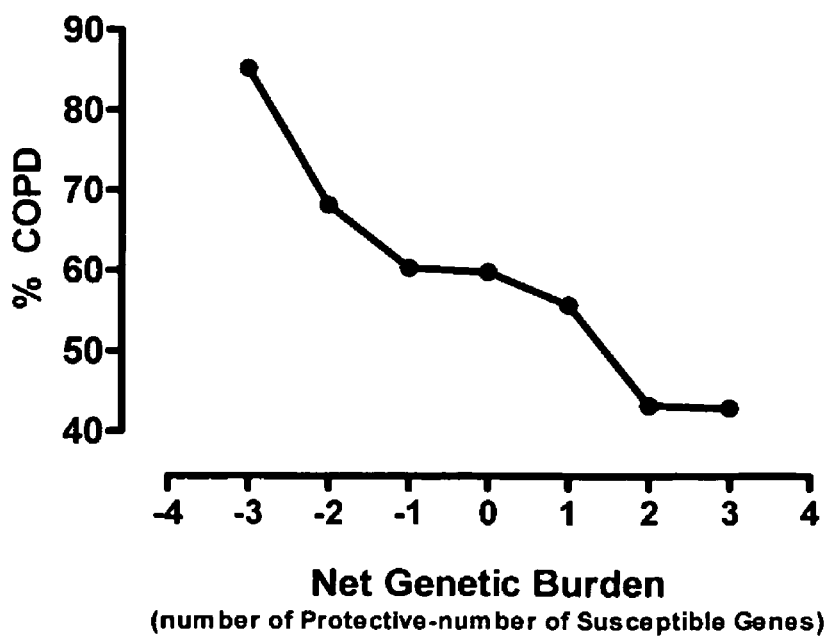
FIG. 2: depicts a graph showing net scores for protective and susceptibility polymorphisms in COPD subjects.

Protective polymophisms were assigned a score of +1 while susceptibility polymorphisms were assigned a score of −1. For each subject, a net score was then calculated according to the presence of susceptibility and protective genotypes. This produced a linear spread of values. When assessed as a range between −3 to +3, a linear relationship as depicted in FIG. 2 was observed. This analysis indicates that for subjects with a net score of −2 or less, there was a 70% or greater risk of having COPD. In contrast, for subjects with a net score of 2+ or greater the risk was approximately 40% (see FIG. 2).

In an analysis in which the value of a given polymorphism was weighted based on the Odd's ratio for that polymorphism (generated by comparing its frequency between resistant and COPD subjects), a linear relationship was again observed. This analysis allowed for the distinction of smokers at high or low risk of having COPD.

I. Example 2

Case Association Study—OCOPD

Methods
Subject Recruitment

Subjects of European decent who had been exposed to chronic smoking (minimum 15 pack years) and aero-pollutants in the work place (noxious dusts or fumes) were identified from respiratory clinics. After spirometric testing those with occupational chronic obstructive pulmonary disease (OCOPD) with forced expiratory volume in one second (FEV1) as a percentage of predicted <70% and a FEV1/FVC ratio (Forced expiratory volume in one second/Forced vital capacity) of <79% (measured using American Thoracic Society criteria) were recruited. One hundred and thirty-nine subjects were recruited, of these 70% were male, the mean FEV1/FVC (±Standard Deviation) was 54% (SD 15), mean FEV1 as a percentage of predicted was 46 (SD 19). Mean age, cigarettes per day, and pack year history was 62 yrs (SD 9), 25 cigarettes/day (SD 16) and 53 pack years (SD 31), respectively. One hundred and twelve European subjects who had smoked a minimum of fifteen pack years and similarly been exposed in the work place to potentially noxious dusts or fumes were also studied. This control group was recruited through community studies of lung function and were 81% male; the mean FEV1/FVC (SD) was 81% (SD 8), and mean FEV1 as a percentage of predicted was 96 (SD 10). Mean age, cigarettes per day and pack year history was 58 yrs (SD 11), 26 cigarettes/day (SD 14) and 45 pack years (SD 28), respectively. Using a PCR based method [1], all subjects were genotyped for the α1-antitrypsin mutations (M, S and Z alleles) and those with the ZZ allele were excluded. The OCOPD and resistant smoker cohorts were matched for subjects with the MZ genotype (6% in each cohort). They were also matched for age started smoking (mean 16 yr) and aged stopped smoking (mid fifties). 190 European blood donors (smoking and occupational exposure status unknown) were recruited consecutively through local blood donor services. Sixty-three percent were men and their mean age was 50 years. On regression analysis, the age difference and pack years difference observed between OCOPD sufferers and resistant smokers was found not to determine FEV or OCOPD.

Summary of characteristics for the OCOPD and exposed resistant smoker cohorts.

| Parameter Mean (SD) | OCOPD (N = 139) | Exposed resistant smokers (N = 112) | Differences |
|---|---|---|---|
| % male | 70% | 81% | $P < 0.05$ |
| Age (yrs) | 62 (9) | 58 (11) | ns |
| Pack years | 53 (31) | 45 (28) | $P < 0.05$ |
| Cigarettes/day | 25 (16) | 26 (14) | ns |
| FEV1 (L) | 1.3 (0.7) | 3.0 (0.7) | $P < 0.05$ |
| FEV1 % predict | 46 (19) | 96% (10) | $P < 0.05$ |
| FEV1/FVC | 54 (15) | 81 (8) | $P < 0.05$ |

Means and 1SD

Cyclooxygenase 2 (COX2) −765 G/C Promoter Polymorphism and α1-antitrypsin genotyping Genomic DNA was extracted from whole blood samples [2]. The COX2 −765 polymorphism was determined by minor modifications of a previously published method [3]. The PCR reaction was carried out in a total volume of 25 ul and contained 20 ng genomic DNA, 500 pmol forward and reverse primers, 0.2 mM dNTPs, 10 mM Tris-HCL (pH 8.4), 150 mM KCl, 1.0 mM $MgCl_2$ and 1 unit of Taq polymerase (Life Technologies). Cycling times were incubations for 3 min at 95° C. followed by 33 cycles of 50 s at 94° C., 60 s at 66° C. and 60 s at 72° C. A final elongation of 10 min at 72° C. then followed. 4 ul of PCR products were visualized by ultraviolet trans-illumination of a 6% agarose gel stained with ethidium bromide. An aliquot of 3 ul of amplification product was digested for 1 hr with 4 units of AciI (Roche Diagnostics, New Zealand) at 37° C. Digested products were separated on a 2.5% agarose gel run for 2.0 hrs at 80 mV with TBE buffer and visualized using ultraviolet transillumination after ethidium bromide staining against a 123 bp ladder. Using a PCR based method discussed above [3], all smoking subjects were genotyped for the α1-antitrypsin M, S and Z alleles.

Genotyping of the Superoxide Dismutase 3 Arg 312 Gln Polymorphism

Genomic DNA was extracted using standard phenol and chloroform methods. Cohorts of patients and controls were configured in to 96-well PCR format containing strategic negative controls. The assay primers, PCR conditions and RFLP assays details have been previously described [4, herein incorporated by reference in its entirety]. Genotyping was done using minor modifications of the above protocol optimized for laboratory conditions. The PCR reactions were amplified in MJ Research thermocyclers in a total volume of 25 μl and contained 80 ng genomic DNA, 10 pmol forward and reverse primers, 0.1 mM dNTPs, 10 mM Tris-HCL (pH 8.4), 150 mM KCl, 1.0 mM $MgCl_2$ and 0.5 unit of Taq polymerase (Qiagen). Aliquots of amplification product were digested for 4 hrs with 5 U of the relevant restriction enzymes (Roche Diagnostics, New Zealand) at designated temperatures and conditions. Digested products were separated on 8% polyacrylamide gels (49:1, Sigma). The products were visualized by ultraviolet transillumination following ethidium bromide staining and migration compared against a 1 Kb plus ladder standard (Invitrogen). Genotypes were recorded in data spreadsheets and statistical analysis performed.

Genotyping of the Microsomal Epoxide Hydrolase Exon 3 TC Polymorphism

Genomic DNA was extracted using standard phenol and chloroform methods. Cohorts of patients and controls were configured in to 96-well PCR format containing strategic negative controls. The assay primers, PCR conditions and RFLP assays details have been previously described [5, herein incorporated by reference in its entirety]. Genotyping was done using minor modifications of the above protocol optimized for laboratory conditions. The PCR reactions were amplified in MJ Research thermocyclers in a total volume of 25 μl and contained 80 ng genomic DNA, 100 ng forward and reverse primers, 0.2 mM dNTPs, 10 mM Tris-HCL (pH 8.4), 150 mM KCl, 1.5 mM $MgCl_2$ and 1.0 unit of Taq polymerase (Qiagen). Cycling conditions consisted of 94° C. 60 s, 56° C. 20 s, 72° C. 20 s for 38 cycles with an extended last extension of 3 min. Aliquots of amplification product were digested for 4 hrs with 5 U of the relevant restriction enzymes Eco RV (Roche Diagnostics, New Zealand) at designated temperature conditions. Digested products were separated on 8% polyacrylamide gels (49:1, Sigma). The products were visualized by ultraviolet transillumination following ethidium bromide staining and migration compared against a 1 Kb plus ladder standard (Invitrogen). Genotypes were recorded in data spreadsheets and statistical analysis performed.

Genotyping of the 3' 1237 G/A (T/t) polymorphism of the α1-antitrypsin Gene

Genomic DNA was extracted using standard phenol and chloroform methods. Cohorts of patients and controls were configured in to 96-well PCR format containing strategic negative controls. The assay primers, PCR conditions and RFLP assays details have been previously described [Sandford A J et al., [6], each of which is herein incorporated by reference in its entirety]. Genotyping was done using minor modifications of the above protocol optimized for laboratory conditions The PCR reactions were amplified in MJ Research thermocyclers in a total volume of 25 μl and contained 80 ng genomic DNA, 100 ng forward and reverse primers, 0.2 mM dNTPs, 10 mM Tris-HCL (pH 8.4), 150 mM KCl, 1.5 mM $MgCl_2$ and 1.0 unit of Taq polymerase (Qiagen). Forward and reverse prime sequences were 5'-CTACCAGGAATGGCCT-TGTCC-3' [SEQ. ID. NO.136] and 5'-CTCTCAGGTCTG-GTGTCATCC-3' [SEQ. ID. NO.137]. Cycling conditions consisted of 94 C 60 s, 56C 20 s, 72 C 20 s for 38 cycles with an extended last extension of 3 min. Aliquots of amplification product were digested for 4 hrs with 2 Units of the restriction enzymes Taq 1 (Roche Diagnostics, New Zealand) at designated temperature conditions. Digested products were separated on 3% agarose. The products were visualized by ultraviolet transillumination following ethidium bromide staining and migration compared against a 1 Kb plus ladder standard (Invitrogen). Genotypes were recorded in data spreadsheets and statistical analysis performed.

Genotyping of the Asp 299 Gly Polymorphism of the Toll-like Receptor 4 Gene

Genomic DNA was Extracted Using Standard Phenol and Chloroform methods. Cohorts of patients and controls were configured in to 96-well PCR format containing strategic negative controls. The assay primers, PCR conditions and RFLP assays details have been previously described [6]. Genotyping was done using minor modifications of the above protocol optimized for laboratory conditions The PCR reactions were amplified in MJ Research thermocyclers in a total volume of 25 μl and contained 80 ng genomic DNA, 100 ng forward and reverse primers, 0.2 mM dNTPs, 10 mM Tris-HCL (pH 8.4), 150 mM KCl, 1.5 mM MgCl$_2$ and 1.0 unit of Taq polymerase (Qiagen). Forward and reverse prime sequences were 5'-GATTAGCATACTTAGACTACTAC-CTCCATG-3' [SEQ.ID.NO.138] and 5'-GATCAACTTCT-GAAAAAGCATTCCCAC-3' [SEQ.ID.NO.139]. Cycling conditions consisted of 94° C. 30 s, 55° C. 30 s, 72° C. 30s for 30 cycles with an extended last extension of 3 min. Aliquots of amplification product were digested for 4 hrs with 2 U of the restriction enzyme Nco I (Roche Diagnostics, New Zealand) at designated temperature conditions. Digested products were separated on 3% agarose gel. The products were visualized by ultraviolet transillumination following ethidium bromide staining and migration compared against a 1 Kb plus ladder standard (Invitrogen). Genotypes were recorded in data spreadsheets and statistical analysis performed.

Genotyping of the −1607 1G2G Polymorphism of the Matrix Metalloproteinase 1 Gene Genomic DNA was extracted using standard phenol and chloroform methods. Cohorts of patients and controls were configured in to 96-well PCR format containing strategic negative controls. The assay primers, PCR conditions and RFLP assays details have been previously described [Dunleavey L, et al]. Genotyping was done using minor modifications of the above protocol optimized for laboratory conditions The PCR reactions were amplified in MJ Research thermocyclers in a total volume of 25 μl and contained 80 ng genomic DNA, 100 ng forward and reverse primers, 200 mM dNTPs, 20 mM Tris-HCL (pH 8.4), 50 mM KCl, 1.5 mM MgCl$_2$ and 1.0 unit of Taq polymerase (Qiagen). Forward and reverse prime sequences were 3' TCGTGAGAATGTCTTC-CCATT-3' [SEQ.ID.NO.140] and 5'-TCTTGGAT-TGATTTGAGATAAGTGAAATC-3' [SEQ.ID.NO.141]. Cycling conditions consisted of 94 C 60 s, 55 C 30 s, 72C 30 s for 35 cycles with an extended last extension of 3 min. Aliquots of amplification product were digested for 4 hrs with 6 Units of the restriction enzymes XmnI (Roche Diagnostics, New Zealand) at designated temperature conditions. Digested products were separated on 6% polyacrylamide gel. The products were visualized by ultraviolet transillumination following ethidium bromide staining and migration compared against a 1 Kb plus ladder standard (Invitrogen). Genotypes were recorded in data spreadsheets and statistical analysis performed.

Other Polymorphism Genotyping

Genomic DNA was extracted from whole blood samples [4]. Purified genomic DNA was aliquoted (10 ng/ul concentration) into 96 well plates and genotyped on a Sequenom™ system (Sequenomtm Autoflex Mass Spectrometer and Samsung 24 pin nanodispenser) using the sequences, amplification conditions and methods described below.

The following conditions were used for the PCR multiplex reaction: final concentrations were for 10× Buffer 15 mM MgCl2 1.25×, 25 mM MgCl2 1.625 mM, dNTP mix 25 mM 500 uM, primers 4 uM 100 nM, Taq polymerase (Quiagen hot start) 0.15 u/reaction, Genomic DNA 10 ng/ul. Cycling times were 95° C. for 15 min, (5° C. for 15s, 56° C. 30s, 72° C. 30s for 45 cycles with a prolonged extension time of 3 min to finish. We used shrimp alkaline phosphotase (SAP) treatment (2 ul to 5 ul PCR reaction) incubated at 35° C. for 30 min and extension reaction (add 2 ul to 7 ul after SAP treatment) with the following volumes per reaction of water 0.76 ul, hME 10× termination buffer 0.2 ul, hME primer (10 uM) 1 ul, MassEXTEND enzyme 0.04 ul.

| Sequenom conditions for the polymorphisms genotyping -1 | | | | |
|---|---|---|---|---|
| SNP_ID | TERM | WELL | 2$^{nd}$-PCRP | 1$^{st}$-PCRP |
| VDBP-420 | ACT | W1 | ACGTTGGATGGCTTGTTAACCAGCTTTGCC [SEQ. ID. NO. 142] | ACGTTGGATGTTTTTCAGACTGGCAGAGCG [SEQ. ID. NO. 143] |
| VDBP-416 | ACT | W1 | ACGTTGGATGTTTTTCAGACTGGCAGAGCG [SEQ. ID. NO. 144] | ACGTTGGATGGCTTGTTAACCAGCTTTGCC [SEQ. ID. NO. 145] |
| ADRB2-Gln27Glu | ACT | W2 | ACGTTGGATGTTGCTGGCACCCAATGGAAG [SEQ. ID. NO. 146] | ACGTTGGATGATGAGAGACATGACGATGCC [SEQ. ID. NO. 147] |
| GSTP1-105 | ACT | W2 | ACGTTGGATGTGGTGGACATGGTGAATGAC [SEQ. ID. NO. 148] | ACGTTGGATGTGGTGCAGATGCTCACATAG [SEQ. ID. NO. 149] |
| PAI1 G-675G | ACT | W2 | ACGTTGGATGCACAGAGAGAGTCTGGACAC [SEQ. ID. NO. 150] | ACGTTGGATGCTCTTGGTCTTTCCCTCATC [SEQ. ID. NO. 151] |
| IL-11 G518A | ACT | W3 | ACGTTGGATGCCTCTGATCCTCTTTGCTTC [SEQ. ID. NO. 152] | ACGTTGGATGAAGAGGGAGTGGAAGGGAAG [SEQ. ID. NO. 153] |
| NOS3-298 | ACT | W3 | ACGTTGGATGACAGCTCTGCATTCAGCACG [SEQ. ID. NO. 154] | ACGTTGGATGAGTCAATCCCTTTGGTGCTC [SEQ. ID. NO. 155] |
| IL-8 A-251T | CGT | W5 | ACGTTGGATGACTGAAGCTCCACAATTTGG [SEQ. ID. NO. 156] | ACGTTGGATGGCCACTCTAGTACTATATCTG [SEQ. ID. NO. 157] |
| IL-18 C-133G | ACT | W6 | ACGTTGGATGGGGTATTCATAAGCTGAAAC [SEQ. ID. NO. 158] | ACGTTGGATGCCTTCAAGTTCAGTGGTCAG [SEQ. ID. NO. 159] |
| IL-18 A105C | ACT | W8 | ACGTTGGATGGGTCAATGAAGAGAACTTGG [SEQ. ID. NO. 160] | ACGTTGGATGAATGTTTATTGTAGAAAACC [SEQ. ID. NO. 161] |

| Sequenom conditions for the polymorphisms genotyping-2 | | | | | | | |
|---|---|---|---|---|---|---|---|
| SNP_ID | AMP_LEN | UP_CONF | MP_CONF | Tm(NN) | PcGC | PWARN | UEP_DIR |
| VDBP – 420 | 99 | 99.7 | 99.7 | 46.2 | 53.3 | ML | R |
| VDBP – 416 | 99 | 99.7 | 99.7 | 45.5 | 33.3 | M | F |
| ADRB2-Gln27Glu | 118 | 96.6 | 80 | 52.2 | 66.7 | L | F |
| GSTP1 –105 | 107 | 99.4 | 80 | 49.9 | 52.9 |  | F |
| PAI1 G-675G | 109 | 97.9 | 80 | 59.3 | 66.7 | g | F |
| IL-11 G518A | 169 | 97.5 | 65 | 52.9 | 52.6 | s | F |
| NOS3 – 298 | 186 | 98.1 | 65 | 61.2 | 63.2 |  | F |
| IL-8 A-251T | 119 | 92.6 | 81.2 | 45.9 | 28.6 |  | R |
| IL-18 C-133G | 112 | 93.5 | 74.3 | 41.8 | 46.7 | L | F |
| IL-18 A105C | 121 | 67.2 | 74.3 | 48.9 | 40 |  | R |

| Sequenom conditions for the polymorphisms genotyping -3 | | | | | |
|---|---|---|---|---|---|
| SNP_ID | UEP_MASS | UEP_SEQ |  | EXT1_CALL | EXT1_MASS |
| VDBP-420 | 4518.9 | AGCTTTGCCAGTTCC | [SEQ. ID. NO. 162] | A | 4807.1 |
| VDBP-416 | 5524.6 | AAAAGCAAAATTGCCTGA | [SEQ. ID. NO. 163] | T | 5812.8 |
| ADRB2-Gln27Glu | 4547 | CACGACGTCACGCAG | [SEQ. ID. NO. 164] | C | 4820.2 |
| GSTP1-105 | 5099.3 | ACCTCCGCTGCAAATAC | [SEQ. ID. NO. 165] | A | 5396.5 |
| PAI1 G-675G | 5620.6 | GAGTCTGGACACGTGGGG | [SEQ. ID. NO. 166] | DEL | 5917.9 |
| IL-11 G518A | 5705.7 | TCCATCTCTGTGGATCTCC | [SEQ. ID. NO. 167] | A | 6002.9 |
| NOS3-298 | 5813.8 | TGCTGCAGGCCCCAGATGA | [SEQ. ID. NO. 168] | T | 6102 |
| IL-8A-251T | 6428.2 | CACAATTTGGTGAATTATGAA | [SEQ. ID. NO. 169] | A | 6716.4 |
| IL-18 C-133G | 4592 | AGCTGAAACTTCTGG | [SEQ. ID. NO. 170] | C | 4865.2 |
| IL-18 A105C | 6085 | TCAAGCTTGCCAAAGTAATC | [SEQ. ID. NO. 171] | A | 6373.2 |

| Sequenom conditions for the polymorphisms genotyping -4 | | | | | |
|---|---|---|---|---|---|
| SNP_ID | EXT1_SEQ | EXT2_CALL | EXT2_MASS | EXT2_SEQ | 1st PAUSE |
| VDBP-420 | AGCTTTGCCAGTTCCT [SEQ. ID. NO. 172] | C | 5136.4 | AGCTTTGCCAGTTCCGT [SEQ. ID. NO. 173] | 4848.2 |
| VDBP-416 | AAAAGCAAAATTGCCTGAT [SEQ. ID. NO. 174] | G | 6456.2 | AAAAGCAAAATTGCCTGAGGC [SEQ. ID. NO. 175] | 5853.9 |
| ADRB2-Gln27Glu | CACGACGTCACGCAGC [SEQ. ID. NO. 176] | G | 5173.4 | CACGACGTCACGCAGGA [SEQ. ID. NO. 177] | 4876.2 |
| GSTP1-105 | ACCTCCGCTGCAAATACA [SEQ. ID. NO. 178] | G | 5716.7 | ACCTCCGCTGCAAATACGT [SEQ. ID. NO. 179] | 5428.5 |
| PAI1 G-675G | GAGTCTGGACACGTGGGGA [SEQ. ID. NO. 180] | G | 6247.1 | GAGTCTGGACACGTGGGGGA [SEQ. ID. NO. 181] | 5949.9 |
| IL-11 G518A | TCCATCTCTGTGGATCTCCA [SEQ. ID. NO. 182] | G | 6323.1 | TCCATCTCTGTGGATCTCCGT [SEQ. ID. NO. 183] | 6034.9 |
| NOS3-298 | TGCTGCAGGCCCCAGATGAT [SEQ. ID. NO. 184] | G | 6416.2 | TGCTGCAGGCCCCAGATGAGC [SEQ. ID. NO. 185] | 6143 |

-continued

Sequenom conditions for the polymorphisms genotyping -4

| SNP_ID | EXT1_SEQ | EXT2_CALL | EXT2_MASS | EXT2_SEQ | 1$^{st}$PAUSE |
|---|---|---|---|---|---|
| IL-8 A-251T | CACAATTTGGTGAATTATCAAT [SEQ. ID. NO. 186] | T | 7029.6 | CACAATTTGGTGAATTATCAAAT [SEQ. ID. NO. 187] | 6741.4 |
| IL-18 C-133G | AGCTGAAACTTCTGGC [SEQ. ID. NO. 188] | G | 5218.4 | AGCTGAAACTTCTGGGA [SEQ. ID. NO. 189] | 4921.2 |
| IL-18 A105C | TCAAGCTTGCCAAAGTAATCT [SEQ. ID. NO. 190] | C | 7040.6 | TCAAGCTTGCCAAAGTAATCGGA [SEQ. ID. NO. 191] | 6414.2 |

Results

Frequencies of individual polymorphisms are as follows:

TABLE 6

Polymorphism allele and genotype frequency in the OCOPD patients, exposed resistant smokers and controls.

Cyclo-oxygenase 2 −765 G/C

| Frequency | Allele* | | Genotype | | |
|---|---|---|---|---|---|
| | C | G | CC | CG | GG |
| Controls n = 95 (%) | 27 (14%) | 161 (86%) | 3 (3%) | 21 (22%) | 70 (75%) |
| OCOPD n = 82 (%) | 22 (13%) | 142[4] (87%) | 2 (2%) | 18 (22%) | 62[3] (76%) |
| Resistant n = 87 (%) | 42[2] (24%) | 132 (76%) | 6[1] (7%) | 30[1] (34%) | 51 (59%) |

Glutathione S Transferase P1 Ile 105 Val (A/G)

| Frequency | Allele* | | Genotype | | |
|---|---|---|---|---|---|
| | A | G | AA | AG | GG |
| Controls n = 186 (%) | 234 (63%) | 138 (37%) | 71 (38%) | 92 (50%) | 23 (12%) |
| OCOPD n = 123 (%) | 159 (65%) | 87 (36%) | 52 (42%) | 55 (45%) | 16[5] (13%) |
| Resistant n = 98 (%) | 136 (69%) | 60 (31%) | 44 (45%) | 48 (49%) | 6 (6%) |

Interleukin 18 105 C/A

| Frequency | Allele* | | Genotype | | |
|---|---|---|---|---|---|
| | C | A | CC | AC | AA |
| Controls n = 185 (%) | 119 (32%) | 251 (68%) | 22 (12%) | 75 (40%) | 88 (48%) |
| OCOPD n = 122 (%) | 62 (25%) | 182 (75%) | 12 (10%) | 38 (31%) | 72[6,7] (59%) |
| Resistant n = 98 (%) | 60 (31%) | 136 (69%) | 6 (6%) | 48 (49%) | 44 (45%) |

Interleukin 18 −133 G/C

| Frequency | Allele* | | Genotype | | |
|---|---|---|---|---|---|
| | G | C | GG | GC | CC |
| Controls n = 188 (%) | 121 (32%) | 255 (68%) | 23 (12%) | 75 (40%) | 90 (48%) |
| OCOPD n = 122 | 62 (25%) | 182 (75%) | 12 (10%) | 38 (31%) | 72[8,9] (59%) |
| Resistant n = 97 (%) | 60 (31%) | 134 (69%) | 6 (6%) | 48 (50%) | 43 (44%) |

Interleukin 8 −251 A/T

| Frequency | Allele* | | Genotype | | |
|---|---|---|---|---|---|
| | A | T | AA | AT | TT |
| Controls n = 188 (%) | 175 (47%) | 201 (53%) | 39 (21%) | 97 (52%) | 52 (28%) |
| OCOPD n = 116 | 101 (44%) | 131 (56%) | 21 (18%) | 59 (51%) | 36 (31%) |
| Resistant n = 93 (%) | 94[11] (50%) | 92 (49%) | 26[10] (28%) | 42 (45%) | 25 (27%) |

TABLE 6-continued

Polymorphism allele and genotype frequency in the OCOPD patients, exposed resistant smokers and controls.

Vitamin D Binding Protein Lys 420 Thr (A/C)

| Frequency | Allele* | | Genotype | | |
|---|---|---|---|---|---|
| | A | C | AA | AC | CC |
| Controls n = 189 (%) | 113 (30%) | 265 (70%) | 17 (9%) | 79 (42%) | 93 (49%) |
| OCOPD n = 122 (%) | 62 (25%) | 182 (75%) | 5 (4%) | 52 (43%) | 65[14] (53%) |
| Resistant n = 99 (%) | 73[13] (37%) | 125 (63%) | 12[12] (12%) | 49 (50%) | 38 (38%) |

Vitamin D Binding Protein Glu 416 Asp (T/G)

| Frequency | Allele* | | Genotype | | |
|---|---|---|---|---|---|
| | T | G | TT | TG | GG |
| Controls n = 189 (%) | 163 (43%) | 215 (57%) | 35 (19%) | 93 (49%) | 61 (32%) |
| OCOPD n = 122 (%) | 109 (45%) | 135 (55%) | 25 (21%) | 59 (48%) | 38[17] (31%) |
| Resistant n = 99 (%) | 103[16] (52%) | 95 (48%) | 23[15] (23%) | 57[15] (58%) | 19 (19%) |

Microsomal epxoide hydrolase R/r Exon 3 T/C

| Frequency | Allele* | | Genotype | | |
|---|---|---|---|---|---|
| | r | R | rr | Rr | RR |
| Controls n = 184 (%) | 228 (62%) | 140 (38%) | 77 (42%) | 74 (40%) | 33 (18%) |
| OCOPD n = 98 (%) | 144 (74%) | 52 (26%) | 55 (56%) | 34 (35%) | 9 (9%) |
| Resistant n = 102 (%) | 135 (66%) | 69 (34%) | 52 (51%) | 31 (30%) | 19[18] (19%) |

Super oxide dismutase 3 Arg 312 Gln

| Frequency | Allele* | | Genotype | | |
|---|---|---|---|---|---|
| | A | G | AA | AG | GG |
| Controls n = 190 (%) | 371 (98%) | 9 (2%) | 183 (96%) | 5 (3%) | 2 (1%) |
| OCOPD n = 100 (%) | 199[20] (99%) | 1 (1%) | 99 (99%) | 1 (1%) | 0 (0%) |
| Resistant n = 102 (%) | 193 (95%) | 11[20] (5%) | 92 (90%) | 9[19] (9%) | 1[19] (1%) | a1-antitrypsin S

| Frequency | Allele* | | Genotype | | |
|---|---|---|---|---|---|
| | M | S | MM | MS | SS |
| OCOPD n = 88 (%) | 171 (97%) | 5 (3%) | 83 (94%) | 5 (6%) | 0 (0%) |
| Resistant n = 94 (%) | 175 (93%) | 13[22] (7%) | 81 (86%) | 13[21] (14%) | 0 (0%) |

Toll-like receptor 4 Asp 299 Gly A/G

| Frequency | Allele* | | Genotype | | |
|---|---|---|---|---|---|
| | A | G | AA | AG | GG |
| OCOPD n = 60 (%) | 117 (98%) | 1 (2%) | 58 (98%) | 1 (2%) | 0 (0%) |
| Resistant n = 34 (%) | 65 (96%) | 3 (4%) | 31 (91%) | 3[23] (9%) | 0 (0%) |

Beta2-adrenoreceptor Gln 27 Glu

| Frequency | Allele* | | Genotype | | |
|---|---|---|---|---|---|
| | C | G | CC | CG | GG |
| Controls n = 186 (%) | 204 (55%) | 168 (45%) | 57 (31%) | 90 (48%) | 39 (21%) |
| OCOPD n = 122 (%) | 129 (53%) | 115 (47%) | 32 (26%) | 65 (53%) | 25 (21%) |
| Resistant n = 99 (%) | 117 (59%) | 81 (41%) | 38[24] (38%) | 41 (41%) | 20 (20%) |

Interleukin 11 (IL-11) −518 G/A

| Frequency | Allele* | | Genotype | | |
|---|---|---|---|---|---|
| | A | G | AA | AG | GG |
| OCOPD n = 119 (%) | 110 (46%) | 128 (54%) | 22 (19%) | 66 (55%) | 31 (26%) |
| Resistant n = 98 (%) | 103 (53%) | 93 (47%) | 26[25] (27%) | 51 (52%) | 21 (21%) |

TABLE 6-continued

Polymorphism allele and genotype frequency in the OCOPD patients, exposed resistant smokers and controls.

Interleukin-13 −1055 C/T

| Frequency | Allele* | | Genotype | | |
|---|---|---|---|---|---|
| | T | C | TT | TC | CC |
| Controls n = 182 (%) | 65 (18%) | 299 (82%) | 5 (3%) | 55 (30%) | 122 (67%) |
| OCOPD n = 121 (%) | 53 (22%) | 189 (78%) | $5^{26}$ (4%) | 43 (36%) | 73 (60%) |
| Resistant n = 97 (%) | 31 (16%) | 163 (84%) | 1 (1%) | 29 (30%) | 67 (69%) |

Plasminogen activator inhibitor 1 −675 4G/5G

| Frequency | Allele* | | Genotype | | |
|---|---|---|---|---|---|
| | 5G | 4G | 5G5G | 5G4G | 4G4G |
| Controls n = 186 (%) | 158 (42%) | 214 (58%) | 31 (17%) | 96 (52%) | 59 (32%) |
| OCOPD n = 122 (%) | $115^{28}$ (47%) | 129 (53%) | $29^{27}$ (24%) | 57 (47%) | 36 (30%) |
| Resistant n = 98 (%) | 76 (39%) | 120 (61%) | 14 (14%) | 48 (49%) | 36 (37%) |

Nitric oxide synthase 3 Asp 298 Glu (T/G)

| Frequency | Allele* | | Genotype | | |
|---|---|---|---|---|---|
| | T | G | TT | TG | GG |
| Controls n = 183 (%) | 108 (30%) | 258 (70%) | 13 (7%) | 82 (45%) | 88 (48%) |
| OCOPD n = 120 (%) | 71 (30%) | 169 (70%) | 10 (8%) | 51 (43%) | 59 (49%) |
| Resistant n = 99 (%) | 71 (36%) | 127 (64%) | $15^{29,30}$ (15%) | 41 (41%) | 43 (43%) | a1-antitrypsin 3' 1237 G/A (T/t)

| Frequency | Allele* | | Genotype | | |
|---|---|---|---|---|---|
| | T | t | TT | Tt | tt |
| Controls n = 178 (%) | 345 (97%) | 11 (3%) | 167 (94%) | 11 (6%) | 0 (0%) |
| COPD n = 61 (%) | 109 (89%) | $13 (11\%)^{32}$ | 50 (82%) | $9 (15\%)^{31}$ | $2 (3\%)^{31}$ |
| Resistant n = 35 (%) | 67 (96%) | 3 (4%) | 32 (91%) | 3 (9%) | 0 (0%) |

Matrix metalloproteinase 1 −1607 1G/2G

| Frequency | Allele* | | Genotype | | |
|---|---|---|---|---|---|
| | 1G | 2G | 1G1G | 1G2G | 2G2G |
| Controls n = 174 (%) | 214 (61%) | 134 (39%) | 68 (39%) | 78 (45%) | 28 (16%) |
| COPD n = 93 (%) | 90 (48%) | $96 (52\%)34$ | 24 (26%) | 42 (45%) | $27 (29\%)^{33}$ |
| Resistant n = 94 (%) | 99 (53%) | 89 (47%) | 25 (27%) | 49 (52%) | 20 (21%) |

*number of chromosomes (2n)

[1]Genotype. CC/CG vs GG for resistant vs OCOPD, Odds ratio (OR) = 2.2, 95% confidence limits = 1.1-4.8, $\chi^2$ (Yates corrected) = 4.76, P = 0.03, CC/CG = protective

[2]Allele. C vs G for resistant vs OCOPD, Odds ratio (OR) = 2.1, 95% confidence limits 1.1-3.8, $\chi^2$ (Yates corrected) = 5.65, p = 0.02. C = protective

[3]Genotype. GG vs CG/CC for OCOPD vs resistant, Odds ratio (OR) = 0.5, 95% confidence limits = 0.2-0.9, $\chi^2$ (Yates corrected) 4.76, P = 0.03. GG = susceptible

[4]Allele. G vs C for OCOPD vs resistant, Odds ratio (OR) = 0.5, 95% confidence limits 0.3-0.9, $\chi^2$ (Yates corrected) = 5.65, p = 0.02. G = susceptible

[5]Genotype. GG vs AG/AA for OCOPD vs resistant, Odds ratio (OR) = 2.3, 95% confidence limits = 0.8-6.9, $\chi^2$ (Yates uncorrected) = 2.88, p = 0.09. GG genotype = susceptible

[6]Genotype. AA vs AC/CC for OCOPD vs resistant, Odds ratio (OR) = 1.8, 95% confidence limits = 1.0-3.1, $\chi^2$ (Yates corrected) = 3.8, p = 0.05. AA = susceptibility

[7]Genotype. AA vs AC/CC for OCOPD vs controls, Odds ratio (OR) = 1.6, 95% confidence limits 1.0-2.6, $\chi^2$ (Yates uncorrected) = 3.86, p = 0.05. AA = susceptibility

[8]Genotype. CC vs CG/GG for OCOPD vs controls, Odds ratio (OR) = 1.6, 95% confidence limits = 1.0-2.6, $\chi^2$ (Yates uncorrected) = 3.68, p = 0.05. CC = susceptibility

[9]Genotype. CC vs CG/GG for OCOPD vs resistant, Odds ratio (OR) = 1.8, 95% confidence limits 1.0-3.2, $\chi^2$ (Yates corrected) = 4.10, p = 0.04. CC = susceptibility

[10]Genotype. AA vs AT/TT for OCOPD vs resistant, Odds ratio (OR) = 1.8, 95% confidence limits = 0.9-3.6, $\chi^2$ (Yates uncorrected) = 2.88, p = 0.09. AA = protective

[11]Allele. A vs T for OCOPD vs resistant, Odds ratio (OR) = 1.3, 95% confidence limits = 0.9-2.0, $\chi^2$ (Yates uncorrected) = 2.3, p = 0.15. A = protective

[12]Genotype. AA vs AC/CC for resistant vs OCOPD, Odds ratio (OR) = 3.2, 95% confidence limits = 1.0-11.0, $\chi^2$ (Yates corrected) = 3.89, p = 0.05. AA genotype = protective

[13]Allele. A vs C for resistant vs OCOPD, Odds ratio (OR) = 1.7, 95% confidence limits 1.1-2.6, $\chi^2$ (Yates corrected) = 6.24, p = 0.01. A allele = protective

[14]Genotype. CC vs AC/AA for OCOPD vs resistant, Odds ratio (OR) = 1.8, 95% confidence limits = 1.0-3.3, $\chi^2$ (Yates corrected) = 4.29, p = 0.04. CC genotype = susceptibility

TABLE 6-continued

Polymorphism allele and genotype frequency in the OCOPD patients, exposed resistant smokers and controls.

[15] Genotype. TT/TG vs GG for resistant vs OCOPD, Odds ratio (OR) = 1.9, 95% confidence limits = 1.0-38, $\chi^2$ (Yates uncorrected) = 4.08, p = 0.04. TT/TG genotype = protective
[16] Allele. T vs G for resistant vs OCOPD, Odds ratio (OR) = 1.3, 95% confidence limits 0.9-2.0, $\chi^2$ (Yates uncorrected) = 2.36, p = 0.12. A allele = protective
[17] Genotype. GG vs TT/TG for OCOPD vs resistant, Odds ratio (OR) = 0.5, 95% confidence limits = 0.3-1.0, $\chi^2$ (Yates uncorrected) = 4.1, p = 0.04. GG genotype = susceptible
[18] Genotype. RR vs Rr/rr for resistant vs OCOPD, Odds ratio (OR) = 2.3, 95% confidence limits = 0.9-5.8, $\chi^2$ (Yates uncorrected) = 3.7, p = 0.05, RR genotype = protective
[19] Genotype. AG/GG vs AA for resistant vs OCOPD, Odds ratio (OR) = 10.8, 95% confidence limits = 1.4-229, $\chi^2$ (Yates corrected) = 5.99 p = 0.01. AG/GG genotype = protective, AA susceptible
[20] Allele. G vs A for resistant vs OCOPD, Odds ratio (OR) = 11.3, 95% confidence limits 1.5-237, $\chi^2$ (Yates corrected) = 6.77, p = 0.001. G allele = protective, A susceptible
[21] Genotype. MS vs MM for Resistant vs OCOPD, Odds ratio (OR) = 2.7, 95% confidence limits 0.8-9.0, $\chi^2$ (Yates uncorrected) = 3.4, p = 0.07. MS = protective
[22] Allele: S vs M allele for resistant vs OCOPD, Odds ratio (OR) = 2.5, 95% confidence limits 0.8-8.4, $\chi^2$ (Yates uncorrected) 3.24, p = 0.07.
[23] Genotype AG vs AA in resistant vs OCOPD, Odd's Ratio (OR) = 5.61, 95% confidence limits 0.5-146, $\chi^2$ (Yates uncorrected) = 2.66, p = 0.10. AG = protective
[24] Genotype. CC vs CG/GG for resistant vs OOCOPD, Odds ratio (OR) = 1.75, 95% confidence limits = 1.0-3.2, $\chi^2$ (Yates uncorrected) = 3.73, p = 0.05. CC = protective
[25] Genotype: AA vs AG/GG for resistant vs OCOPD, Odd's Ratio (OR) = 1.6, 95% confidence limits 0.8-32, $\chi^2$ (Yates uncorrected) = 2.02, p = 0.16. AA = protective
[26] Genotype. TT vs TC/CC for OCOPD vs resistant, Odds ratio (OR) = 6.03, 95% confidence limits 1.1-42, $\chi^2$ (Yates corrected) = 4.9, p = 0.03. TT = susceptible
[27] Genotype. 5G5G vs rest for OCOPD vs resistant, Odds ratio (OR) = 1.9, 95% confidence limits 0.9-4.0, $\chi^2$ (Yates uncorrected) = 3.11, p = 0.08. 5G5G = susceptible
[28] Allele. 5G vs 4G for OCOPD vs resistant, Odds ratio (OR) = 1.4, 95% confidence limits 0.9-2.1, $\chi^2$ (Yates corrected) = 3.1, p = 0.08. 5G = susceptible
[29] Genotype. TT vs TG/GG for resistant vs controls, Odds ratio (OR) = 2.3, 95% confidence limits 1.0-5.5, $\chi^2$ (Yates corrected) = 3.80, p = 0.05. TT genotype = protective
[30] Genotype. TT vs TG/GG for resistant vs OCOPD, Odds ratio (OR) = 1.9, 95% confidence limits 0.8-5.0, $\chi^2$ (Yates uncorrected) = 2.49, p = 0.11. TT genotype = protective
[31] Genotype: Tt/tt vs TT for COPD vs controls, Odd's Ratio (OR) = 3.34, 95% confidence limits 1.3-8.9, $\chi^2$ (Yates corrected) = 6.28, p = 0.01. Tt/tt = susceptible to OCOPD
[32] Allele: t vs T for COPD vs controls, Odd's Ratio (OR) = 2.5, 95% confidence limits 1.0-6.3, $\chi^2$ (Yates corrected) = 4.1, p = 0.04. t = susceptible to OCOPD
[33] Genotype. 2G2G vs 1G1G/1G2G for COPD vs controls, Odds ratio (OR) = 2.1, 95% confidence limits 1.1-4.1, $\chi^2$ (Yates corrected) = 5.44, p = 0.02. 2G2G genotype = susceptible for OCOPD
[34] Allele. 2G vs 1G for COPD vs controls, Odds ratio (OR) = 1.7, 95% confidence limits 1.2-2.5, $\chi^2$ (Yates corrected) = 7.97, p = 0.005. 2G = susceptible for OCOPD Table 7 below provides a summary of the protective and susceptibility polymorphisms determined for OCOPD.

TABLE 7

Summary of protective and susceptibility polymorphisms for OCOPD

| Gene | Polymorphism | Role |
|---|---|---|
| Cyclo-oxygenase (Cox) 2 | Cox 2 –765 G/G | CC/CG protective<br>GG susceptible |
| β2-adrenoreceptor (ADRB2) | ADRB2 Gln 27Glu | CC protective |
| Interleukin-18 (IL-18) | IL-18 –133 C/C | CC susceptible |
| Interleukin-18 (IL-18) | IL-18 105 A/C | AA susceptible |
| Plasminogen activator inhibitor 1 (PAI-1) | PAI-1 –675 4G/5G | 5G5G susceptible |
| Nitric Oxide synthase 3 (NOS3) | NOS3 298 Asp/Glu | TT protective |
| Vitamin D Binding Protein (VDBR) | VDBR Lys 420 Thr | AA protective<br>CC susceptible |
| Vitamin D Binding Protein (VDBR) | VDBP Glu 416 Asp | TT/TG protective<br>GG susceptible |
| Glutathione S Transferase (GSTP1) | GSTP1 Ile105Val | GG susceptible |
| Superoxide dismutase 3 (SOD3) | SOD3 Arg 312 Gln | AG/GG protective<br>AA susceptible |
| a1-antitrypsin (a1AT) | a1AT 3' 1237 G/A (T/t) | Tt/tt susceptible |
| a1-antitrypsin (a1AT) | a1AT S allele | MS protective |
| Toll-like receptor 4 (TLR4) | TLR4 Asp 299 Gly A/G | AG/GG protective |
| Interleukin-8 (IL-8) | IL-8 –251 A/T | AA protective |
| Interleukin 11 (IL-11) | IL-11 –518 G/A | AA protective |
| Microsomal epoxide hydrolase (MEH) | MEH Exon 3 T/C (r/R) | RR protective |
| Interleukin 13 (IL-13) | IL-13 –1055 C/T | TT susceptible |
| Matrix Metalloproteinase 1 (MMP1) | MMP1 –1607 1G/2G | 2G2G susceptible |

The combined frequencies of the presence or absence of the selected protective genotypes COX2 –765 CC/CG, NOS3 298 TT, a1AT MS/SS, SOD3 AG/GG, MEH Exon 3 RR, and VDBP 420 AA observed in the OCOPD subjects and in resistant smokers is presented below in Table 8.

TABLE 8

Combined frequencies of the presence or absence of
protective genotypes in OCOPD subjects
and in resistant smokers.

| Cohorts | Number of protective polymorphisms | | | Total |
|---|---|---|---|---|
| | 0 | 1 | =2 | |
| OCOPD | 34 (27%) | 51 (41%) | 39 (32%) | 124 |
| Resistant smokers | 20 (19%) | 31 (30%) | 53 (51%) | 104 |
| % of smokers with OCOPD | 34/54 (63%) | 51/82 (62%) | 39/92 (42%) | |

| Comparison | Odd's ratio | 95% CI | ?2 | P value |
|---|---|---|---|---|
| 0 vs 1 · vs 2+, Resist vs OCOPD | — | — | 16.2 | 0.003 |
| 2+ vs 0-1, Resist vs OCOPD | 2.3 | 1.3-4.0 | 8.15 | 0.004 |
| 0 vs 2+, OCOPD vs Resist | 2.3 | 1.1-4.9 | 4.97 | 0.03 |

The combined frequencies of the presence or absence of the selected susceptibility genotypes MMP1 −1607 2G2G, GSTP1 105 GG, PAI-1 −675 5G5G, IL-13 −1055 TT, and VDBP 416 GG, observed in the OCOPD subjects and in resistant smokers is presented below in Table 9.

TABLE 9

Combined frequencies of the presence or absence of
selected susceptibility genotypes in OCOPD
subjects and in resistant smokers.

| Cohorts | Number of protective polymorphisms | | | Total |
|---|---|---|---|---|
| | 0 | 1 | =2 | |
| OCOPD | 45 (36%) | 55 (44%) | 24 (20%) | 124 |
| Resistant smokers | 55 (54%) | 37 (37%) | 9 (9%) | 101 |
| % of smokers with OCOPD | 45/100 (45%) | 55/92 (60%) | 24/33 (73%) | |

| Comparison | Odd's ratio | 95% CI | ?2 | P value |
|---|---|---|---|---|
| 0 vs 1 vs 2+, OCOPD vs Resist | — | — | 9.1 | 0.01 |
| 2+ vs 0-1, OCOPD vs Resist | 2.5 | 1.0-6.0 | 4.05 | 0.04 |
| 0+ vs 1-2+, Resist vs OCOPD | 2.1 | 1.2-3.7 | 6.72 | 0.01 |

Figure 3:
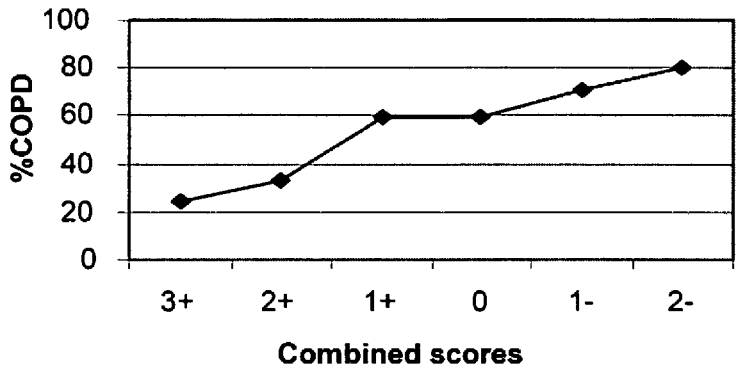
FIG. 3: depicts a graph showing net scores for protective and susceptibility polymorphisms in OCOPD subjects.

Protective polymorphisms were assigned a score of +1 while susceptibility polymorphisms were assigned a score of −1. For each subject, a net score was then calculated according to the presence of susceptibility and protective genotypes. This produced a linear spread of values, as shown in Table 10. When assessed as a range between −2 to +3, a linear relationship as depicted in FIG. 3 was observed. This analysis indicates that for subjects with a net score of −1 or less, there was an approximately 70% or greater risk of having OCOPD. In contrast, for subjects with a net score of 2+ or greater, the risk was approximately 25% (see FIG. 3). As a point of clarification, it is noted that FIG. 3 depicts the sum of the protective and susceptibility polymorphisms combined, rather than simply the sum of the protective polymorphisms in one graph and the sum of the susceptibility polymorphisms in another graph. Thus, the SNP score can be negative if there are only susceptibility polymorphisms, positive, if there are only protective polymorphisms, or either positive or negative, depending upon the relative numbers of protective to susceptibility polymorphisms.

TABLE 10

Combined presence or absence of protective and susceptibility
polymorphisms

| | Score combining protective Vand susceptibility polymorphisms | | | | | |
|---|---|---|---|---|---|---|
| | −2 | −1 | 0 | 1 | 2 | 3 |
| OCOPD n = 124 | 8 | 28 | 33 | 39 | 11 | 5 |
| Resistant n = 101 | 2 | 11 | 23 | 27 | 23 | 15 |
| % OCOPD | 80% | 72% | 59% | 59% | 32% | 25% |

II. Example 3

Case Association Study—Lung Cancer

Methods

Subject Recruitment

Subjects of European decent who had smoked a minimum of fifteen pack years and diagnosed with lung cancer were recruited. Subjects met the following criteria: diagnosed with lung cancer based on radiological and histological grounds, including primary lung cancers with histological types of small cell lung cancer, squamous cell lung cancer, adenocarinoma of the lung, non-small cell cancer (where histological markers can not distinguish the subtype) and broncho-alveolar carcinoma. Subjects can be of any age and at any stage of treatment after the diagnosis had been confirmed. One hundred and nine subjects were recruited, of these 58% were male, the mean FEV1/FVC (±95% confidence limits) was 51% (49-53), mean FEV1 as a percentage of predicted was 43 (41-45). Mean age, cigarettes per day and pack year history was 65 yrs (64-66), 24 cigarettes/day (22-25) and 50 pack years (41-55) respectively. Two hundred and seventeen European subjects who had smoked a minimum of twenty pack years and who had never suffered breathlessness and had not been diagnosed with an obstructive lung disease or lung cancer in the past were also studied. This control group was recruited through clubs for the elderly and consisted of 63% male, the mean FEV1/FVC (95%CI) was 82% (81-83), mean FEV1as a percentage of predicted was 96 (95-97). Mean age, cigarettes per day and pack year history was 59 yrs (57-61), 24 cigarettes/day (22-26) and 42 pack years (39-45) respectively. Using a PCR based method [1], all subjects were genotyped for the α1-antitrypsin mutations (S and Z alleles) and those with the ZZ allele were excluded. 190 European blood donors (smoking status unknown) were recruited consecutively through local blood donor services. Sixty-three percent were men and their mean age was 50 years. On regression analysis, the age difference and pack years difference observed between lung cancer sufferers and resistant smokers was found not to determine FEV or lung cancer.

This study shows that polymorphisms found in greater frequency in lung cancer patients compared to resistant smokers can reflect an increased susceptibility to the development of lung cancer. Similarly, polymorphisms found in greater frequency in resistant smokers compared to lung cancer can reflect a protective role.

Summary of characteristics.

| Parameter Median (IQR) | Lung Cancer N = 109 | Resistant smokers N = 200 | Differences |
|---|---|---|---|
| % male | 52% | 64% | ns |
| Age (yrs) | 68 (11) | 60 (12) | $P < 0.05$ |
| Pack years | 40 (31) | 43 (25) | $P < 0.05$ |
| Cigarettes/day | 18 (11) | 24 (12) | ns |
| FEV1 (L) | 1.7 (0.6) | 2.8 (0.7) | $P < 0.05$ |
| FEV1 % predict | 67 (22) | 96% (10) | $P < 0.05$ |
| FEV1/FVC | 59 (14) | 82 (8) | $P < 0.05$ |

Means and 95% confidence limits

Glutathione S-transferase Null Polymorphisms Genotyping

Genomic DNA was extracted using standard phenol and chloroform methods. Cohorts of patients and controls were configured in to 96-well PCR format containing strategic negative controls. The assay primers, PCR conditions and RFLP assays details have been previously described [7, herein incorporated by reference in its entirety]. Genotyping was done using minor modifications of the above protocol optimized for our own laboratory conditions The PCR reactions were amplified in MJ Research thermocyclers in a total volume of 25 μl and contained 80 ng genomic DNA, 100 ng forward and reverse primers, 200 mM dNTPs, 20 mM Tris-HCL (pH 8.4), 50 mM KCl, 2.5 mM MgCl2 and 1.0 unit of Taq polymerase (Qiagen). Forward, internal (GSTM4) and reverse prime sequences were 5' CTGCCCTACTTGAT-TGATGG-3' [SEQ.ID.NO.192], 5' ATCTTCTCCTCTTCT-GTCTC -3' [SEQ.ID.NO.193] and 5'-TTCTGGATTGTAG-CAGATCA -3' [SEQ.ID.NO.194]. Cycling conditions consisted of 94 C 60 s, 59C 30 s, 72 C 30 s for 35 cycles with an extended last extension of 3 min. Digested products were separated on 3% agarose gel. The products were visualized by ultraviolet transillumination following ethidium bromide staining and migration compared against a 1 Kb plus ladder standard (Invitrogen). Genotypes were recorded in data spreadsheets and statistical analysis performed.

Cyclooxygenase 2 Polymorphisms Genotyping

Genomic DNA was extracted from whole blood samples (Maniatis, T., Fritsch, E. F. and Sambrook, J., Molecular Cloning Manual. 1989). The Cyclo-oxygenase 2 -765 polymorphism was determined by minor modifications of a previously published method (Papafili A, et al., 2002, incorporated in its entirety herein by reference)). The PCR reaction was carried out in a total volume of 25 μl and contained 20 ng genomic DNA, 500 pmol forward and reverse primers, 0.2 mM dNTPs, 10 mM Tris-HCL (pH 8.4), 150 mM KCl, 1.0 mM MgCl$_2$ and 1 unit of polymerase (Life Technologies). Cycling times were incubations for 3 min at 95° C. followed by 33 cycles of 50 s at 94° C., 60 s at 66° C. and 60 s at 72° C. A final elongation of 10 min at 72° C. then followed. 4 ul of PCR products were visualized by ultraviolet trans-illumination of a 3% agarose gel stained with ethidium bromide. An aliquot of 3 ul of amplification product was digested for 1 hr with 4 units of AciI (Roche Diagnostics, New Zealand) at 37° C. Digested products were separated on a 2.5% agarose gel run for 2.0 hours at 80 mV with TBE buffer. The products were visualized against a 123 bp ladder using ultraviolet transillumination after ethidium bromide staining.

Matrix Metalloproteinase 1 -1607 1G/2G Polymorphisms Genotyping

Genomic DNA was extracted using standard phenol and chloroform methods. Cohorts of patients and controls were configured in to 96-well PCR format containing strategic negative controls. The assay primers, PCR conditions and RFLP assays details have been previously described (Dunleavey, L. et al. Rapid genotype analysis of the matrix metalloproteinase-1 gene 1G/2G polymorphism that is associated with risk of cancer. *Matrix Biol.* 19(2):175-7 (2000), herein incorporated by reference in its entirety). Genotyping was done using minor modifications of the above protocol optimized for our own laboratory conditions The PCR reactions were amplified in MJ Research thermocyclers in a total volume of 25 μl and contained 80 ng genomic DNA, 100 ng forward and reverse primers, 200 mM dNTPs, 20 mM Tris-HCL (pH 8.4), 50 mM KCl, 1.5 mM MgCl$_2$ and 1.0 unit of Taq polymerase (Qiagen). Forward and reverse prime sequences were 3' TCGTGAGAATGTCTTCCCATT-3' [SEQ.ID.NO.195] and 5'-TCTTGGATTGATTTGAGATAAGT-GAAATC-3' [SEQ.ID.NO.196]. Cycling conditions consisted of 94 C 60 s 55C 30 s, 72 C 30 s for 35 cycles with an extended last extension of 3 min. Aliquots of amplification product were digested for 4 hrs with 6 Units of the restriction enzymes XmnI (Roche Diagnostics, New Zealand) at designated temperature conditions. Digested products were separated on 6% polyacrylamide gel. The products were visualized by ultraviolet transillumination following ethidium bromide staining and migration compared against a 11 Kb plus ladder standard (Invitrogen). Genotypes were recorded in data spreadsheets and statistical analysis performed.

Polymorphism Genotyping Using the Sequenom Autoflex Mass Spectrometer

Genomic DNA was extracted from whole blood samples [2]. Purified genomic DNA was aliquoted (10 ng/ul concentration) into 96 well plates and genotyped on a Sequenom™ system (SequenomTM Autoflex Mass Spectrometer and Samsung 24 pin nanodispenser) using the following sequences, amplification conditions and methods. The following conditions were used for the PCR multiplex reaction: final concentrations were for 10× Buffer 15 mM MgCl2 1.25×, 25 mM MgCl2 1.625 mM, dNTP mix 25 mM 500 uM, primers 4 uM 100 nM, Taq polymerase (Quiagen hot start) 0.15 U/reaction, Genomic DNA 10 ng/ul. Cycling times were 95° C. for 15 min, (5° C. for 15 s, 56° C. 30 s, 72° C. 30 s for 45 cycles with a prolonged extension time of 3 min to finish. We used shrimp alkaline phosphotase (SAP) treatment (2 ul to 5 ul per PCR reaction) incubated at 35° C. for 30 min and extension reaction (add 2 ul to 7 ul after SAP treatment) with the following volumes per reaction of: water, 0.76 ul; hME 10× termination buffer, 0.2 ul; hME primer (10 uM), 1 ul; MassEXTEND enzyme, 0.04 ul.

Sequenom conditions for the polymorphisms genotyping -1

| TERM SNP_ID | $2^{nd}$-PCRP | $1^{st}$-PCRP |
|---|---|---|
| ACT CYP2E1_1019G/CPst1 | ACGTTGGATGAAACCAGAGGGAAGCAAAGG [SEQ. ID. NO. 197] | ACGTTGGATGTCATTGGTTGTGCTGCACCT [SEQ. ID. NO. 198] |
| ACT XPD-751 G/T | ACGTTGGATGCACCAGGAACCGTTTATGGC [SEQ. ID. NO. 199] | ACGTTGGATGAGCAGCTAGAATCAGAGGAG [SEQ. ID. NO. 200] |

Sequenom conditions for the polymorphisms genotyping -1

| TERM SNP_ID | 2nd-PCRP | 1st-PCRP |
|---|---|---|
| ACT IL-18 105 A/C | ACGTTGGATGGTCAATGAAGAGAACTTGGTC [SEQ. ID. NO. 201] | ACGTTGGATGAATGTTTATTGTAGAAAACC [SEQ. ID. NO. 202] |
| ACT IL-18-133 G/C | ACGTTGGATGGGGTATTCATAAGCTGAAAC [SEQ. ID. NO. 203] | ACGTTGGATGCCTTCAAGTTCAGTGGTCAG [SEQ. ID. NO. 204] |
| ACT CYP 1A1 IIe462Val | ACGTTGGATGGTGATTATCTTTGGCATGGG [SEQ. ID. NO. 205] | ACGTTGGATGGGATAGCCAGGAAGAGAAAG [SEQ. ID. NO. 206] |
| ACT MMP12 Asn 357 Ser A/G | ACGTTGGATGCCCTATTTCTTTGTCTTCAC [SEQ. ID. NO. 207] | ACGTTGGATGCTTGGGATAATTTGGCTCTG [SEQ. ID. NO. 208] |
| ACT OGG1 Ser 326 Cys G/C | ACGTTGGATGGGAACCCTTTCTGCGCTTTG [SEQ. ID. NO. 209] | ACGTTGGATGCCTACAGGTGCTGTTCAGTG [SEQ. ID. NO. 210] |
| ACT NAT2 Arg 197 Gln A/G | ACGTTGGATGCCTGCCAAAGAAGAAACACC [SEQ. ID. NO. 211] | ACGTTGGATGACGTCTGCAGGTATGTATTC [SEQ. ID. NO. 212] |
| ACT CYP2E1_C/T Rsa1 | ACGTTGGATGGTTCTTAATTCATAGGTTGC [SEQ. ID. NO. 213] | ACGTTGGATGCTTCATTTCTCATCATATTTTC [SEQ. ID. NO. 214] |
| ACG CCND1 A870G | ACGTTGGATGTAGGTGTCTCCCCCTGTAAG [SEQ. ID. NO. 215] | ACGTTGGATGTCCTCTCCAGAGTGATCAAG [SEQ. ID. NO. 216] |
| ACG ILB1-511 A/G | ACGTTGGATGATTTTCTCCTCAGAGGCTCC [SEQ. ID. NO. 217] | ACGTTGGATGTGTCTGTATTGAGGGTGTGG [SEQ. ID. NO. 218] |
| ACG FAS_A-670G | ACGTTGGATGTTGTGGCTGCAACATGAGAG [SEQ. ID. NO. 219] | ACGTTGGATGCTATGGCGCAACATCTGTAC [SEQ. ID. NO. 220] |
| ACG NOS3-786 T/C | ACGTTGGATGACTGTAGTTTCCCTAGTCCC [SEQ. ID. NO. 221] | ACGTTGGATGAGTCAGCAGAGAGACTAGGG [SEQ. ID. NO. 222] |
| ACT ACT_Ala15Thr | ACGTTGGATGGAGTTGAGAATGGAGAGAATG [SEQ. ID. NO. 223] | ACGTTGGATGTCAAGTGGGCTGTTAGGGTG [SEQ. ID. NO. 224] |
| ACT SOD3 Arg 312 Gln | ACGTTGGATGTGCTGCGTGGTGGGCGTGTG [SEQ. ID. NO. 225] | ACGTTGGATGGGCCTTGCACTCGCTCTCG [SEQ. ID. NO. 226] |
| ACT NOS3 Asp 298 Glu | ACGTTGGATGAAACGGTCGCTTCGACGTGC [SEQ. ID. NO. 227] | ACGTTGGATGACCTCAAGGACCAGCTCGG [SEQ. ID. NO. 228] |
| CGT IL-8-251 A/T | ACGTTGGATGACTGAAGCTCCACAATTTGG [SEQ. ID. NO. 229] | ACGTTGGATGGCCACTCTAGTACTATATCTG [SEQ. ID. NO. 230] |
| CGT IFN gamma 874 A/T | ACGTTGGATGCAGACATTCACAATTGATTT [SEQ. ID. NO. 231] | ACGTTGGATGGATAGTTCCAAACATGTGCG [SEQ. ID. NO. 232] |
| ACT XRCC1 Arg 399 Gln G/A | ACGTTGGATGTAAGGAGTGGGTGCTGGACT [SEQ. ID. NO. 233] | ACGTTGGATGAGGATAAGGAGCAGGGTTGG [SEQ. ID. NO. 234] |

Sequenom conditions for the polymorphisms genotyping-2

| SNP_ID | AMP_LEN | UP_CONF | MP_CONF | Tm(NN) | PcGC | PWARN | UEP_DIR | UEP_MASS |
|---|---|---|---|---|---|---|---|---|
| CYP2E1_1019G/CPst1 | 119 | 95.2 | 71.3 | 46.7 | 47.1 | | F | 5256.4 |
| XPD −751 G/T | 113 | 97.6 | 71.3 | 49.8 | 47.4 | | F | 5689.7 |
| IL-18 105 A/C | 120 | 65.6 | 71.3 | 49.8 | 36.4 | | R | 6702.4 |
| IL-18 −133 G/C | 112 | 93.5 | 81.3 | 47.1 | 42.1 | | F | 5811.8 |
| CYP 1A1 Ile462Val | 102 | 98.2 | 81.3 | 55.6 | 55 | | F | 6222.1 |
| MMP12 Asn 357 Ser A/G | 95 | 92.6 | 81.3 | 48 | 30.4 | | F | 7070.6 |
| OGG1 Ser 326 Cys G/C | 99 | 96.5 | 82.2 | 58.9 | 70.6 | | R | 5227.4 |
| NAT2 Arg 197 Gln A/G | 115 | 97.4 | 70 | 48.5 | 36.4 | | F | 6635.3 |
| CYP2E1_C/T Rsa1 | 105 | 62.8 | 77.8 | 46.4 | 26.1 | | R | 7018.6 |
| CCND1 A870G | 106 | 98.1 | 83 | 45.8 | 47.1 | | R | 5034.3 |
| ILB1 −511 A/G | 111 | 99.2 | 83 | 46 | 47.1 | | R | 5203.4 |
| FAS_A-670G | 103 | 99.2 | 83 | 54.4 | 50 | | R | 6166 |
| NOS3 −786 T/C | 114 | 97.5 | 83 | 61.8 | 61.9 | | F | 6358.1 |

Sequenom conditions for the polymorphisms genotyping-2

| SNP_ID | AMP_LEN | UP_CONF | MP_CONF | Tm(NN) | PcGC | PWARN | UEP_DIR | UEP_MASS |
|---|---|---|---|---|---|---|---|---|
| ACT_Ala15Thr | 118 | 93.4 | 68.2 | 45.2 | 47.1 | | F | 5136.4 |
| SOD3 Arg 312 Gln | 119 | 63.2 | 68.2 | 55.5 | 57.9 | | F | 5855.8 |
| NOS3 Asp 298 Glu | 113 | 82.2 | 68.2 | 65.4 | 66.7 | | F | 6432.2 |
| IL-8 –251 A/T | 119 | 92.6 | 75.8 | 45.9 | 28.6 | | R | 6428.2 |
| IFN gamma 874 A/T | 112 | 75.3 | 75.8 | 46.4 | 26.1 | | F | 6943.6 |
| XRCC1 Arg 399 Gln G/A | 109 | 93.6 | 93.6 | 66.8 | 82.4 | | F | 5099.3 |

Sequenom conditions for the polymorphisms genotyping -3

| SNP_ID | UEP_SEQ | EXT1 CALL | EXT1 MASS | EXT1_SEQ | EXT2 CALL |
|---|---|---|---|---|---|
| CYP2E1_1019G/CPst1 | TTCTTGGTTCAGGAGAG [SEQ. ID. NO. 235] | C | 5529.6 | TTCTTGGTTCAGGAGAGC [SEQ. ID. NO. 236] | G |
| XPD-751 G/T | GCAATCTGCTCTATCCTCT [SEQ. ID. NO. 237] | T | 5977.9 | GCAATCTGCTCTATCCTCTT [SEQ. ID. NO. 238] | G |
| IL-18 105 A/C | ATTCAAGCTTGCCAAAGTAATC [SEQ. ID. NO. 239] | A | 6990.6 | ATTCAAGCTTGCCAAAGTAATCT [SEQ. ID. NO. 240] | C |
| IL-18-133 G/C | CATAAGCTGAAACTTCTGG [SEQ. ID. NO. 241] | C | 6085 | CATAAGCTGAAACTTCTGGC [SEQ. ID. NO. 242] | G |
| CYP 1A1 IIe462Val | GGAAGTGTATCGGTGAGACC [SEQ. ID. NO. 243] | A | 6519.3 | GGAAGTGTATCGGTGAGACCA [SEQ. ID. NO. 244] | G |
| MMP12 Asn 357 Ser A/G | TGACAAATACTGGTTAATTAGCA [SEQ. ID. NO. 245] | A | 7367.8 | TGACAAATACTGGTTAATTAGCAA [SEQ. ID. NO. 246] | G |
| OGG1 Ser 326 Cys G/C | GCTCCTGAGCATGGCGG [SEQ. ID. NO. 247] | G | 5500.6 | GCTCCTGAGCATGGCGGC [SEQ. ID. NO. 248] | C |
| NAT2 Arg 197 Gln A/G | TACTTATTTACGCTTGAACCTC [SEQ. ID. NO. 249] | A | 6932.5 | TACTTATTTACGCTTGAACCTCA [SEQ. ID. NO. 250] | G |
| CYP2E1_C/T Rsa1 | CTTAATTCATAGGTTGCAATTTT [SEQ. ID. NO. 251] | T | 7315.8 | CTTAATTCATAGGTTGCAATTTTA [SEQ. ID. NO. 252] | C |
| CCND1 A870G | ACATCACCCTCACTTAC [SEQ. ID. NO. 253] | G | 5307.5 | ACATCACCCTCACTTACC [SEQ. ID. NO. 254] | A |
| ILB1-511 A/G | AATTGACAGAGAGCTCC [SEQ. ID. NO. 255] | G | 5476.6 | AATTGACAGAGAGCTCCC [SEQ. ID. NO. 256] | A |
| FAS_A-670G | ATGAGAGGCTCACAGACGTT [SEQ. ID. NO. 257] | G | 6439.2 | ATGAGAGGCTCACAGACGTTC [SEQ. ID. NO. 258] | A |
| NOS3-786 T/C | GGCATCAAGCTCTTCCCTGGC [SEQ. ID. NO. 259] | C | 6631.3 | GGCATCAAGCTCTTCCCTGGCC [SEQ. ID. NO. 260] | T |
| ACT_Ala15Thr | GAATGTTACCTCTCCTG [SEQ. ID. NO. 261] | A | 5433.6 | GAATGTTACCTCTCCTGA [SEQ. ID. NO. 262] | G |
| SOD3 Arg 312 Gln | GCACTCAGAGCGCAAGAAG [SEQ. ID. NO. 263] | C | 6129 | GCACTCAGAGCGCAAGAAGC [SEQ. ID. NO. 264] | G |
| NOS3 Asp 298 Glu | GCTGCTGCAGGCCCCAGATGA [SEQ. ID. NO. 265] | T | 6720.4 | GCTGCTGCAGGCCCCAGATGAT [SEQ. ID. NO. 266] | G |
| IL-8-251 A/T | CACAATTTGGTGAATTATCAA [SEQ. ID. NO. 267] | A | 6716.4 | CACAATTTGGTGAATTATCAAT [SEQ. ID. NO. 268] | T |
| IFN gamma 874 A/T | TTCTTACAACACAAAATCAAATC [SEQ. ID. NO. 269] | T | 7231.8 | TTCTTACAACACAAAATCAAATCT [SEQ. ID. NO. 268] | A |
| XRCC1 Arg 399 Gln G/A | TCGGCGGCTGCCCTCCC [SEQ. ID. NO. 271] | A | 5396.5 | TCGGCGGCTGCCCTCCCA [SEQ. ID. NO. 272] | G |

| Sequenom conditions for the polymorphisms genotyping -4 | | | |
|---|---|---|---|
| SNP_ID | EXT2_MASS | EXT2_SEQ | 1st PAUSE |
| CYP2E1_1019G/CPst1 | 5873.8 | TTCTTGGTTCAGGAGAGGT [SEQ. ID. NO. 273] | 5585.6 |
| XPD-751 G/T | 6292.1 | GCAATCTGCTCTATCCTCTGC [SEQ. ID. NO. 274] | 6018.9 |
| IL-18 105 A/C | 7658 | ATTCAAGCTTGCCAAAGTAATCGGA [SEQ. ID. NO. 275] | 7031.6 |
| IL-18-133 G/C | 6438.2 | CATAAGCTGAAACTTCTGGGA [SEQ. ID. NO. 276] | 6141 |
| CYP 1A1 IIe462Val | 6839.5 | GGAAGTGTATCGGTGAGACCGT [SEQ. ID. NO. 277] | 6551.3 |
| MMP12 Asn 357 Ser A/G | 7688 | TGACAAATACTGGTTAATTAGCAGT [SEQ. ID. NO. 278] | 7399.8 |
| OGG1 Ser 326 Cys G/C | 5853.8 | GCTCCTGAGCATGGCGGGA [SEQ. ID. NO. 279] | 5556.6 |
| NAT2 Arg 197 Gln A/G | 7261.8 | TACTTATTTACGCTTGAACCTCGA [SEQ. ID. NO. 280] | 6964.5 |
| CYP2E1_C/T Rsa1 | 7636 | CTTAATTCATAGGTTGCAATTTTGT [SEQ. ID. NO. 281] | 7347.8 |
| CCND1 A870G | 5651.7 | ACATCACCCTCACTTACTG [SEQ. ID. NO. 282] | 5338.5 |
| ILB1-511 A/G | 5820.8 | AATTGACAGAGAGCTCCTG [SEQ. ID. NO. 283] | 5507.6 |
| FAS_A-670G | 6743.4 | ATGAGAGGCTCACAGACGTTTC [SEQ. ID. NO. 284] | 6470.2 |
| NOS3-786 T/C | 6975.5 | GGCATCAAGCTCTTCCCTGGCTG [SEQ. ID. NO. 285] | 6662.3 |
| ACT_Ala15Thr | 5738.7 | GAATGTTACCTCTCCTGGC [SEQ. ID. NO. 286] | 5465.6 |
| SOD3 Arg 312 Gln | 7116.6 | GCACTCAGAGCGCAAGAAGGGGC [SEQ. ID. NO. 287] | 6185 |
| NOS3 Asp 298 Glu | 7034.6 | GCTGCTGCAGGCCCCAGATGAGC [SEQ. ID. NO. 288] | 6761.4 |
| IL-8-251 A/T | 7029.6 | CACAATTTGGTGAATTATCAAAT [SEQ. ID. NO. 289] | 6741.4 |
| IFN gamma 874 A/T | 7530 | TTCTTACAACACAAAATCAAATCAC [SEQ. ID. NO. 290] | 7256.8 |
| XRCC1 Arg 399 Gln G/A | 6054.9 | TCGGCGGCTGCCCTCCCGGA [SEQ. ID. NO. 291] | 5428.5 |

| Sequenom conditions for the polymorphisms genotyping -5 | | | |
|---|---|---|---|
| TERM | SNP_ID | 2nd-PCRP | 1st-PCRP |
| ACT | CTGF-447G/C | ACGTTGGATGAGGTAGCTGAAGAGGCAAAC [SEQ. ID. NO. 292] | ACGTTGGATGGCCTATAGCCTCTAAAACGC [SEQ. ID. NO. 293] |
| ACT | NBS1 Gln185Glu G/C | ACGTTGGATGCTTTCAATTTGTGGAGGCTG [SEQ. ID. NO. 294] | ACGTTGGATGTGTGCACTCATTTGTGGACG [SEQ. ID. NO. 295] |
| ACT | MBL2 161 G/A | ACGTTGGATGGTAGCTCTCCAGGCATCAAC [SEQ. ID. NO. 296] | ACGTTGGATGGTACCTGGTTCCCCCTTTTC [SEQ. ID. NO. 297] |

Sequenom conditions for the polymorphisms genotyping -5

| TERM | SNP_ID | 2nd-PCRP | 1st-PCRP |
|---|---|---|---|
| ACT | IGF2R Leu252Val C/G | ACGTTGGATGACACCAGGCGTTTGATGTTG [SEQ. ID. NO. 298] | ACGTTGGATGAAAAACGCCAACAGCATCGG [SEQ. ID. NO. 299] |
| ACT | MUC5AC-221 C/T | ACGTTGGATGAGGCGGAGATGGGTGTGTC [SEQ. ID. NO. 300] | ACGTTGGATGAGTCTAGGGTGGGGTATGTG [SEQ. ID. NO. 301] |
| ACT | Arg1 intron1 C/T | ACGTTGGATGATGTGTGGATTCACAGCTCG [SEQ. ID. NO. 302] | ACGTTGGATGGGGTTGGCAACTCTAAAAGG [SEQ. ID. NO. 303] |
| ACT | REV1 Phe257Ser C/T | ACGTTGGATGCTCTGAAATCAGTGCTGCTC [SEQ. ID. NO. 304] | ACGTTGGATGATGGTCAACAGTGTTGCCAG [SEQ. ID. NO. 305] |
| ACT | Apex1 Asp148Glu G/T | ACGTTGGATGCACCTCTTGATTGCTTTCCC [SEQ. ID. NO. 306] | ACGTTGGATGACCCGGCCTTCCTGATCATG [SEQ. ID. NO. 307] |
| ACG | IL-10-1082 A/G | ACGTTGGATGATTCCATGGAGGCTGGATAG [SEQ. ID. NO. 308] | ACGTTGGATGGACAACACTACTAAGGCTTC [SEQ. ID. NO. 309] |

Sequenom conditions for the polymorphisms genotyping-6

| SNP_ID | AMP_LEN | UP_CONF | MP_CONF | Tm(NN) | PcGC | PWARN | UEP_DIR | UEP_MASS |
|---|---|---|---|---|---|---|---|---|
| CTGF-447G/C | 119 | 98.2 | 65 | 52 | 52.9 | | R | 5090.3 |
| NBS1 Gln185Glu G/C | 118 | 97 | 65 | 51 | 52.9 | | R | 5192.4 |
| MBL2 161 G/A | 99 | 96.8 | 65 | 50.3 | 52.9 | | F | 5299.5 |
| IGF2R Leu252Val C/G | 114 | 98.5 | 67.8 | 68.6 | 82.4 | | F | 5206.4 |
| MUC5AC -221 C/T | 119 | 81.8 | 67.8 | 56.9 | 64.7 | g | R | 5273.4 |
| Arg1 intron1 C/T | 102 | 99.6 | 67.8 | 53.3 | 52.6 | | R | 5932.9 |
| REV1 Phe257Ser C/T | 105 | 99.6 | 67.8 | 57.5 | 55 | | R | 6003.9 |
| Apex1 Asp148Glu G/T | 114 | 92.9 | 67.8 | 46.8 | 35 | | F | 6113 |
| IL-10 -1082 A/G | 107 | 98 | 68.8 | 51.2 | 58.8 | | R | 4977.2 |

Sequenom conditions for the polymorphisms genotyping -7

| SNP_ID | UEP_SEQ | EXT1_CALL | EXT1_MASS | EXT1_SEQ |
|---|---|---|---|---|
| CTGF-447 G/C | AAAAGGTTTCTCCCCCC [SEQ. ID. NO. 310] | G | 5363.5 | AAAAGGTTTCTCCCCCCC [SEQ. ID. NO. 311] |
| NBS1 Gln185Glu G/C | AGGCTGCTTCTTGGACT [SEQ. ID. NO. 312] | G | 5465.6 | AGGCTGCTTCTTGGACTC [SEQ. ID. NO. 313] |
| MBL2 161 G/A | CAAAGATGGGCGTGATG [SEQ. ID. NO. 314] | A | 5596.7 | CAAAGATGGGCGTGATGA [SEQ. ID. NO. 315] |
| IGF2R Leu252Val C/G | GCCAGCCCCGGGACGGA [SEQ. ID. NO. 316] | C | 5479.6 | GCCAGCCCCGGGACGGAC [SEQ. ID. NO. 317] |
| MUC5AC-221 C/T | ATGGGTGTGTCTGCCGG [SEQ. ID. NO. 318] | T | 5570.6 | ATGGGTGTGTCTGCCGGA [SEQ. ID. NO. 319] |
| Arg1 intron1 C/T | GGCTGTAAGGAAATCTGGG [SEQ. ID. NO. 320] | T | 6230.1 | GGCTGTAAGGAAATCTGGGA [SEQ. ID. NO. 321] |
| REV1 Phe257Ser C/T | CCTTATCCTCCTCCTGGGAA [SEQ. ID. NO. 322] | T | 6301.1 | CCTTATCCTCCTCCTGGGAAA [SEQ. ID. NO. 323] |
| Apex1 Asp148Glu G/T | TGTTTCATTTCTATAGGCGA [SEQ. ID. NO. 324] | T | 6401.2 | TGTTTCATTTCTATAGGCGAT [SEQ. ID. NO. 325] |

Sequenom conditions for the polymorphisms genotyping -7

| SNP_ID | UEP_SEQ | EXT1_CALL | EXT1_MASS | EXT1_SEQ |
|---|---|---|---|---|
| IL-10-1082 A/G | CCTATCCCTACTTCCCC [SEQ. ID. NO. 326] | G | 5250.4 | CCTATCCCTACTTCCCCC [SEQ. ID. NO. 327] |

Sequenom conditions for the polymorphisms genotyping -8

| SNP_ID | EXT2_CALL | EXT2_MASS | EXT2_SEQ | 1$^{st}$PAUSE |
|---|---|---|---|---|
| CTGF-447 G/C | C | 5716.7 | AAAAGGTTTCTCCCCCCGA [SEQ. ID. NO. 328] | 5419.5 |
| NBS1 Gln185Glu G/C | C | 5818.8 | AGGCTGCTTCTTGGACTGA [SEQ. ID. NO. 329] | 5521.6 |
| MBL2 161 G/A | G | 5901.9 | CAAAGATGGGCGTGATGGC [SEQ. ID. NO. 330] | 5628.7 |
| IGF2R Leu252Val C/G | G | 5823.8 | GCCAGCCCCGGGACGGAGT [SEQ. ID. NO. 331] | 5535.6 |
| MUC5AC-221 C/T | C | 5890.8 | ATGGGTGTGTCTGCCGGGT [SEQ. ID. NO. 332] | 5602.6 |
| Arg1 intron1 C/T | C | 6879.5 | GGCTGTAAGGAAATCTGGGGGT [SEQ. ID. NO. 333] | 6262.1 |
| REV1 Phe257Ser C/T | C | 6630.3 | CCTTATCCTCCTCCTGGGAAGA [SEQ. ID. NO. 334] | 6333.1 |
| Apex1 Asp148Glu G/T | G | 7068.6 | TGTTTCATTTCTATAGGCGAGGA [SEQ. ID. NO. 335] | 6442.2 |
| IL-10-1082 A/G | A | 5858.8 | CCTATCCCTACTTCCCCTTC [SEQ. ID. NO. 336] | 5281.4 |

Results

Frequencies of individual polymorphisms are as follows:

TABLE 11

Polymorphism allele and genotype frequencies in the Lung cancer patients, resistant smokers and controls.

Nitric oxide synthase 3 Asp 298 Glu (T/G)

| | Allele* | | Genotype | | |
|---|---|---|---|---|---|
| Frequency | T | G | TT | TG | GG |
| Controls n = 183 (%) | 108 (30%) | 258 (70%) | 13 (7%) | 82 (45%) | 88 (48%) |
| Lung Cancer n = 107 (%) | 71 (33%) | 143 (67%) | 9 (8%) | 53 (50%) | 45 (42%) |
| Resistant n = 198 (%) | 135 (34%) | 261 (66%) | 28$^{1,2}$ (14%) | 79 (40%) | 91 (46%) |

Nitric oxide synthase 3 -786 T/C

| | Allele* | | Genotype | | |
|---|---|---|---|---|---|
| Frequency | C | T | CC | CT | TT |
| Controls n = 183 (%) | | | | | |
| Lung Cancer n = 107 (%) | 82 (38%) | 132 (62%) | 16 (15%) | 50 (47%) | 41$^3$ (38%) |
| Resistant n = 198 (%) | 166 (42%) | 228 (58%) | 31 (16%) | 104 (53%) | 62 (31%) |

TABLE 11-continued

Polymorphism allele and genotype frequencies in the Lung cancer patients, resistant smokers and controls.

Super oxide dismutase 3 Arg 312 Gln C/G

| Frequency | Allele* | | Genotype | | |
|---|---|---|---|---|---|
| | C | G | CC | CG | GG |
| Controls n = 190 (%) | 371 (98%) | 9 (2%) | 183 (96%) | 5 (3%) | 2 (1%) |
| Lung Cancer n = 104 (%) | 208 (100%) | 0 (0%) | 104 (100%) | 0 (0%) | 0 (0%) |
| Resistant n = 182 (%) | 390 (98%) | 10 (3%) | 191 (95%) | $8^4$ (4%) | $1^4$ (1%) |

XRCC1 Arg 399 Gln A/G

| Frequency | Allele* | | Genotype | | |
|---|---|---|---|---|---|
| | A | G | AA | AG | GG |
| Controls n = 190 (%) | | | | | |
| Lung Cancer n = 103 (%) | 68 (33%) | 138 (67%) | 4 (4%) | 60 (58%) | 39 (38%) |
| Resistant n = 193 (%) | 132 (34%) | 254 (66%) | $18^5$ (9%) | 96 (50%) | 79 (41%) |

Interleukin 8 −251 A/T

| Frequency | Allele* | | Genotype | | |
|---|---|---|---|---|---|
| | A | T | AA | AT | TT |
| Controls n = 188 (%) | 175 (47%) | 201 (53%) | 39 (21%) | 97 (52%) | 52 (28%) |
| Lung Cancer n = 90 | 68 (38%) | 112 (62%) | 6 (7%) | 56 (52%) | 28 (31%) |
| Resistant n = 199 (%) | $192^7$ (48%) | 206 (52%) | $45^6$ (23%) | 102 (51%) | 52 (26%) |

Anti-chymotrypsin Ala −15 Thr

| Frequency | Allele* | | Genotype | | |
|---|---|---|---|---|---|
| | A | G | AA | AG | GG |
| Lung Cancer n = 108 | 99 (46%) | $117^9$ (54%) | 24 (22%) | 51 (47%) | $33^8$ (31%) |
| Resistant n = 196 (%) | 207 (53%) | 185 (47%) | 52 (27%) | 103 (53%) | 41 (21%) |

Cyclin D1 A 870 G

| Frequency | Allele* | | Genotype | | |
|---|---|---|---|---|---|
| | A | G | AA | AG | GG |
| Lung Cancer n = 107 | 109 (51%) | 105 (49%) | $25^{11}$ (23%) | 59 (55%) | 23 (21%) |
| Resistant n = 199 (%) | 188 (47%) | 210 (53%) | 45 (23%) | 98 (49%) | $56^{10}$ (28%) |

Interleukin 1B −511 A/G

| Frequency | Allele* | | Genotype | | |
|---|---|---|---|---|---|
| | A | G | AA | AG | GG |
| Lung Cancer n = 107 | 64 (30%) | 150 (70%) | 12 (11%) | 40 (37%) | $55^{12}$ (51%) |
| Resistant n = 198 (%) | 143 (36%) | 253 (64%) | 23 (12%) | 97 (49%) | 78 (39%) |

FAS (Apo-1/CD 95) A −670 G

| Frequency | Allele* | | Genotype | | |
|---|---|---|---|---|---|
| | A | G | AA | AG | GG |
| Lung Cancer n = 106 | $121^{14}$ (57%) | 91 (43%) | $32^{13}$ (30%) | 57 (54%) | 17 (16%) |
| Resistant n = 198 (%) | 202 (51%) | 194 (49%) | 45 (23%) | 112 (57%) | 41 (21%) |

XPD 751 T/G

| Frequency | Allele* | | Genotype | | |
|---|---|---|---|---|---|
| | G | T | GG | TG | TT |
| Lung Cancer n = 108 | 72 (33%) | 144 (66%) | 11 (10%) | 50 (46%) | 47 (44%) |
| Resistant n = 197 (%) | 147 (37%) | 247 (63%) | $31^{15}$ (16%) | 85 (43%) | 81 (41%) |

TABLE 11-continued

Polymorphism allele and genotype frequencies in the Lung cancer patients, resistant smokers and controls.

Cytochrome P450 1A1 Ile 462 Val G/A

| Frequency | Allele* | | Genotype | | |
|---|---|---|---|---|---|
| | G | A | GG | AG | AA |
| Lung Cancer n = 109 | 5 (2%) | 213 (98%) | 0 (0%) | 5 (5%) | 104[16] (95%) |
| Resistant n = 199 (%) | 20 (5%) | 378 (95%) | 13[16] (1%) | 18[16] (9%) | 180[2] (90%) |

MMP12 Asn 357 Ser

| Frequency | Allele* | | Genotype | | |
|---|---|---|---|---|---|
| | G | A | GG | AG | AA |
| Lung Cancer n = 109 | 8 (4%) | 210 (96%) | 1 (1%) | 6 (5%) | 102 (94%) |
| Resistant n = 199 (%) | 21 (5%) | 377 (95%) | 0[17] (0%) | 21[17] (11%) | 178 (89%) |

8-oxoguanine DNA glycosylase Ser 326 Cys C/G

| Frequency | Allele* | | Genotype | | |
|---|---|---|---|---|---|
| | G | C | GG | CG | CC |
| Lung Cancer n = 109 | 40 (18%) | 178 (82%) | 2 (2%) | 36 (33%) | 71 (65%) |
| Resistant n = 199 (%) | 100 (25%) | 298 (75%) | 14[18] (7%) | 72 (36%) | 113 (57%) |

N-Acetyltransferase 2 Arg 197 Gln G/A

| Frequency | Allele* | | Genotype | | |
|---|---|---|---|---|---|
| | A | G | AA | AG | GG |
| Lung Cancer n = 106 | 55 (26%) | 157 (74%) | 9 (8%) | 37 (35%) | 60[19] (57%) |
| Resistant n = 195 (%) | 122 (31%) | 268 (69%) | 17 (9%) | 88 (45%) | 90 (46%) |

Cytochrome P450 2E1 1019 G/C Pst1

| Frequency | Allele* | | Genotype | | |
|---|---|---|---|---|---|
| | C | G | CC | CG | GG |
| Lung Cancer n = 109 | 10 (5%) | 208 (95%) | 0 (0%) | 10[20] (9%) | 99 (91%) |
| Resistant n = 197 (%) | 11 (3%) | 383 (97%) | 0 (0%) | 11 (6%) | 186 (94%) |

Cytochrome P450 2E1 C/T Rsa I

| Frequency | Allele* | | Genotype | | |
|---|---|---|---|---|---|
| | T | C | TT | TC | CC |
| Lung Cancer n = 108 | 11 (5%) | 205 (95%) | 0 (0%) | 11[21] (10%) | 97 (90%) |
| Resistant n = 198 (%) | 11 (3%) | 385 (97%) | 0 (0%) | 11 (6%) | 187 (94%) |

Interleukin 18 105 A/C

| Frequency | Allele* | | Genotype | | |
|---|---|---|---|---|---|
| | C | A | CC | AC | AA |
| Lung Cancer n = 107 | 50 (23%) | 164 (77%) | 8 (8%) | 34 (33%) | 65[22] (61%) |
| Resistant n = 200 (%) | 116 (29%) | 284 (71%) | 17[22] (9%) | 82[22] (41%) | 101 (50%) |

Interleukin 18 −133 C/G

| Frequency | Allele* | | Genotype | | |
|---|---|---|---|---|---|
| | G | C | GG | CG | CC |
| Lung Cancer n = 109 | 52 (24%) | 166 (76%) | 8 (7%) | 36 (33%) | 65[23] (60%) |
| Resistant n = 198 (%) | 117 (30%) | 279 (70%) | 17[23] (9%) | 83[23] (42%) | 98 (49%) |

TABLE 11-continued

Polymorphism allele and genotype frequencies in the Lung cancer patients, resistant smokers and controls.

Glutathione S-Transferase M null

| | Allele* | |
|---|---|---|
| Frequency | Null | Wild |
| Controls n = 178 | 75 (42%) | 103 (58%) |
| Lung Cancer n = 107 | 67[24] (58%) | 48 (42%) |
| Resistant n = 182 | 100 (55%) | 82 (45%) |

Interferon-gamma 874 A/T

| | Allele* | | Genotype | | |
|---|---|---|---|---|---|
| Frequency | A | T | AA | AT | TT |
| Controls n = 186 (%) | 183 (49%) | 189 (51%) | 37 (20%) | 109 (58%) | 40 (22%) |
| Lung cancer n = 106 (%) | 116 (55%) | 96 (45%) | 34[25,26] (32%) | 48 (45%) | 24 (23%) |
| Resistant n = 196 (%) | 209 (53%) | 183 (47%) | 50 (26%) | 109 (56%) | 37 (19%) |

Cyclooxygenase −765 C/G

| | Allele* | | Genotype | | |
|---|---|---|---|---|---|
| Frequency | C | G | CC | CG | GG |
| Controls n = 95 (%) | 27 (14%) | 161 (86%) | 3 (3%) | 21 (22%) | 70 (75%) |
| Lung Cancer n = 109 (%) | 34 (16%) | 184 (84%)[30] | 5 (5%)[27] | 24 (22%)[27] | 80 (73%)[29] |
| Resistant n = 158 (%) | 75 (24%)[28] | 241 (76%) | 11 (7%) | 53 (34%) | 94 (59%) |

Matrix metalloproteinase 1 −1607 1G/2G

| | Allele* | | Genotype | | |
|---|---|---|---|---|---|
| Frequency | 1G | 2G | 1G1G | 1G2G | 2G2G |
| Controls n = 174 (%) | 214 (61%) | 134 (39%) | 68 (39%) | 78 (45%) | 28 (16%) |
| Lung Cancer n = 67 (%) | [10] 58 (43%) | 76 (57%)[32] | 13 (19%) | 32 (48%) | 22 (33%)[31] |
| Resistant n = 171 (%) | 167 (49%) | 175 (51%) | 41 (24%) | 85 (50%) | 45 (26%) |

*number of chromosomes (2n)

[1] Genotype. TT vs TG/GG for resistant vs lung cancer, Odds ratio (OR) = 1.8, 95% confidence limits 0.8-4.3, $\chi^2$ (Yates uncorrected) = 2.14, p = 0.14, TT genotype = protective

[2] Genotype. TT vs TG/GG for resistant vs controls, Odds ratio (OR) = 2.2, 95% confidence limits 1.0-4.6, $\chi^2$ (Yates corrected) = 4.2, p = 0.04, TT genotype = protective

[3] Genotype. TT vs CC/CT for Lung cancer vs resistant, Odds ratio (OR) = 1.4, 95% confidence limits 0.8-2.3, $\chi^2$ (Yates uncorrected) = 1.45, p = 0.23, TT genotype = susceptible

[4] Genotype CG/GG vs CC for Lung cancer vs resistant, Yates uncorrected = 3.38, P = 0.07 and Fisher's Two tailed test, P = 0.03. CG/GG = protective

[5] Genotype. AA vs AG/GG for resistant vs lung cancer, Odds ratio (OR) = 2.6, 95% confidence limits 0.8-9.2, $\chi^2$ (Yates uncorrected) = 2.89, p = 0.09. AA genotype = protective

[6] Genotype. AA vs AT/TT for resistant vs lung cancer, Odds ratio (OR) = 4.1, 95% confidence limits = 1.6 = 11.2, $\chi^2$ (Yates corrected) = 9.8, p = 0.002, AA = protective

[7] Allele. A vs T for resistant smokers vs lung cancer, Odds ratio (OR) = 1.5, 95% confidence limits 1.0-2.2, $\chi^2$ (Yates corrected) = 5.07, p = 0.02, A = protective

[8] Genotype. GG vs AA/AG for Lung cancer vs resistant, Odds ratio (OR) = 1.7, 95% confidence limits = 0.9-2.9, $\chi^2$ (Yates uncorrected) = 3.51, p = 0.06, GG = susceptible

[9] Allele. G vs A for lung cancer vs resistant smokers, Odds ratio (OR) = 1.3, 95% confidence limits 0.9-1.9, $\chi^2$ (Yates uncorrected) = 2.71, p = 0.10, G = susceptible

[10] Genotype. GG vs AG/AA for Resistant vs lung cancer, Odds ratio (OR) = 1.4, 95% confidence limits = 0.8-2.6, $\chi^2$ (Yates uncorrected) = 1.6, p = 0.20, GG = protective

[11] Genotype. AG/AA vs GG for Lung cancer vs resistant, Odds ratio (OR) = 1.4, 95% confidence limits = 0.8-2.6, $\chi^2$ (Yates uncorrected) = 1.6, p = 0.20, AA = susceptible

[12] Genotype. GG vs AA/AG for Lung cancer vs resistant, Odds ratio (OR) = 1.6, 95% confidence limits = 1-2.7, $\chi^2$ (Yates uncorrected) = 4.07, p = 0.04, GG = susceptible

[13] Genotype. AA vs AG/GG for Lung cancer vs resistant, Odds ratio (OR) = 1.5, 95% confidence limits = 0.8-2.6, $\chi^2$ (Yates uncorrected) = 2.03, p = 0.15, AA = susceptible

[14] Allele. A vs G for Lung cancer vs resistant, Odds ratio (OR) = 1.3, 95% confidence limits 0.9-1.8, $\chi^2$ (Yates uncorrected) = 2.04, p = 0.15, A = susceptible

[15] Genotype. GG vs TG/TT for Resistant vs lung cancer, Odds ratio (OR) = 1.7, 95% confidence limits = 0.8-3.7, $\chi^2$ (Yates uncorrected) = 1.81, p = 0.18, GG = protective

[16] Genotype. AG/GG vs AA for Resistant vs lung cancer, Odds ratio (OR) = 2.2, 95% confidence limits = 0.7-6.9, $\chi^2$ (Yates uncorrected) = 2.41, p = 0.12, GG/AG = protective, AA = susceptible

[17] Genotype. GG/AG vs AA for Resistant vs COPD, Odds ratio (OR) = 1.7, 95% confidence limits = 0.7-4.6, $\chi^2$ (Yates uncorrected) = 1.45, p = 0.23, GG/AG = protective

[18] Genotype. GG vs CG/CC for Resistant vs lung cancer, Odds ratio (OR) = 4.0, 95% confidence limits = 0.9-26.3, $\chi^2$ (Yates uncorrected) = 3.87, p = 0.05, GG = protective

[19] Genotype. GG vs AG/AA for Lung cancer vs resistant, Odds ratio (OR) = 1.5, 95% confidence limits = 0.9-2.5, $\chi^2$ (Yates uncorrected) = 3.0, p = 0.08, GG = susceptible

[20] Genotype. CG vs GG for Lung cancer and resistant, Odds ratio (OR) = 1.7, 95% confidence limits = 0.7-4.5, $\chi^2$ (Yates uncorrected) = 1.42, p = 0.23, CG = susceptible

[21] Genotype. TC vs CC for Lung cancer and resistant, Odds ratio (OR) = 1.9, 95% confidence limits = 0.8-5.0, $\chi^2$ (Yates uncorrected) = 2.24, p = 0.13, TC = susceptible

[22] Genotype. AA vs AC/CC for Lung cancer and resistant, Odds ratio (OR) = 1.6, 95% confidence limits = 1.0-2.6, $\chi^2$ (Yates uncorrected) = 3.51, p = 0.06, AA = susceptible, AC/CC protective TABLE 11-continued Polymorphism allele and genotype frequencies in the Lung cancer patients, resistant smokers and controls.

[23]Genotype. CC vs CG/GG for Lung cancer and resistant, Odds ratio (OR) = 1.5, 95% confidence limits = 0.9-2.5, $\chi^2$ (Yates uncorrected) = 2.90, p = 0.09, CC = susceptible, CG/GG protective
[24]Genotype. Null vs wild for Lung cancer and controls, Odds ratio (OR) = 1.92, 95% confidence limits = 1.2-3.2, $\chi^2$ (Yates corrected) = 6.64, p = 0.01, Null = susceptible
[25]Genotype. AA vs AT/TT for lung cancer vs resistant, Odds ratio (OR) = 1.4, 95% confidence limits 0.8-2.4, $\chi^2$ (Yates uncorrected) = 1.48, p = 0.22, AA genotype = susceptible
[26]Genotype. AA vs AT/TT for lung cancer vs controls, Odds ratio (OR) = 1.9, 95% confidence limits 1.1-3.4, $\chi^2$ (Yates corrected) = 5.45, p = 0.02, AA genotype = susceptible to lung cancer
[27]Genotype. CC/CG vs GG for Lung cancer vs resistant, Odds ratio (OR) = 0.53, 95% confidence limits = 0.3-0.9, $\chi^2$ (Yates corrected) = 4.9, P = 0.03 CC/CG = protective
[28]Allele. C vs G for Lung cancer vs resistant, Odds ratio (OR) = 0.59, 95% confidence limits 0.4-0.9, $\chi^2$ (Yates corrected) = 4.8, p = 0.03, C = protective
[29]Genotype. GG vs CG/CC for Lung cancer vs resistant, Odds ratio (OR) = 1.88, 95% confidence limits = 1.1-3.3, $\chi^2$ (Yates corrected) = 4.9, P = 0.03 GG = susceptible (when compared against resistant smokers but not controls)
[30]Allele. G vs C for Lung cancer vs resistant, Odds ratio (OR) = 1.7, 95% confidence limits 1.1-2.7, $\chi^2$ (Yates corrected) = 4.8, p = 0.03, G = susceptible (when compared against resistant smokers but not controls)
[31]Genotype. 2G2G vs 1G1G/1G2G for Lung cancer vs controls, Odds ratio (OR) = 2.55, 95% confidence limits 1.3-5.1, $\chi^2$ (Yates corrected) = 7.3, p = 0.007 2G2G genotype = susceptible
[32]Allele. 2G vs 1G for Lung cancer vs controls, Odds ratio (OR) = 2.1, 95% confidence limits 1.4-3.2, $\chi^2$ (Yates corrected) = 12.3, p = 0.0004, 2G = susceptible Connective tissue growth factor (CTGF) −447 G/C polymorphism allele and genotype frequencies in the lung cancer and resistant smokers.

| Frequency | 37. Allele* | | 38. Genotype | | |
|---|---|---|---|---|---|
| | G | C | GG | GC | CC |
| Lung cancer n = 109 | 201 | 17 | 92 | 17 | 0 |
| (%) | (92%) | (8%) | (84%) | (16%) | (0%) |
| Resistant n = 200 | 379 | 21 | 179 | 21 | 0 |
| (%) | (95%) | (5%) | (90%) | (10%) | (0%) |

*number of chromosomes (2n)

1. Genotype. GC/CC vs GG for lung cancer vs resistant, Odds ratio (OR) = 1.6, 95% confidence limits 0.8-3.3, $\chi^2$ (Yates uncorrected) = 1.70, p = 0.19, GC/CC genotype = susceptibility (trend)

Nibrin (NBS1) Gln185Glu G/C polymorphism allele and genotype frequencies in the lung cancer and resistant smokers.

| Frequency | 43. Allele* | | 44. Genotype | | |
|---|---|---|---|---|---|
| | G | C | GG | GC | CC |
| Lung cancer n = 109 | 150 | 68 | 54 | 42 | 13 |
| (%) | (69%) | (31%) | (50%) | (39%) | (12%) |
| Resistant n = 199 | 295 | 103 | 107 | 81 | 11 |
| (%) | (74%) | (26%) | (54%) | (41%) | (6%) |

*number of chromosomes (2n)

1. Genotype. CC vs CG/GG for lung cancer vs resistant, Odds ratio (OR) = 2.3, 95% confidence limits 0.9-5.8, $\chi^2$ (Yates uncorrected) = 4.01, p = 0.05, CC genotype = susceptibility Mucin 5AC (Muc5AC) −221 C/T polymorphism allele and genotype frequencies in the lung cancer and resistant smokers.

| Frequency | 39. Allele* | | 40. Genotype | | |
|---|---|---|---|---|---|
| | C | T | CC | CT | TT |
| Lung cancer n = 109 | 177 | 41 | 73 | 31 | 5 |
| (%) | (81%) | (19%) | (67%) | (28%) | (5%) |
| Resistant n = 195 | 296 | 94 | 119 | 58 | 18 |
| (%) | (76%) | (24%) | (61%) | (30%) | (9%) |

*number of chromosomes (2n)

1. Genotype. TT vs CC/CT for lung cancer vs resistant, Odds ratio (OR) = 0.47, 95% confidence limits 0.2-1.4, $\chi^2$ (Yates uncorrected) = 2.16, p = 0.14, TT genotype = protective (trend)

Arginase 1 (Arg1) intron 1 C/T polymorphism allele and genotype frequencies in the lung cancer and resistant smokers.

| Frequency | 45. Allele* | | 46. Genotype | | |
|---|---|---|---|---|---|
| | C | T | CC | CT | TT |
| Lung cancer n = 105 | 137 | 73 | 45 | 47 | 13 |
| (%) | (65%) | (35%) | (43%) | (45%) | (12%) |
| Resistant n = 180 | 203 | 157 | 65 | 73 | 42 |
| (%) | (56%) | (44%) | (36%) | (41%) | (23%) |

*number of chromosomes (2n)

1. Genotype. TT vs CC/CT for lung cancer vs resistant, Odds ratio (OR) = 0.46, 95% confidence limits 0.2-0.95, $\chi^2$ (Yates uncorrected) = 5.11, p = 0.02, TT genotype = protective
2. Allele. T vs C for lung cancer vs resistant, Odds ratio (OR) = 0.69, 95% confidence limits 0.5-1.0, $\chi^2$ (Yates corrected) = 3.96, p = 0.05, T allele = protective Mannose binding lectin (MBL2) 161 G/A polymorphism allele and genotype frequencies in the lung cancer and resistant smokers.

| Frequency | 41. Allele* | | 42. Genotype | | |
|---|---|---|---|---|---|
| | G | A | GG | AG | AA |
| Lung cancer n = 105 | 173 | 37 | 71 | 31 | 3 |
| (%) | (82%) | (18%) | (67%) | (30%) | (3%) |
| Resistant n = 197 | 338 | 56 | 147 | 44 | 6 |
| (%) | (86%) | (14%) | (75%) | (22%) | (3%) |

*number of chromosomes (2n)

1. Genotype. AG/AA vs GG for lung cancer vs resistant, Odds ratio (OR) = 1.4, 95% confidence limits 0.8-2.4, $\chi^2$ (Yates uncorrected) = 1.67, p = 0.20, AG/AA genotype = susceptibility (trend)

REV1 Phe257Ser C/T polymorphism allele and genotype frequencies in the lung cancer and resistant smokers.

| Frequency | 47. Allele* | | 48. Genotype | | |
|---|---|---|---|---|---|
| | C | T | CC | CT | TT |
| Lung cancer n = 109 | 129 | 89 | 39 | 51 | 19 |
| (%) | (59%) | (41%) | (36%) | (47%) | (17%) |
| Resistant n = 192 | 242 | 142 | 83 | 76 | 33 |
| (%) | (63%) | (37%) | (43%) | (40%) | (17%) |

*number of chromosomes (2n)

1. Genotype. CC vs CT/TT for lung cancer vs resistant, Odds ratio (OR) = 0.73, 95% confidence limits 0.4-1.2, $\chi^2$ (Yates uncorrected) = 1.6, p = 0.20, CC genotype = protective (trend)

Insulin-like growth factor II receptor (IGF2R) Leu252Val C/G polymorphism allele and genotype frequencies in the lung cancer and resistant smokers.

|  | 49. Allele* | | 50. Genotype | | |
|---|---|---|---|---|---|
| Frequency | C | G | CC | CG | GG |
| Lung cancer n = 109 (%) | 190 (87%) | 28 (13%) | 82 (75%) | 26 (24%) | 1 (1%) |
| Resistant n = 198 (%) | 342 (86%) | 54 (14%) | 150 (76%) | 42 (21%) | 6 (3%) |

*number of chromosomes (2n)
1. Genotype. GG vs CC/CG for lung cancer vs resistant, Odds ratio (OR) = 0.30, 95% confidence limits 0.01-2.5, $\chi^2$ (Yates uncorrected) = 1.41, p = 0.22 (1-tailed t-test), GG genotype = protective (trend)

Apex nuclease (APE1) Asp148Glu T/G polymorphism allele and genotype frequencies in the lung cancer and resistant smokers.

|  | 51. Allele* | | 52. Genotype | | |
|---|---|---|---|---|---|
| Frequency | T | G | TT | TG | GG |
| Lung cancer n = 109 (%) | 124 (57%) | 94 (43%) | 39 (36%) | 46 (42%) | 24 (22%) |
| Resistant n = 192 (%) | 229 (60%) | 155 (40%) | 69 (36%) | 91 (47%) | 32 (17%) |

*number of chromosomes (2n)
1. Genotype. GG vs TT/TG for lung cancer vs resistant, Odds ratio (OR) = 1.4, 95% confidence limits 0.8-2.7, $\chi^2$ (Yates uncorrected) = 1.3, p = 0.25, GG genotype = susceptibility (trend)

Interleukin 10 (IL-10) −1082 A/G polymorphism allele and genotype frequencies in the lung cancer and resistant smokers.

|  | 53. Allele* | | 54. Genotype | | |
|---|---|---|---|---|---|
| Frequency | G | C | GG | GC | CC |
| Lung cancer n = 98 (%) | 91 (46%) | 105 (54%) | 16 (16%) | 59 (60%) | 23 (24%) |
| Resistant n = 196 (%) | 174 (44%) | 218 (56%) | 40 (20%) | 94 (48%) | 62 (32%) |

*number of chromosomes (2n)
1. Genotype. GG vs GC/CC for lung cancer vs resistant, Odds ratio (OR) = 0.66, 95% confidence limits 0.4-1.2, $\chi^2$ (Yates uncorrected) = 2.12, p = 0.15, GG genotype = protective (trend)

Table 12 below provides a summary of the protective and susceptibility polymorphisms determined for lung cancer.

TABLE 12

Summary of protective and susceptibility polymorphisms in Lung Cancer patients relative to resistant smokers (with normal lung function)

| Gene | Polymorphism | Role |
|---|---|---|
| Nitric Oxide synthase 3 (NOS3) | NOS3 Asp 298 Glu | TT protective |
| Nitric Oxide synthase 3 (NOS3) | NOS3 −786 T/C | TT susceptible |
| Superoxide dismutase 3 (SOD3) | SOD3 Arg 312 Gln | CG/GG protective |
| XRCC1 | XRCC1 Arg 399 Gln G/A | AA protective |
| Interleukin-8 (IL-8) | IL-8 −251 A/T | AA protective |
| Anti-chymotrypsin (ACT) | ACT Ala 15 Thr | GG susceptible |
| Cyclin D (CCND1) | CCND1 A870G | GG protective AA susceptible |
| Interleukin 1B (IL-1B) | IL-1B −511 A/G | GG susceptible |
| FAS (Apo-1/CD95) | FAS A-670G | AA susceptible |
| XPD | XPD −751 G/T | GG protective |
| CYP 1A1 | CYP 1A1 Ile 462 Val A/G | GG/AG protective AA susceptible |
| Matrix metalloproteinase 12 (MMP12) | MMP12 Asn 357 Ser A/G | GG/AG protective |
| 8-Oxoguanine DNA glycolase (OGG1) | OGG1 Ser 326 Cys G/C | GG protective |
| N-acetyltransferase 2 (NAT2) | NAT2 Arg 197 Gln A/G | GG susceptible |
| CYP2E1 | CYP2E1 1019 G/C Pst I | CC/CG susceptible |
| CYP2E1 | CYP2E1 C/T Rsa I | TT/TC susceptible |
| Interleukin-18 (IL-18) | IL-18 105 A/C | AC/CC protective AA susceptible |
| Interleukin-18 (IL-18) | IL-18-133 G/C | CG/GG protective CC susceptible |
| Glutathione S-transferase M | GSTM null | Null susceptible |
| Interferon gamma (IFN?) | IFN? 874 A/T | AA susceptible |
| Cyclo-oxygenase 2 (COX2) | COX2 −765 G/C | CC/CG protective GG susceptible |
| Matrix metalloproteinase 1 (MMP1) | MMP −1607 1G/2G | 2G2G susceptible |
| Connective tissue growth factor (CTGF) | CTGF −447 G/C | GC/CC susceptible |
| Mucin 5AC (MUC5AC) | MUC5AC −221 C/T | TT protective |

TABLE 12-continued

Summary of protective and susceptibility polymorphisms in Lung Cancer
patients relative to resistant smokers (with normal lung function)

| Gene | Polymorphism | Role |
| --- | --- | --- |
| Mannose binding lectin 2 (MBL2) | MBL2 +161 G/A | AG/AA susceptible |
| Nibrin (NBS1) | NBS1 Gln185Glu G/C | CC susceptible |
| Arginase 1 (Arg1) | Arg1 intron 1 C/T | TT protective |
| REV1 | REV1 Phe257Ser C/T | CC protective |
| Insulin-like growth factor II receptor (IGF2R) | IGF2R Leu252Val C/G | GG protective |
| Apex nuclease (Apex or APE1)) | Apex Asp148Glu G/T | GG susceptible |
| Interleukin 10 (IL-10) | IL-10 −1082 A/G | GG protective |

The combined frequencies of the presence or absence of the selected protective genotypes CYP1A1GG/AG, OGG1 GG, CCND1 GG, NOS3 298 TT, IL-8 AA, and XRCC1 AA observed in the subjects with lung cancer and in resistant smokers is presented below in Table 13.

TABLE 13

Combined frequencies of the presence or absence of selected protective genotypes in subjects with lung cancer and in resistant smokers.

| | Number of protective polymorphisms | | | |
| --- | --- | --- | --- | --- |
| Cohorts | 0 | 1 | =2 | Total |
| Lung Cancer | 66 (61%) | 37 (34%) | 6 (6%) | 109 |
| Resistant smokers | 71 (36%) | 86 (43%) | 42 (21%) | 199 |
| % of smokers with Lung cancer | 66/137 (48%) | 37/123 (30%) | 6/42 (14%) | |

| Comparison | Odd's ratio | 95% CI | ?2 | P value |
| --- | --- | --- | --- | --- |
| 0 vs 1 vs 2+, Resist vs Lung cancer | — | — | 22.3 | <0.0001 |
| 2+ vs 0-1, Resist vs Lung cancer | 4.6 | 1.8-12.5 | 11.87 | 0.0005 |
| 0 vs 2+, Lung cancer vs Resist | 2.8 | 1.7-4.6 | 16.7 | <0.0001 |

The combined frequencies of the presence or absence of the selected susceptibility genotypes CYP2E1 1019 CC/CG, FAS AA, IL-1B GG, and ACT 15 GG, observed in the subjects with lung cancer and in resistant smokers is presented below in Table 14.

TABLE 14

Combined frequencies of the presence or absence of selected susceptibility genotypes in subjects with lung cancer and in resistant smokers.

| | Number of susceptibility polymorphisms | | | |
| --- | --- | --- | --- | --- |
| Cohorts | 0 | 1 | =2 | Total |
| Lung Cancer | 21 (19%) | 52 (48%) | 35 (33%) | 108 |
| Resistant smokers | 71 (36%) | 85 (43%) | 42 (21%) | 198 |
| % of smokers with COPD | 21/92 (23%) | 52/137 (38%) | 35/77 (45%) | |

| Comparison | Odd's ratio | 95% CI | ?2 | P value |
| --- | --- | --- | --- | --- |
| 0 vs 1 vs 2+, Lung cancer vs Resist | — | — | 10.2 | 0.006 |
| 2+ vs 0-1, Lung cancer vs Resist | 1.8 | 1.0-3.1 | 4.1 | 0.04 |
| 0+ vs 1-2+, Resist vs COPD | 2.3 | 1.3-4.2 | 8.2 | 0.004 |

The combined frequencies of the presence or absence of the selected protective genotypes CYP1A1 GG/AG, OGG1 GG, CCND1 GG, NOS3 298 TT, SOD3 CG/GG, XPD GG, MMP12 GG/AG, and XRCC1 AA observed in the subjects with lung cancer and in resistant smokers is presented below in Table 15.

TABLE 15

Combined frequencies of the presence or absence of selected protective genotypes in subjects with lung cancer and in resistant smokers.

| | Number of protective polymorphisms n = 8 | | | |
| --- | --- | --- | --- | --- |
| Cohorts | 0 | 1 | =2 | Total |
| Lung Cancer | 54 (50%) | 50 (46%) | 5 (4%) | 109 |
| Resistant smokers | 67 (34%) | 83 (42%) | 50 (25%) | 199 |
| % of smokers with Lung cancer | 54/121 (45%) | 50/133 (38%) | 5/55 (9%) | |

| Comparison | Odd's ratio | 95% CI | ?2 | P value |
| --- | --- | --- | --- | --- |
| 0 vs 1 vs 2+, Resist vs Lung cancer | — | — | 21.5 | <0.0001 |
| 2+ vs 0-1, Resist vs Lung cancer | 6.9 | 2.5-20.5 | 18.7 | <0.0001 |
| 0 vs 2+, Lung cancer vs Resist | 2.0 | 1.2-3.2 | 6.96 | 0.008 |

The combined frequencies of the presence or absence of the selected susceptibility genotypes CYP2E1 1019 CC/CG, FAS AA, IL-1B GG, ACT 15 GG, NAT2 GG, IL-18 105 AA, and IFN? AA, observed in the subjects with lung cancer and in resistant smokers is presented below in Table 16.

TABLE 16

Combined frequencies of the presence or absence of selected susceptibility genotypes in subjects with lung cancer and in resistant smokers.

| | Number of susceptibility polymorphisms n = 7 | | | |
| --- | --- | --- | --- | --- |
| Cohorts | 1 | 2 | =3 | Total |
| Lung Cancer | 16 (15%) | 35 (32%) | 58 (53%) | 109 |
| Resistant smokers | 65 (33%) | 66 (33%) | 69 (34%) | 200 |
| % of smokers with COPD | 16/81 (20%) | 35/101 (35%) | 58/127 (46%) | |

| Comparison | Odd's ratio | 95% CI | ?2 | P value |
| --- | --- | --- | --- | --- |
| 0 vs 1 vs 2+, Lung cancer vs Resist | — | — | 14.6 | 0.0007 |
| 3+ vs 1-2, Lung cancer vs Resist | 2.2 | 1.3-5.6 | 9.4 | 0.002 |
| 1 vs 2-3+, Resist vs COPD | 2.8 | 1.5-5.4 | 10.7 | 0.001 |

The combined frequencies of the presence or absence of the selected protective genotypes CYP1A1 GG/AG, OGG1 GG, CCND1 GG, NOS3 298 TT, IL-8 AA, XRCC1 AA, and Cox 2 −765 CC/CG, observed in the subjects with lung cancer and in resistant smokers is presented below in Table 17.

TABLE 17

Combined frequencies of the presence or absence of protective genotypes in the exposed smoking subjects (Lung cancer subjects and resistant smokers).

| Cohorts | Number of protective genotypes | | | Total |
|---|---|---|---|---|
| | 0 | 1 | =2 | |
| Lung Cancer | 45 (40%) | 50 (43%) | 19 (17%) | 114 |
| Resistant smokers | 47 (23%) | 79 (40%) | 74 (37%) | 200 |
| % of smokers with Lung cancer | 45/92 (49%) | 50/129 (39%) | 19/93 (20%) | |

| Comparison | Odd's ratio | 95% CI | ?2 | P value |
|---|---|---|---|---|
| 0 vs 1 vs 2+, Resist vs Lung cancer | — | — | 16.8 | 0.0002 |
| 2+ vs 0-1, Resist vs Lung cancer | 2.94 | 1.6-5.4 | 13.44 | 0.0002 |
| 0 vs 2+, Lung cancer vs Resist | 2.12 | 1.3-3.6 | 8.2 | 0.004 |

The combined frequencies of the presence or absence of the selected susceptibility genotypes CYP2E1 1019 CC/CG, FAS AA, IL-B1 GG, ACT 15 GG, and MMP1 2G2G, observed in the subjects with lung cancer and in resistant smokers is presented below in Table 18.

TABLE 18

Combined frequencies of the presence or absence of susceptibility genotypes in the exposed smoking subjects (Lung cancer subjects and resistant smokers).

| Cohorts | Number of susceptibility genotypes | | | Total |
|---|---|---|---|---|
| | 0-1 | 2-3 | 4-6 | |
| Lung Cancer | 13 (12%) | 66 (61%) | 30 (28%) | 109 |
| Resistant smokers | 54 (27%) | 113 (56%) | 33 (17%) | 200 |
| % of smokers with COPD | 13/67 (19%) | 66/179 (37%) | 30/63 (48%) | |

| Comparison | Odd's ratio | 95% CI | ?2 | P value |
|---|---|---|---|---|
| 0-1 vs 2-3 vs 4-6, Lung cancer vs Resist | — | — | 11.8 | 0.003 |
| 4-6 vs rest, Lung cancer vs Resist | 1.9 | 1.0-3.5 | 4.6 | 0.03 |
| 0-1 vs rest, Resist vs COPD | 2.7 | 1.4-5.6 | 8.6 | 0.003 |

Figure 4:
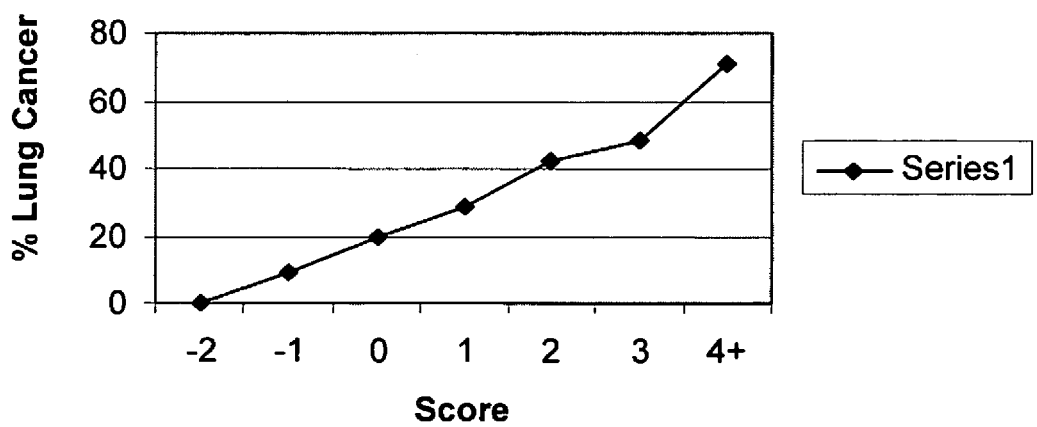
FIG. 4: depicts a graph showing net scores for protective and susceptibility polymorphisms in subjects with lung cancer.

Protective polymorphisms were assigned a score of −1 while susceptibility polymorphisms were assigned a score of +1. For each subject, a net score was then calculated according to the presence of susceptibility and protective genotypes. This produced a linear spread of values, as shown in Table 14. When assessed as a range between −2 to +4, a linear relationship as depicted in FIG. 4 was observed. This analysis indicates that for subjects with a net score of −2 or less, there was a minimal risk of having lung cancer. For subjects with a net score of −1, there was an approximately one in ten risk of having lung cancer. In contrast, for subjects with a net score of 4+ or greater, the risk was markedly increased to over 70% (see Table 19 and FIG. 4). It is noted that for FIG. 4, unlike the data presented in FIG. 3, the protective polymorphisms are assigned a negative value while the susceptibility polymorphisms are assigned a positive value. The precise value or sign given to each one is not critical, as long as it is consistent between the types of polymorphisms.

TABLE 19

Combined presence or absence of protective and susceptibility polymorphisms

| | Score combining protective (−1) and susceptibility (+1) polymorphisms | | | | | | |
|---|---|---|---|---|---|---|---|
| | −2 | −1 | 0 | 1 | 2 | 3 | 4+ |
| Lung cancer N = 109 (%) | 0 (0%) | 2 (2%) | 10 (9%) | 21 (19%) | 38 (35%) | 23 (21%) | 15 (14%) |
| Resistant smokers N = 200 (%) | 6 (3%) | 21 (11%) | 39 (20%) | 51 (26%) | 52 (26%) | 25 (13%) | 6 (3%) |
| % Lung cancer | 0% | 9% | 20% | 29% | 42% | 48% | 71% |

Figure 5:
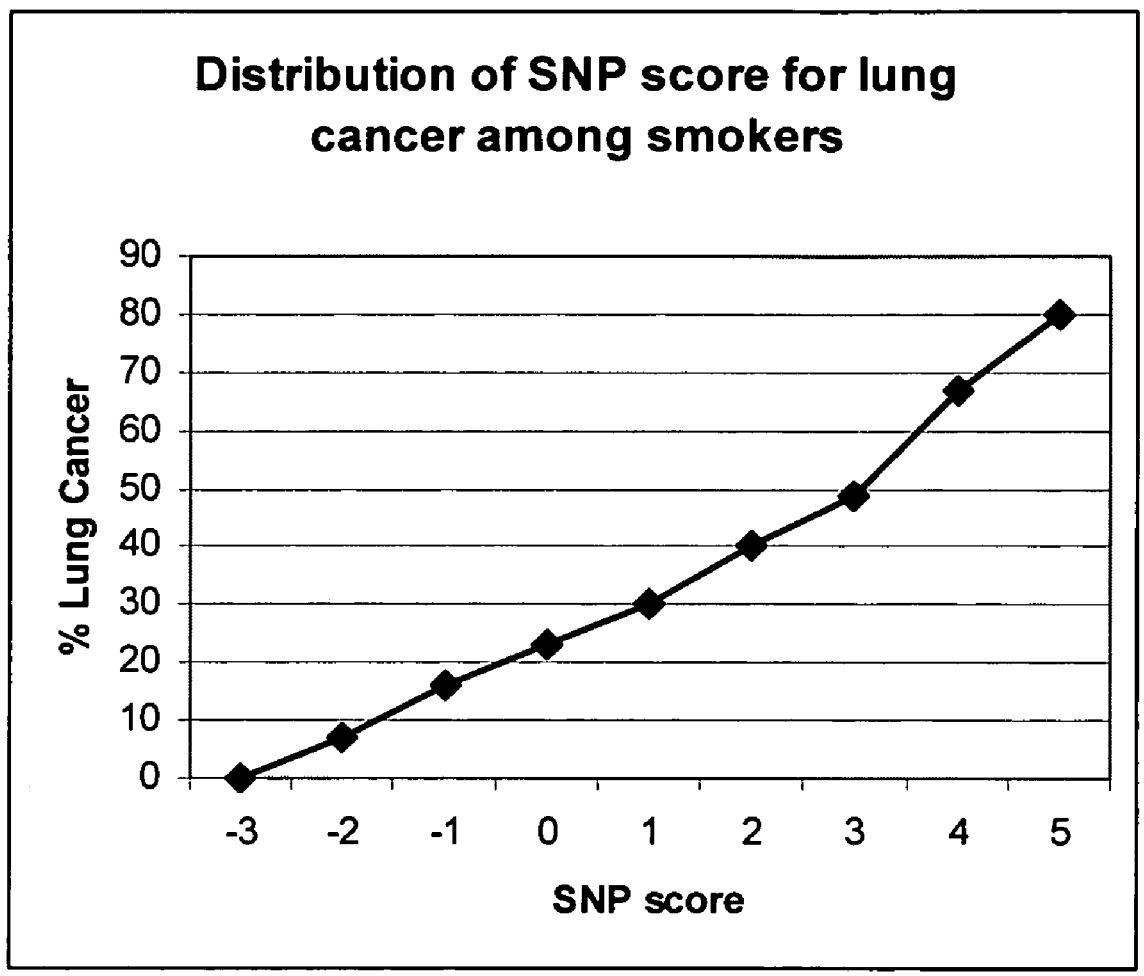
FIG. 5: depicts a graph showing net scores for protective and susceptibility polymorphisms in subjects with lung cancer.

A further combined analysis was performed using a greater number of polymorphisms. Again, this produced a linear spread of values (Table 20). When assessed as a range between −3 to +5, a linear relationship as depicted in FIG. 5 was observed. This analysis indicates that for subjects with a net score of −2 or less, there was a minimal risk of having lung cancer. In contrast, for subjects with a net score of 5+ or greater, the risk was markedly increased to 80% (see Table 20 and FIG. 5).

TABLE 20

Combined presence or absence of protective and susceptibility polymorphisms

SNP score for Lung cancer according to the presence of protective(−1) and susceptibility (+1) genotypes for all smokers

| Cohorts | <−3 | −2 | −1 | 0 | 1 | 2 | 3 | 4 | 5+ |
|---|---|---|---|---|---|---|---|---|---|
| Lung cancer N = 109 | 0 (0%) | 1 (1%) | 3 (3%) | 10 (9%) | 25 (23%) | 32 (29%) | 20 (18%) | 14 (13%) | 4 (4%) |
| Resistant smokers N = 200 | 3 (2%) | 12 (6%) | 16 (8%) | 34 (17%) | 58 (29%) | 48 (24%) | 21 (11%) | 7 (4%) | 1 (0.5%) |
| % Lung cancer | 0% | 7% | 16% | 23% | 30% | 40% | 49% | 67% | 80% |

Discussion

The methods of the invention allow the determination of risk of disease to be assessed. For example, a simple scoring system in which each polymorphism in a category (i.e. protective or susceptibility) is assigned the same value allows the combined effects of all potentially relevant polymorphisms to be factored into the analysis. In other embodiments, the methods of the invention utilize a scoring system with adjustment (weighting) for the magnitude of the effect of each individual polymorphism, and again allow all polymorphisms to be simultaneously analyzed.

In other embodiments, analyses can utilize path analysis and/or Monte-Carlo analysis where the non-genetic and genetic factors can be analyzed.

Similar results were observed in comparing the presence or absence of susceptibility and resistant polymorphisms in smokers with OCOPD, and in smokers with lung cancer and resistant smokers.

The benefit of a net susceptibility score, having been determined for a subject is that it provides the opportunity for early prophylactic and/or therapeutic intervention. Such intervention can be as simple as communicating the net susceptibility score to the subject together with an explanation of the implications of that score. This alone can cause a lifestyle or occupational change, with the resultant beneficial effect for the subject.

Other, more direct approaches to prophylaxis or therapy can also be followed. These can include pharmaceutical or other medicaments being administered directed at favorably altering the net score of the subject together with other such approaches as discussed herein.

Table 21 below presents representative examples of polymorphisms in linkage disequilibrium with the polymorphisms specified herein. Examples of such polymorphisms can be located using public databases, such as that available online at world wide web dot hapmap dot org. Specified polymorphisms are indicated in the columns marked SNP NAME. Unique identifiers are indicated in the columns marked RS NUMBER.

TABLE 21

Polymorphisms reported to be in linkage disequilibrium (unless stated) with examples of specified polymorphism.

| SNP NAME | RS NUMBER | SNP NAME | RS NUMBER | SNP NAME | RS NUMBER |
|---|---|---|---|---|---|
| | COX2 SNPs | | rs6684912 | | rs5277 |
| | rs7527769 | | rs2745559 | | rs2066823 |
| | rs7550380 | | rs12042763 | | rs4648263 |
| | rs2206594 | | rs4648250 | | rs4987012 |
| | rs6687495 | | rs4648251 | | rs20428 |
| | rs6681231 | | rs2223626 | | rs20429 |
| | rs13376484 | | rs689462 | | rs4648264 |
| | rs12064238 | | rs4648253 | | rs4648265 |
| | rs10911911 | | rs689465 | | rs4648266 |
| | rs12743673 | | rs12027712 | | rs4648267 |
| | rs10911910 | | rs689466 | | rs11567824 |
| | rs12743516 | | rs2745558 | | rs4648268 |
| | rs10911909 | | rs3918304 | | rs4648269 |
| | rs1119066 | | rs20415 | | rs4648270 |
| | rs1119065 | | rs20416 | | rs12759220 |
| | rs1119064 | | rs4648254 | | rs20430 |
| | rs10798053 | | rs11567815 | | rs4648271 |
| | rs12409744 | −765G > C | rs20417 | | rs11567825 |
| | rs10911908 | | rs4648256 | | rs4648273 |
| | rs10911907 | | rs20419 | | rs16825748 |
| | rs7416022 | | rs2734779 | | rs4648274 |
| | rs2745561 | | rs20420 | | rs16825745 |
| | rs10911906 | | rs20422 | | rs20432 |
| | rs2734776 | | rs20423 | | rs20433 |
| | rs2734777 | | rs5270 | | rs3218622 |
| | rs12084433 | | rs20424 | | rs2066826 |
| | rs2734778 | | rs5271 | | rs5278 |
| | rs2745560 | | rs4648257 | | rs4648276 |
| | rs2223627 | | rs11567819 | | rs20434 |

TABLE 21-continued

Polymorphisms reported to be in linkage disequilibrium (unless stated) with examples of specified polymorphism.

| SNP NAME | RS NUMBER | SNP NAME | RS NUMBER | SNP NAME | RS NUMBER |
|---|---|---|---|---|---|
| | rs2383517 | | rs3134591 | | rs3218623 |
| | rs4295848 | | rs3134592 | | rs3218624 |
| | rs4428839 | | rs20426 | | rs5279 |
| | rs4609389 | | rs4648258 | | rs4648278 |
| | rs4428838 | | rs11567820 | | rs13306034 |
| | rs12131210 | | rs2745557 | | rs2853803 |
| | rs2179555 | | rs11567821 | | rs4648279 |
| | rs2143417 | | rs4648259 | | rs4648281 |
| | rs2143416 | | rs4648260 | | rs4648282 |
| | rs11583191 | | rs4648261 | | rs11567826 |
| | rs2383516 | | rs4648262 | | rs4648283 |
| | rs2383515 | | rs11567822 | | rs4648284 |
| | rs10911905 | | rs11567823 | | rs4648285 |
| | rs10911904 | | rs2066824 | | rs11567827 |
| | | | rs20427 | | rs4648286 |
| | rs4648287 | | rs1042719 | | rs5744244 |
| | rs5272 | | rs3729944 | | rs360722 |
| | rs4648288 | | rs3730182 | | rs5023207 |
| | rs5273 | | rs1042720 | | rs5744246 |
| | rs5274 | | rs6879202 | | rs5744247 |
| | rs3218625 | | rs3777124 | −133 C/G | rs360721 |
| | rs4648289 | | rs1803051 | | rs4988359 |
| | rs4648290 | | rs8192451 | | rs12721559 |
| | rs1051896 | | rs4987255 | | rs5744248 |
| | rs5275 | | rs3177007 | | rs5744249 |
| | 1ADRB SNPs | | rs1126871 | | rs5744250 |
| | rs2082382 | | rs6885272 | | rs5744251 |
| | rs2082394 | | rs6889528 | | rs100000356 |
| | rs2082395 | | rs4521458 | | rs1834481 |
| | rs9325119 | | rs10463409 | | rs17215057 |
| | rs9325120 | | rs7702861 | | rs5744253 |
| | rs12189018 | | IL-18 SNPs | | rs5744254 |
| | rs11168066 | | rs187238 | | rs5744255 |
| | rs11959615 | | rs5744228 | | rs5744256 |
| | rs11958940 | | rs360718 | | rs5744257 |
| | rs4705270 | | rs360717 | | rs360720 |
| | rs10079142 | | rs5744229 | | rs5744258 |
| | rs9325121 | | rs100000353 | | rs5744259 |
| | rs11746634 | | rs5744231 | | rs5744260 |
| | rs11168067 | | rs5744232 | | rs5744261 |
| | rs9325122 | | rs7106524 | 105 A/C | rs549908 |
| | rs11957351 | | rs189667 | | PAI-1 SNPs |
| | rs11948371 | | rs12290658 | | rs6465787 |
| | rs11960649 | | rs12271175 | | rs7788533 |
| | rs1432622 | | rs11606049 | | rs6975620 |
| | rs1432623 | | rs360716 | | rs6956010 |
| | rs11168068 | | rs360715 | | rs12534508 |
| | rs17778257 | | rs360714 | | rs4729664 |
| | rs2400706 | | rs2043055 | | rs2527316 |
| | rs2895795 | | rs5744233 | | rs2854235 |
| | rs2400707 | | rs795467 | | rs10228765 |
| | rs2053044 | | rs12270240 | | rs2854225 |
| | rs17108803 | | rs100000354 | | rs2854226 |
| | rs12654778 | | rs4937113 | | rs2227707 |
| | rs11168070 | | rs100000355 | | rs2227631 |
| | rs11959427 | | rs360723 | −675 4G/5G | No rs |
| | rs1042711 | | rs5744237 | | NOS3 SNPs |
| | rs1801704 | | rs5744238 | | rs2373962 |
| Arg16Gly | rs1042713 | | rs5744239 | | rs2373961 |
| | rs1042714 | | rs7932965 | | rs6951150 |
| | rs1042717 | | rs11214103 | | rs13238512 |
| | rs1800888 | | rs5744241 | | rs10247107 |
| | rs1042718 | | rs5744242 | | rs10276930 |
| | rs3729943 | | rs5744243 | | rs10277237 |
| | rs12703107 | | rs9282804 | | rs2282679 |
| | rs6946340 | Asp298Glu | rs1799983 | | rs2282680 |
| | rs6946091 | | VDBP SNPs | | rs705117 |
| | rs6946415 | | rs222035 | | rs2070741 |
| | rs10952296 | | rs222036 | | rs2070742 |
| | rs13309715 | | rs16846943 | | rs6821541 |
| | rs10952297 | | rs7668653 | | rs222048 |
| | rs7784943 | | rs1491720 | | rs432031 |
| | rs11771443 | | rs16845007 | | rs432035 |
| | rs2243310 | | rs17830803 | | rs222049 |
| | rs1800783 | Glu416Asp | rs7041 | | rs222050 |

TABLE 21-continued

Polymorphisms reported to be in linkage disequilibrium (unless stated) with examples of specified polymorphism.

| SNP NAME | RS NUMBER | SNP NAME | RS NUMBER | SNP NAME | RS NUMBER |
|---|---|---|---|---|---|
| | rs3918155 | Lys420Thr | rs4588 | | rs12510584 |
| | rs3918156 | | rs3737553 | | rs17467825 |
| | rs2566519 | | rs9016 | | GSTP1 SNPs |
| | rs3918157 | | rs1352846 | | rs656652 |
| | rs3918158 | | rs222039 | | rs625978 |
| | rs3918159 | | rs3775154 | | rs6591251 |
| | rs2566516 | | rs222040 | | rs12278098 |
| | rs3918225 | | rs843005 | | rs612020 |
| | rs3918160 | | rs222041 | | rs12284337 |
| | rs1800779 | | rs7672977 | | rs12574108 |
| | rs2243311 | | rs705121 | | rs6591252 |
| | rs3918161 | | rs11723621 | | rs597717 |
| | rs10952298 | | rs2298850 | | rs688489 |
| | rs2070744 | | rs705120 | | rs597297 |
| | rs3918226 | | rs2298851 | | rs6591253 |
| | rs3918162 | | rs844806 | | rs6591254 |
| | rs3918163 | | rs1491709 | | rs7927381 |
| | rs3918164 | | rs705119 | | rs7940813 |
| | rs3918165 | | rs6845925 | | rs593055 |
| | rs1800781 | | rs12640255 | | rs7927657 |
| | rs13310854 | | rs12644050 | | rs614080 |
| | rs13310763 | | rs6845869 | | rs7941395 |
| | rs2853797 | | rs12640179 | | rs7941648 |
| | rs13311166 | | rs222042 | | rs7945035 |
| | rs13310774 | | rs3187319 | | rs2370141 |
| | rs2853798 | | rs222043 | | rs2370142 |
| | rs11974098 | | rs842999 | | rs7949394 |
| | rs3918166 | | rs222044 | | rs7949587 |
| | rs3730001 | | rs222045 | | rs6591255 |
| | rs3918167 | | rs16846912 | | rs8191430 |
| | rs3918168 | | rs222046 | | rs6591256 |
| | rs3918169 | | rs705118 | | rs8191431 |
| | rs3918170 | | rs222047 | | rs8191432 |
| | rs3793342 | | rs13142062 | | rs7109914 |
| | rs3793341 | | rs843000 | | rs4147580 |
| | rs1549758 | | rs3755967 | | rs8191436 |
| | rs1007311 | | rs1491710 | | rs8191437 |
| | rs9282803 | | rs2282678 | | rs17593068 |
| | rs8191438 | | rs2069718 | | rs7145047 |
| | rs8191439 | | rs3087272 | | rs7141735 |
| | rs8191440 | | rs2069719 | | rs11558264 |
| | rs8191441 | | rs9282708 | | rs6647 |
| | rs1079719 | | rs2069720 | | rs8350 |
| | rs1871041 | | rs1042274 | | rs2230075 |
| | rs4147581 | | rs2069721 | | rs1049800 |
| | rs8191444 | | rs2069734 | S allele | rs17580 |
| | rs8191445 | | rs2069722 | | rs2854258 |
| | rs2370143 | | rs2234687 | | rs2753937 |
| | rs8191446 | | rs7957366 | | rs2749547 |
| | rs3891249 | | rs2069723 | | rs1243162 |
| | rs8191447 | | rs2069724 | | rs2753938 |
| | rs12796085 | | rs2069725 | | rs2070709 |
| | rs8191448 | | rs4394909 | | rs17090719 |
| | rs762803 | | rs2069726 | | rs11846959 |
| | rs8191449 | | rs2069727 | | rs1802962 |
| Ile105Val | rs947894 | | IL-13 SNPs | | rs2749521 |
| | rs4986948 | −1055 C/T | rs1800925 | | rs2753939 |
| | rs675554 | | rs11575055 | | rs1802959 |
| | rs749174 | | rs2069755 | | rs1802961 |
| | rs8191450 | | rs2069741 | | rs1050469 |
| | rs743679 | | rs2069742 | Z allele | no rs |
| | rs1799811 | | rs2069743 | | rs1050520 |
| | rs11553890 | | rs2069756 | | rs12077 |
| | rs4986949 | | rs3212142 | | rs12233 |
| | rs8191451 | | rs2066960 | | rs13170 |
| | rs1871042 | | rs1295687 | | rs1303 |
| | rs11553892 | | rs3212145 | | rs1802960 |
| | rs4891 | | rs2069744 | | rs1243163 |
| | rs6413486 | | rs2069745 | | rs2073333 |
| | rs5031031 | | rs2069746 | | rs1243164 |
| | rs947895 | | rs2069747 | | rs1144409 |
| | IFN-SNPs | | rs2069748 | | rs7142803 |
| | rs2069707 | | rs1295686 | | rs1243165 |
| | rs3814242 | Arg130Gln | rs20541 | | rs1051052 |
| | rs2069709 | | rs2069749 | | rs1243166 |

TABLE 21-continued

Polymorphisms reported to be in linkage disequilibrium (unless stated) with examples of specified polymorphism.

| SNP NAME | RS NUMBER | SNP NAME | RS NUMBER | SNP NAME | RS NUMBER |
|---|---|---|---|---|---|
|  | rs2069710 |  | rs1295685 |  | rs11628917 |
|  | rs2069711 |  | rs848 |  | rs11832 |
|  | rs2069712 |  | rs2069750 |  | rs9944155 |
| 874 A/T | rs2430561 |  | rs847 | 1237 G/A | rs11568814 |
|  | rs2069713 |  | a1-antitrypsin SNPs |  | rs877081 |
|  | rs1861494 |  | rs709932 |  | rs877082 |
|  | rs2234685 |  | rs11558261 |  | rs877083 |
|  | rs1861493 |  | rs20546 |  | rs877084 |
|  | rs2069714 |  | rs11558263 |  | rs875989 |
|  | rs2069715 |  | F1028580 |  | rs9944117 |
|  | rs2069716 |  | rs7145770 |  | rs1884546 |
|  | rs2069717 |  | rs2239652 |  | rs1884547 |
|  | rs1885065 |  | rs2735442 |  | rs8046608 |
|  | rs1884548 |  | rs2569693 |  | rs5743264 |
|  | rs1243167 |  | rs281439 |  | rs5743266 |
|  | rs17751614 |  | rs281440 |  | rs2076752 |
|  | rs1884549 |  | rs2569694 |  | rs5743267 |
|  | rs1243168 |  | rs11575073 |  | rs8061316 |
|  | rs17090693 |  | rs2569695 |  | rs8061636 |
|  | rs17824597 |  | rs2075741 |  | rs16948754 |
|  | TNFa SNPs |  | rs11575074 |  | rs7206340 |
|  | rs1799964 |  | rs2569696 |  | rs2076753 |
|  | rs1800630 |  | rs2735439 |  | rs2067085 |
|  | rs1799724 |  | rs2569697 |  | rs16948755 |
| +489 G/A | rs1800610 |  | rs2075742 |  | rs2111235 |
|  | rs309362 |  | rs2569698 |  | rs2111234 |
|  | rs3093664 |  | rs11669397 |  | rs7190413 |
| −308 G/A | rs1800629 (1) |  | rs901886 |  | rs7206582 |
|  | SMAD3 SNPs |  | rs885742 |  | rs8045009 |
| C89Y | C89Y no rs (2) |  | rs2569699 |  | rs6500328 |
|  | ICAM1 |  | rs1056538 |  | rs7500036 |
|  | rs1799969 |  | rs11549918 |  | rs8057341 |
|  | rs5493 |  | rs2569700 |  | rs12918060 |
|  | rs5030381 |  | rs2228615 |  | rs7204911 |
|  | rs5494 |  | rs2569701 |  | rs7500826 |
|  | rs3093033 |  | rs2569702 |  | rs4785449 |
|  | rs5495 |  | rs2735440 |  | rs12922299 |
|  | rs1801714 |  | rs2569703 |  | rs11649521 |
|  | rs13306429 |  | rs10418913 |  | rs13339578 |
|  | rs2071441 |  | rs1056536 |  | rs17221417 |
|  | rs5496 |  | rs2569704 |  | rs13331327 |
|  | rs5497 |  | rs11673661 |  | rs11642482 |
|  | rs13306430 |  | rs2569705 |  | rs11642646 |
| E469K | rs5498 |  | rs10402760 |  | rs17312836 |
|  | rs5030400 |  | rs2569706 |  | rs5743268 |
|  | rs2071440 |  | rs2569707 |  | rs5743269 |
|  | rs5499 |  | rs2735441 |  | rs5743270 |
|  | rs3093032 |  | rs2436545 |  | rs12925051 |
|  | rs1057981 |  | rs2436546 |  | rs12929565 |
|  | rs5500 |  | rs2916060 |  | rs13380733 |
|  | rs5501 |  | rs2916059 |  | rs13380741 |
|  | rs5030383 |  | rs2916058 |  | rs11647841 |
|  | rs281436 |  | rs2569708 |  | rs10451131 |
|  | rs923366 |  | rs12972990 |  | rs2066842 |
|  | rs281437 |  | rs735747 |  | rs5743271 |
|  | rs3093030 |  | rs885743 |  | rs7498256 |
|  | rs5030384 |  | NOD2 SNPs |  | rs5743272 |
|  | rs5030385 |  | rs4785224 |  | rs5743273 |
|  | rs3810159 |  | rs5743261 |  | rs2076754 |
|  | rs281438 |  | rs5743262 |  | rs2066843 |
|  | rs3093029 |  | rs5743263 |  | rs1078327 |
|  | rs5743274 |  | rs11645386 |  | rs1031101 |
|  | rs1861759 |  | rs7187857 |  | rs10824795 |
|  | rs5743275 |  | rs8061960 |  | rs10824794 |
|  | rs5743276 |  | rs5743294 |  | rs920725 |
|  | rs2066844 |  | rs2357791 |  | rs7916582 |
|  | rs5743277 |  | rs7359452 |  | rs920724 |
|  | rs5743278 |  | rs7203344 |  | rs16933335 |
|  | rs6413461 |  | rs5743295 |  | rs11003125 |
|  | rs3813758 |  | rs5743296 |  | rs7100749 |
|  | rs5743279 |  | rs3135499 |  | rs11003124 |
|  | rs5743280 |  | rs5743297 |  | rs7084554 |
|  | rs5743281 |  | rs5743298 |  | rs7096206 |
|  | rs4785225 |  | rs5743299 |  | rs11003123 |

TABLE 21-continued

Polymorphisms reported to be in linkage disequilibrium (unless stated) with examples of specified polymorphism.

| SNP NAME | RS NUMBER | SNP NAME | RS NUMBER | SNP NAME | RS NUMBER |
|---|---|---|---|---|---|
|  | rs16948773 |  | rs3135500 |  | rs11575988 |
|  | rs9931711 |  | rs5743300 |  | rs11575989 |
|  | rs17313265 |  | rs8056611 |  | rs7095891 |
|  | rs11646168 |  | rs2357792 |  | rs4647963 |
|  | rs9925315 |  | rs12600253 |  | rs8179079 |
|  | rs5743284 |  | rs12598306 |  | rs5030737 |
|  | rs5743285 |  | rs7205423 | 161 G/A | rs1800450 |
|  | rs751271 |  | rs718226 |  | rs1800451 |
|  | rs748855 |  | MBL2 SNPs |  | rs12246310 |
|  | rs1861758 |  | rs7899547 |  | rs12255312 |
|  | rs13332952 |  | rs10824797 |  | rs11003122 |
|  | rs7198979 |  | rs11003131 |  | rs1982267 |
|  | rs1861757 |  | rs930506 |  | rs1982266 |
|  | rs7203691 |  | rs930505 |  | rs4935047 |
|  | rs5743286 |  | rs11003130 |  | rs4935046 |
|  | rs5743287 |  | rs2384044 |  | rs10824793 |
|  | rs10521209 |  | rs2384045 |  | rs1838066 |
| Gly881Arg | rs2066845 |  | rs5027257 |  | rs1838065 |
|  | rs5743289 |  | rs2384046 |  | rs930509 |
|  | rs8063130 |  | rs12263867 |  | rs930508 |
|  | rs2076756 |  | rs11003129 |  | rs930507 |
|  | rs12920425 |  | rs12221393 |  | CMA1 SNPs |
|  | rs12920040 |  | rs2165811 |  | rs1956920 |
|  | rs12920558 |  | rs12782244 |  | rs1956921 |
|  | rs12919099 |  | rs11003128 | −1903 G/A | rs1800875 |
|  | rs12920721 |  | rs17664818 |  | rs1800876 |
|  | rs2076755 |  | rs7475766 |  | rs3759635 |
|  | rs5743290 |  | rs10824796 |  | rs1956922 |
|  | rs5743291 |  | rs16933417 |  | rs1956923 |
|  | rs11642651 |  | rs2165810 |  | NAT2 SNPs |
|  | rs1861756 |  | rs11003127 |  | rs11780272 |
|  | rs749910 |  | rs3925313 |  | rs2101857 |
|  | rs4990643 |  | rs7094151 |  | rs13363820 |
|  | rs1077861 |  | rs7071882 |  | rs6984200 |
|  | rs5743292 |  | rs12264958 |  | rs13277605 |
|  | rs9921146 |  | rs11003126 |  | rs9987109 |
|  | rs7820330 |  | rs7596849 | −366 G/A | rs9550373 |
|  | rs7460995 |  | rs4848306 |  | rs11542984 |
|  | rs2087852 |  | rs3087257 |  | rs4769055 |
|  | rs2101684 |  | rs7556811 |  | rs17074937 |
|  | rs7011792 |  | rs7556903 |  | rs9671065 |
|  | rs1390358 |  | rs6743438 |  | rs9579645 |
|  | rs923796 |  | rs6743427 |  | rs9579646 |
|  | rs4546703 |  | rs6761336 |  | rs4075131 |
|  | rs4634684 |  | rs6761335 |  | rs4075132 |
|  | rs2410556 |  | rs6743338 |  | rs9315043 |
|  | rs11996129 |  | rs6761245 |  | rs9315044 |
|  | rs4621844 |  | rs6761237 |  | rs4597169 |
|  | rs11785247 |  | rs6743330 |  | rs9578037 |
|  | rs1115783 |  | rs6743326 |  | rs9578196 |
|  | rs1115784 |  | rs6743322 |  | rs4293222 |
|  | rs1961456 |  | rs6761220 |  | rs10507391 |
|  | rs1112005 |  | rs6761218 |  | rs12429692 |
|  | rs11782802 |  | rs5021469 |  | rs4769871 |
|  | rs973874 |  | rs6710598 |  | rs4769872 |
|  | rs1495744 |  | rs1143623 |  | rs4769873 |
|  | rs7832071 |  | rs1143624 |  | rs12430051 |
|  | rs1805158 |  | rs2708920 |  | rs9315045 |
|  | rs1801279 |  | rs1143625 |  | rs9670278 |
|  | rs1041983 |  | rs2853545 |  | rs4503649 |
|  | rs1801280 |  | rs2708921 |  | rs9508832 |
|  | rs4986996 |  | rs1143626 |  | rs9670460 |
|  | rs12720065 |  | rs3087258 |  | rs3885907 |
|  | rs4986997 | C-511T | rs16944 |  | rs3922435 |
|  | rs1799929 |  | rs3917346 |  | rs9551957 |
| Arg197Gln | rs1799930 |  | rs4986987 |  | rs12018461 |
|  | rs1208 |  | rs1143627 |  | rs9551958 |
|  | rs1799931 |  | MEN SNPs |  | rs10467440 |
|  | rs2552 | Tyr113His | rs1051740 (2) |  | rs12017304 |
|  | rs4646247 | His139Arg | rs2234922 (2) |  | rs9551959 |
|  | rs971473 |  | ALOX5AP SNPs |  | rs11617473 |
|  | rs721398 |  | rs4076128 |  | rs11147438 |
|  | IL-1B SNPs |  | rs9508830 |  | rs10162089 |
|  | rs10169916 |  | rs4073259 |  | rs9551960 |
|  | rs13009179 |  | rs4073260 |  | rs9285075 |

TABLE 21-continued

Polymorphisms reported to be in linkage disequilibrium (unless stated) with examples of specified polymorphism.

| SNP NAME | RS NUMBER | SNP NAME | RS NUMBER | SNP NAME | RS NUMBER |
|---|---|---|---|---|---|
|  | rs4849127 |  | rs11616333 |  | rs12431114 |
|  | rs4849126 |  | rs4073261 |  | rs4254165 |
|  | rs7558108 |  | rs4075474 |  | rs4360791 |
|  | rs13032029 |  | rs4075473 |  | rs17612031 |
|  | rs13013349 |  | rs9670115 |  | rs3803277 |
|  | rs12623093 |  | rs9315042 |  | rs3803278 |
|  | rs3087255 |  | rs3809376 |  | rs12429469 |
|  | rs3087256 |  | rs12877064 |  | rs17612099 |
|  | rs6721954 |  | rs9508831 |  | rs9550576 |
|  | rs12621220 |  | rs9670503 |  | rs4356336 |
|  | rs4584668 |  | rs2075800 |  | rs2734714 |
|  | rs4238137 |  | CLCA1 SNPs |  | rs6661730 |
|  | rs17612127 |  | rs2791519 |  | rs2753377 |
|  | rs4147063 |  | rs2791518 |  | rs2753378 |
|  | rs4147064 |  | rs5744302 |  | rs2145412 |
|  | rs4147062 |  | rs1321697 |  | rs2180762 |
|  | rs9315046 |  | rs2753338 |  | rs1005569 |
|  | rs9506352 |  | rs2791517 |  | rs5744325 |
|  | rs9670531 |  | rs5744303 |  | rs5744326 |
|  | rs9671182 |  | rs2734706 |  | rs1985554 |
|  | rs9315047 |  | rs2753345 |  | rs1985555 |
|  | rs17690694 |  | rs2753347 |  | rs100000102 |
|  | rs9652070 |  | rs2753348 |  | rs100000103 |
|  | rs17074966 |  | rs2753349 |  | rs1969719 |
|  | rs4387455 |  | rs5744304 |  | rs2390102 |
|  | rs4254166 |  | rs5744305 |  | rs5744329 |
|  | rs4075692 |  | rs1358826 |  | rs1407142 |
|  | rs17690748 |  | rs2753359 |  | rs2753384 |
|  | rs9671124 |  | rs5744306 |  | rs2753385 |
|  | rs9671125 |  | rs2734711 |  | rs5744330 |
|  | rs9741436 |  | rs5744307 |  | rs5744331 |
|  | rs9578197 |  | rs2734712 |  | rs926064 |
|  | rs4769056 |  | rs2753361 |  | rs926065 |
|  | rs11147439 |  | rs2753364 |  | rs926066 |
|  | rs12721459 |  | rs1555389 |  | rs926067 |
|  | rs4769874 |  | rs2753365 |  | rs2753386 |
|  | HSP70 HOM SNPs |  | rs100000100 |  | rs2180764 |
|  | rs1043618 |  | rs100000101 |  | rs2734689 |
|  | rs11576009 |  | rs5744310 |  | rs5744332 |
|  | rs11557922 |  | rs5744311 |  | rs5744333 |
|  | rs11576010 |  | rs5744312 |  | rs11161837 |
|  | rs1008438 |  | rs4656114 |  | rs5744335 |
|  | rs11576011 |  | rs5744313 |  | rs2038485 |
|  | rs4713489 |  | rs2753367 |  | rs3765989 |
|  | rs16867582 |  | rs4656115 |  | rs2734690 |
|  | rs12526722 |  | rs2734713 |  | rs5744336 |
|  | rs6933097 |  | rs5744314 |  | rs2734691 |
|  | rs12213612 |  | rs5744315 |  | rs2734692 |
|  | rs481825 |  | rs5744316 |  | rs5744337 |
|  | rs7757853 |  | rs5744317 |  | rs5744338 |
|  | rs7757496 |  | rs5744318 |  | rs2734694 |
|  | rs9469057 |  | rs926063 |  | rs5744339 |
|  | rs12182397 |  | rs5744319 |  | rs100000104 |
|  | rs16867580 |  | rs5744320 |  | rs2791515 |
|  | rs2075799 |  | rs5744321 |  | rs4656116 |
|  | rs482145 |  | rs5744322 |  | rs5744342 |
|  | rs2227957 |  | rs5744323 |  | rs5744343 |
| T2437C | rs2227956 |  | rs5744324 |  | rs2180761 |
|  | rs2227955 |  | rs2791516 |  | rs5744344 |
|  | rs5744345 |  | rs5744443 |  | rs6032038 |
|  | rs1358825 |  | rs5744444 |  | rs6032039 |
|  | rs2145410 |  | rs3138074 |  | rs2267863 |
|  | rs2734695 |  | rs13166911 |  | rs6124692 |
|  | rs5744346 |  | rs2563310 | +49 C/T | No rs |
|  | rs5744347 |  | rs2569193 |  | rs17333103 |
|  | rs100000105 |  | rs2569192 |  | rs17333180 |
|  | rs5744349 |  | rs5744446 |  | rs1983649 |
|  | rs4655913 |  | rs5744447 |  | rs16989785 |
|  | rs1321696 |  | rs5744448 |  | rs17424356 |
|  | rs5744352 |  | rs3138076 |  | rs6017500 |
|  | rs11583355 |  | rs12519656 |  | rs6032040 |
|  | rs100000106 |  | rs5744449 |  | rs6017501 |
|  | rs1321695 |  | rs2915863 |  | rs2664581 |
| +13924 T/A | rs1321694 |  | rs3138078 |  | rs17424474 |
|  | rs2791514 |  | rs6875483 |  | rs17333381 |

TABLE 21-continued

Polymorphisms reported to be in linkage disequilibrium (unless stated) with examples of specified polymorphism.

| SNP NAME | RS NUMBER | SNP NAME | RS NUMBER | SNP NAME | RS NUMBER |
|---|---|---|---|---|---|
| | rs2734696 | | rs2569191 | | rs1053826 |
| | rs5744354 | | rs5744451 | | rs2664533 |
| | rs2791513 | | rs5744452 | | rs1053831 |
| | rs2753332 | | rs100000098 | | rs2664520 |
| | rs2791512 | | rs17118968 | | rs2267864 |
| | rs2791511 | | rs5744455 | | rs13038355 |
| | rs2734697 | −159 C/T | rs2569190 | | rs13043296 |
| | CD14 SNPs | | rs2569189 | | rs13039213 |
| | rs6877461 | | rs2563303 | | rs6104049 |
| | rs3822356 | | rs3138079 | | rs13043503 |
| | rs6877437 | | rs2228049 | | rs6104050 |
| | rs12153256 | | rs13763 | | rs17424578 |
| | rs11554680 | | rs11556179 | | rs17424613 |
| | rs12109040 | | rs4914 | | rs6017502 |
| | rs12517200 | | Elafin SNPs | | rs6094101 |
| | rs5744430 | | rs2868237 | | rs6130778 |
| | rs5744431 | | rs4632412 | | rs6130779 |
| | rs100000092 | | rs7347427 | | rs6104051 |
| | rs5744433 | | rs6032032 | | rs6104052 |
| | rs100000093 | | rs10854230 | | ADBR2 SNPs |
| | rs4912717 | | rs7347426 | | rs2082382 |
| | rs100000094 | | rs8183548 | | rs2082394 |
| | rs100000095 | | rs6104047 | | rs2082395 |
| | rs100000096 | | rs6513967 | | rs9325119 |
| | rs6864930 | | rs13038813 | | rs9325120 |
| | rs100000097 | | rs8118673 | | rs12189018 |
| | rs6864583 | | rs7346463 | | rs11168066 |
| | rs6864580 | | rs7362841 | | rs11959615 |
| | rs6889418 | | rs13042694 | | rs11958940 |
| | rs6889416 | | rs13038342 | | rs4705270 |
| | rs5744440 | | rs7363327 | | rs10079142 |
| | rs5744441 | | rs6073668 | | rs9325121 |
| | rs5744442 | | rs13044826 | | rs11746634 |
| | rs11168067 | | rs1800468 | | rs542603 |
| | rs9325122 | | rs4987025 | | rs574939 |
| | rs11957351 | | rs1800469 | | rs573764 |
| | rs11948371 | | rs11466314 | | rs7102189 |
| | rs11960649 | | rs12977628 | | rs575727 |
| | rs1432622 | | rs12977601 | | rs552306 |
| | rs1432623 | | rs12985978 | | rs634607 |
| | rs11168068 | | rs11466315 | | rs12286876 |
| | rs17778257 | | rs11551223 | | rs12285331 |
| | rs2400706 | | rs11551226 | | rs519806 |
| | rs2895795 | | rs11466316 | | rs12283571 |
| | rs2400707 | | rs13306706 | | rs2839969 |
| | rs2053044 | | rs13306707 | | rs2000609 |
| | rs17108803 | | rs13306708 | | rs7125865 |
| | rs12654778 | | rs9282871 | | rs570662 |
| | rs11168070 | Leu10Pro | rs1982073 | | rs11225427 |
| | rs11959427 | | rs1800471 | | rs484915 |
| | rs1042711 | | rs13447341 | | rs470307 |
| | rs1801704 | | rs11466318 | | rs2408490 |
| | rs1042713 | | rs12976890 | | rs12279710 |
| Gln27Glu | rs1042714 | | rs12978333 | | rs685265 |
| | rs1042717 | | rs10420084 | | rs7107224 |
| | rs1800888 | | rs10418010 | | rs1155764 |
| | rs1042718 | | rs12983775 | | rs534191 |
| | SOD3 SNPs | | rs12462166 | | rs509332 |
| Arg213Gly | rs1799895 (2) | | rs2241715 | | rs12283759 |
| | TGFB1 SNPs | | rs9749548 | | rs2105581 |
| | rs1529717 | | rs7258445 | | rs470206 |
| | rs1046909 | | rs11466320 | | rs533621 |
| | rs2241712 | | rs11466321 | −1607 G/GG | rs1799750 |
| | rs2241713 | | rs8108052 | | rs470211 |
| | rs2241714 | | rs6508976 | | rs470146 |
| | rs11673525 | | rs8108632 | | rs2075847 |
| | rs2873369 | | rs11466324 | | rs473509 |
| | rs11083617 | | rs2241716 | | rs498186 |
| | rs11083616 | | rs2241717 | | GSTM1 polymorphism |
| | rs4803458 | | rs2288873 | Null | Null allele No rs (2) |
| | rs11670143 | | rs12973435 | | MMP9 SNPs |
| | rs1982072 | | rs2014015 | | rs11696804 |
| | rs11668109 | | rs1989457 | | rs6104416 |
| | rs13345981 | | rs10406816 | | rs3933239 |

TABLE 21-continued

Polymorphisms reported to be in linkage disequilibrium (unless stated) with examples of specified polymorphism.

| SNP NAME | RS NUMBER | SNP NAME | RS NUMBER | SNP NAME | RS NUMBER |
|---|---|---|---|---|---|
| | rs11666933 | | rs8102918 | | rs3933240 |
| | rs11466310 | | rs4803455 | | rs6094237 |
| | rs11466311 | | MMP1 SNPs | | rs11697325 |
| | rs2317130 | | rs529381 | | rs6130988 |
| | rs4803457 | | rS1144396 | | rs6073983 |
| | rs3087453 | | rs504875 | | rs6130989 |
| | rs1800820 | | rs526215 | | rs6130990 |
| | rs1054797 | | rs12280880 | | rs10211842 |
| | rs6073984 | | rs8125587 | | TIMP3 SNPs |
| | rs6073985 | | rs3918253 | | rs5754289 |
| | rs8121146 | | rs2274755 | | rs5754290 |
| | rs6032620 | | rs2664538 | | rs9606994 |
| | rs11698788 | | rs3918254 | | rs7285034 |
| | rs6032621 | | rs6130993 | | rs13433582 |
| | rs6065912 | | rs3918255 | | rs1962223 |
| | rs6104417 | | rs2236416 | | rs8137129 |
| | rs3848720 | | rs6130994 | | rs1807471 |
| | rs13040272 | | rs3918256 | | rs7290885 |
| | rs6104418 | | rs3918281 | | rs5749511 |
| | rs3848721 | | rs3787268 | | rs11703366 |
| | rs3848722 | | rs3918257 | | rs4990774 |
| | rs6104419 | | rs6017725 | −1296 T/C | rs9619311 |
| | rs4810482 | | rs6032623 | | rs2234921 |
| | rs3761157 | | rs3918258 | | rs2234920 |
| | rs3761158 | | rs2250889 | | rs16991235 |
| | rs3761159 | | rs3918259 | | rs4638893 |
| | rs8113877 | | rs3918260 | | rs12169569 |
| | rs6065913 | | rs13969 | | rs5998639 |
| | rs6104420 | | rs6104427 | | rs7284166 |
| | rs6104421 | | rs6104428 | | rs5749512 |
| | rs3918240 | | rs2274756 | | |
| | rs6104422 | | rs6017726 | | |
| | rs3918278 | | rs3918261 | | |
| | rs3918241 | | rs6032624 | | |
| −1562 C/T | rs3918242 | | rs3918262 | | |
| | rs3918243 | | rs3918263 | | |
| | rs3918279 | | rs3918264 | | |
| | rs3918280 | | rs6130995 | | |
| | rs4578914 | | rs6130996 | | |
| | rs6017724 | | rs3918265 | | |
| | rs3918244 | | rs3918266 | | |
| | rs3918245 | | rs3918267 | | |
| | rs6130992 | | rs6073987 | | |
| | rs3918247 | | rs6073988 | | |
| | rs3918248 | | rs3918282 | | |
| | rs3918249 | | rs1802909 | | |
| | rs6104423 | | rs13925 | | |
| | rs6104424 | | rs20544 | | |
| | rs6104425 | | rs1056628 | | |
| | rs6104426 | | rs1802908 | | |
| | rs3918250 | | rs2664517 | | |
| | rs1805089 | | rs9509 | | |
| | rs3918251 | | rs3918268 | | |
| | rs13040572 | | rs3918269 | | |
| | rs13040580 | | rs3918270 | | |
| | rs3918252 | | MMP12 SNPs | | |
| | rs8125581 | −82 A/G | rs2276109 (2) | | |

(1 = no other SNPs reported to be in LD, 2 = no other SNPS reported to be in LD)

INDUSTRIAL APPLICATION

The present invention is directed to methods for assessing a subject's risk of developing a disease. The methods include the analysis of polymorphisms herein shown to be associated with increased or decreased risk of developing a disease, or the analysis of results obtained from such an analysis, and the determination of a net risk score. Methods of treating subjects at risk of developing a disease herein described are also provided. Additional information regarding the above material, or subparts thereof, can be found in U.S. patent application Ser. No. 10/479,525, filed Jun. 16, 2004; and PCT Application No. PCT/NZ02/00106, filed Jun. 5, 2002, which further designates New Zealand Application No. 512169, filed Jun. 5, 2001; New Zealand Application No. 513016, filed Jul. 17, 2001, and New Zealand Application No. 514275, filed Sep. 18, 2001, all of which are incorporated by reference in their entireties. Additional information can also be found in PCT application Nos. PCT/NZ2006/000103 and PCT/NZ2006/000104, filed May 10, 2006, entitled "Methods and Compositions for Assessment of Pulmonary Function and Disorders" and "Methods of Analysis of Polymorphisms and Uses Thereof", both of which are incorporated in their entireties by reference. PCT Application No. PCT/NZ2006/000103 claims priority to: NZ application No. 539934, filed May 10, 2005; NZ application No. 541935, filed Aug. 19, 2005; and JP application No. 2005-360523, filed Dec. 14, 2005, all of which are incorporated by reference in their entireties. PCT Application No. PCT/NZ2006/000104 claims priority to: NZ application No. 540249, filed May 20, 2005; and NZ application No. 541842, filed Aug. 15, 2005, all of which are incorporated in their entireties by reference. Additional information can also be found in U.S. patent application Ser. No. 11/432,736, filed concurrently with the instant application, entitled "Methods of Analysis of Polymorphisms and Uses Thereof," incorporated in its entirety.

Publications

1. Sandford A J, et al., 1999. Z and S mutations of the α1-antitrypsin gene and the risk of chronic obstructive pulmonary disease. Am J Respir Cell Mol Biol. 20; 287-291.
2. Maniatis, T., Fritsch, E. F. and Sambrook, J., Molecular Cloning Manual. 1989.
3. Papafili A, et al., 2002. Common promoter variant in cyclooxygenase-2 represses gene expression. Arterioscler-Thromb Vasc Biol. 20; 1631-1635.
4. Ukkola, O., Erkkilä, P. H., Savolainen, M. J. & Kesäniemi, Y. A. 2001. Lack of association between polymorphisms of catalase, copper zinc superoxide dismutase (SOD), extracellular SOD and endothelial nitric oxide synthase genes and macroangiopathy in patients with type 2 diabetes mellitus. J Int Med 249; 451-459.
5. Smith CAD & Harrison D J, 1997. Association between polymorphism in gene for microsomal epoxide hydrolase and susceptibility to emphysema. Lancet. 350; 630-633.
6. Lorenz E, et al., 2001. Determination of the TLR4 genotype using allele-specific PRC. Biotechniques. 31; 22-24.
7. Cantlay A M, Smith C A, Wallace W A, Yap P L, Lamb D, Harrison D J. Heterogeneous expression and polymorphic genotype of glutathione S-transferases in human lung. Thorax. 1994, 49(10):1010-4.

All patents, publications, scientific articles, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Any and all materials and information from any such patents, publications, scientific articles, web sites, electronically available information, and other referenced materials or documents can be physically incorporated into this specification.

The specific methods and compositions described herein are representative of various embodiments or preferred embodiments and are exemplary only and not intended as limitations on the scope of the invention. Other objects, aspects, examples and embodiments will occur to those skilled in the art upon consideration of this specification, and are encompassed within the spirit of the invention as defined by the scope of the claims. It will be readily apparent to one skilled in the art that varying substitutions and modifications can be made to the invention disclosed herein without departing from the scope and spirit of the invention. The invention illustratively described herein suitably can be practiced in the absence of any element or elements, or limitation or limitations, which is not specifically disclosed herein as essential. Thus, for example, in each instance herein, in embodiments or examples of the present invention, any of the terms "comprising", "consisting essentially of", and "consisting of" can be replaced with either of the other two terms in the specification, thus indicating additional examples, having different scope, of various alternative embodiments of the invention. Also, the terms "comprising", "including", "containing", etc. are to be read expansively and without limitation. The methods and processes illustratively described herein suitably can be practiced in differing orders of steps, and that they are not necessarily restricted to the orders of steps indicated herein or in the claims. It is also that as used herein and in the appended claims, the singular forms "a," "an," and "the" include plural reference unless the context clearly dictates otherwise. Thus, for example, a reference to "a host cell" includes a plurality (for example, a culture or population) of such host cells, and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by the Applicant.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed can be resorted to by those skilled in the art, and that such modifications and variations are considered to be within the scope of this invention as defined by the appended indicative claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following indicative claims. In addition, where features or aspects of the invention are described in terms of Markush groups, those skilled in the art will recognize that the invention is also thereby described in terms of any individual member or subgroup of members of the Markush group.

The invention claimed is:

1. A method of assessing a human subject's risk of developing a disease having a genetic basis, comprising:
obtaining a biological sample from a human subject;
analyzing said sample for a presence or absence of at least one protective polymorphism and for a presence or absence of at least one susceptibility polymorphism, wherein said at least one protective polymorphism and said at least one susceptibility polymorphism are associated with a disease having a genetic basis, and wherein the total number of susceptibility and protective polymorphisms analyzed is four or greater;
assigning a positive score for each protective polymorphism and a negative score for each susceptibility polymorphism or vice versa; and
calculating a net score for said subject, said net score representing a balance between a combined value of the at least one protective polymorphism and the combined value of the at least one susceptibility polymorphism present in the subject sample;
wherein the disease is selected from the group consisting of lung cancer, chronic obstructive pulmonary disease (COPD), occupational chronic obstructive pulmonary disease (OCOPD), and emphysema, and wherein a net protective score is predictive of a reduced risk of developing said disease and a net susceptibility score is predictive of an increased risk of developing said disease.

2. The method according to claim 1, wherein the value assigned to each protective polymorphism is the same.

3. The method according to claim 1, wherein the value assigned to each susceptibility polymorphism is the same.

4. The method according to claim 1, wherein each protective polymorphism has a negative value and each susceptibility polymorphism having a positive value.

5. The method according to claim 1, wherein each protective polymorphism has a positive value and each susceptibility polymorphism has a negative value.

6. The method according to claim 1, wherein when the disease is a lung disease, the protective polymorphisms analysed is selected from one or more of the group consisting of:

+760GG or +760CG within the gene encoding superoxide dismutase 3 (SOD3);
−1296TT within the promoter of the gene encoding tissue inhibitor of metalloproteinase 3 (TIMP3);
CC (homozygous P allele) within codon 10 of the gene encoding transforming growth factor beta (TGFβ); and
2G2G within the promoter of the gene encoding metalloproteinase 1 (MMP1).

7. The method according to claim 6, wherein all polymorphisms of the group are analysed.

8. The method according to claim 1, wherein when the disease is a lung disease, the susceptibility polymorphism analysed is selected from one or more of the group consisting of:

−82AA within the promoter of the gene encoding human macrophage elastase (MMP12);
−1562CT or −1562TT within the promoter of the gene encoding metalloproteinase 9 (MMP9); and
1237AG or 1237AA (Tt or tt allele genotypes) within the 3' region of the gene encoding α1-antitrypsin (α1AT).

9. The method according to claim 8, wherein all polymorphisms of the group are analysed.

10. The method according claim 1, wherein when the disease is COPD, the protective polymorphism analysed is selected from one or more of the group consisting of:

−765 CC or CG in the promoter of the gene encoding cyclooxygenase 2 (COX2);
Arg 130 Gln AA in the gene encoding Interleukin-13 (IL-13);
Asp 298 Glu TT in the gene encoding nitric oxide synthase 3 (NOS3);
Lys 420 Thr AA or AC in the gene encoding vitamin binding protein (VDBP);
Glu 416 Asp TT or TG in the gene encoding VDBP;
Ile 105 Val AA in the gene encoding glutathione S-transferase (GSTP1);
MS in the gene encoding α1-antitrypsin (α1AT);
+489 GG genotype in the gene encoding Tumor Necrosis factor α(TNFα);
−308 GG genotype in the gene encoding TNFα;
C89Y AA or AG genotype in the gene encoding SMAD3;

161 GG genotype in the gene genotype Mannose binding lectin 2 (MBL2);
−1903 AA genotype in the gene encoding Chymase 1 (CMA1);
Arg 197 Gln AA genotype in the gene encoding N-Acetyl transferase 2 (NAT2);
His 139 Arg GG genotype in the gene encoding Microsomal epoxide hydrolase (MEH);
−366 AA or AG genotype in the gene encoding 5 Lipo-oxygenase (ALOX5);
HOM T2437C TT genotype in the gene encoding Heat Shock Protein 70 (HSP 70);
exon 1 +49 CT or TT genotype in the gene encoding Elafin;
Gln 27 Glu GG genotype in the gene encoding β2 Adrenergic receptor (ADBR); and
−1607 1G1G or 1G2G genotype in the promoter of the gene encoding Matrix Metalloproteinase 1 (MMP1).

11. The method according to claim 10, wherein all polymorphisms of the group are analysed.

12. The method according to claim 1, wherein when the disease is COPD, the susceptibility polymorphism analysed is selected from one or more of the group consisting of:
Arg 16 Gly GG in the gene encoding β2-adrenoreceptor (ADRB2);
105 AA in the gene encoding Interleukin-18 (IL-18);
−133 CC in the promoter of the gene encoding IL-18;
−675 5G5G in the promoter of the gene encoding plasminogen activator inhibitor 1 (PAI-1);
−1055 TT in the promoter of the gene encoding IL-13;
874 TT in the gene encoding interferon gamma (IFNγ);
+489 AA or AG genotype in the gene encoding TNFα;
−308 AA or AG genotype in the gene encoding TNFα;
C89Y GG genotype in the gene encoding SMAD3;
E469K GG genotype in the gene encoding Intracellular Adhesion molecule 1 (ICAM1);
Gly 881 Arg GC or CC genotype in the gene encoding Caspase (NOD2);
−511 GG genotype in the gene encoding IL1B;
Tyr 113 His TT genotype in the gene encoding MEH;
−366 GG genotype in the gene encoding ALOX5;
HOM T2437C CC or CT genotype in the gene encoding HSP 70;
+13924 AA genotype in the gene encoding Chloride Channel Calcium-activated 1 (CLCA1); and
−159 CC genotype in the gene encoding Monocyte differentiation antigen CD-14 (CD-14).

13. The method according to claim 12, wherein all polymorphisms of the group are analysed.

14. The method according to claim 1, wherein when the disease is OCOPD, the protective polymorphism analysed is selected from one or more of the group consisting of:
−765 CC or CG in the promoter of the gene encoding COX2;
−251 AA in the promoter of the gene encoding interleukin-8 (IL-8);
Lys 420 Thr AA in the gene encoding VDBP;
Glu 416 Asp TT or TG in the gene encoding VDBP;
exon 3 T/C RR in the gene encoding microsomal epoxide hydrolase (MEH);
Arg 312 Gln AG or GG in the gene encoding SOD3;
MS or SS in the gene encoding α1AT;
Asp 299 Gly AG or GG in the gene encoding toll-like receptor 4 (TLR4);
Gln 27 Glu CC in the gene encoding ADRB2;
−518 AA in the gene encoding IL-11; and
Asp 298 Glu TT in the gene encoding NOS3.

15. The method according to claim 14, wherein all polymorphisms of the group are analysed.

16. The method according to claim 1, wherein when the disease is OCOPD, the susceptibility polymorphism analysed is selected from one or more of the group consisting of:
−765 GG in the promoter of the gene encoding COX2;
105 AA in the gene encoding IL-18;
−133 CC in the promoter of the gene encoding IL-18;
−675 5G5G in the promoter of the gene encoding PAI-1;
Lys 420 Thr CC in the gene encoding VDBP;
Glu 416 Asp GG in the gene encoding VDBP;
Ile 105 Val GG in the gene encoding GSTP1;
Arg 312 Gln AA in the gene encoding SOD3;
−1055TT in the promoter of the gene encoding IL-13;
3' 1237 Tt or tt in the gene encoding α1AT; and
−1607 2G2G in the promoter of the gene encoding MMP1.

17. The method according to claim 16, wherein all polymorphisms of the group are analysed.

18. The method according to claim 1, wherein when the disease is lung cancer, the protective polymorphism analysed is selected from one or more of the group consisting of:
Asp 298 Glu TT genotype in the gene encoding NOS3;
Arg 312 Gln CG or GG genotype in the gene encoding SOD3;
Asn 357 Ser AG or GG genotype in the gene encoding MMP12;
105 AC or CC genotype in the gene encoding IL-18;
−133 CG or GG genotype in the gene encoding IL-18;
−765 CC or CG genotype in the promoter of the gene encoding COX2;
−221 TT genotype in the gene encoding Mucin 5AC (MUC5AC);
intron 1 C/T TT genotype in the gene encoding Arginase 1 (Arg1);
Leu252Val GG genotype in the gene encoding Insulin-like growth factor II receptor (IGF2R);
−1082GG genotype in the gene encoding Interleukin 10 (IL-10);
−251AA genotype in the gene encoding Interleukin 8 (IL-8);
Arg 399 Gln AA genotype in the X-ray repair complementing defective in Chinese hamster 1 (XRCC1) gene;
A870G GG genotype in the gene encoding cyclin D (CCND1);
−751 GG genotype in the promoter of the xeroderma pigmentosum complementation group D (XPD) gene ;
Ile 462 Val AG or GG genotype in the gene encoding cytochrome P450 1A1 (CYP1A1);
Ser 326 Cys GG genotype in the gene encoding 8-Oxoguanine DNA glycolase (OGG1); and
Phe 257 Ser CC genotype in the gene encoding REV1.

19. The method according to claim 18, wherein all polymorphisms of the group are analysed.

20. The method according claim 1, wherein when the disease is lung cancer, the susceptibility polymorphisms analysed are selected from one or more of the group consisting of:
−786 TT genotype in the promoter of the gene encoding NOS3;
Ala 15 Thr GG genotype in the gene encoding anti-chymotrypsin (ACT);
105 AA genotype in the gene encoding IL-18;
−133 CC genotype in the promoter of the gene encoding IL-18;
874 AA genotype in the gene encoding IFNγ;
−765 GG genotype in the promoter of the gene encoding COX2;

-447 CC or GC genotype in the gene encoding Connective tissue growth factor (CTGF); and
+161 AA or AG genotype in the gene encoding MBL2;
-511 GG genotype in the gene encoding IL-1B;
A-670G AA genotype in the gene encoding FAS (Apo-1/CD95);
Arg 197 Gln GG genotype in the gene encoding N-acetyltransferase 2 (NAT2);
Ile462 Val AA genotype in the gene encoding CYP1A1;
1019 G/C Pst I CC or CG genotype in the gene encoding cytochrome P450 2E1 (CYP2E1);
C/T Rsa I TT or TC genotype in the gene encoding CYP2E1;
GSTM null genotype in the gene encoding GSTM;
-1607 2G/2G genotype in the promoter of the gene encoding MMP1;
Gln 185 Glu CC genotype in the gene encoding Nibrin (NBS1); and
Asp 148 Glu GG genotype in the gene encoding Apex nuclease (APE1).

21. The method according to claim 18, wherein all polymorphisms of the group are analysed.

22. The method according to claim 1, wherein each protective polymorphism is assigned a value of −1 and each susceptibility polymorphism is assigned a value of +1.

23. The method according to claim 1, wherein each protective polymorphism is assigned a value of +1 and each susceptibility polymorphism is assigned a value of −1.

24. The method according to claim 1, wherein the subject is or has been a smoker.

25. The method according to claim 1, wherein the method comprises an analysis of one or more risk factors, including one or more epidemiological risk factors, associated with the risk of developing said disease.

26. A method of determining a human subject's risk of developing a disease having a genetic basis, said method comprising:
obtaining a sample from a human subject;
obtaining a result of one or more analyses of said sample to determine a presence or absence of at least one protective polymorphism and a presence or absence of at least one susceptibility polymorphism, and wherein said protective and susceptibility polymorphisms are associated with said disease having a genetic basis, and wherein the total number of susceptibility and protective polymorphisms analyzed is four or greater;
assigning a positive score for each protective polymorphism and a negative score for each susceptibility polymorphism or vice versa; and
calculating a net score for said subject, said net score representing a balance between a combined value of the at least one protective polymorphism and a combined value of the at least one susceptibility polymorphism present in the subject sample,
wherein the disease is selected from the group consisting of lung cancer, chronic obstructive pulmonary disease (COPD), occupational chronic obstructive pulmonary disease (OCOPD), and emphysema, and wherein a net protective score is predictive of a reduced risk of developing said disease and a net susceptibility score is predictive of an increased risk of developing said disease.

27. A method of assessing a human subject's risk of developing a disease having a genetic basis, comprising:
obtaining a biological sample from a human subject;
analyzing said sample for a presence or absence of at least one protective polymorphism and for a presence or absence of at least one susceptibility polymorphism, wherein said at least one protective polymorphism and said at least one susceptibility polymorphism are associated with a disease having a genetic basis, and wherein the total number of susceptibility and protective polymorphisms analyzed is five or greater;
assigning a positive score for each protective polymorphism and a negative score for each susceptibility polymorphism or vice versa; and
calculating a net score for said subject, said net score representing a balance between a combined value of the at least one protective polymorphism and the combined value of the at least one susceptibility polymorphism present in the subject sample;
wherein the disease is selected from the group consisting of lung cancer, chronic obstructive pulmonary disease (COPD), occupational chronic obstructive pulmonary disease (OCOPD), and emphysema, and wherein a net protective score is predictive of a reduced risk of developing said disease and a net susceptibility score is predictive of an increased risk of developing said disease.

28. A method of assessing a human subject's risk of developing a disease having a genetic basis, comprising:
obtaining a biological sample from a human subject;
analyzing said sample for a presence or absence of at least one protective polymorphism and for a presence or absence of at least one susceptibility polymorphism, wherein said at least one protective polymorphism and said at least one susceptibility polymorphism are associated with a disease having a genetic basis, and wherein the total number of susceptibility and protective polymorphisms analyzed is six or greater;
assigning a positive score for each protective polymorphism and a negative score for each susceptibility polymorphism or vice versa; and
calculating a net score for said subject, said net score representing a balance between a combined value of the at least one protective polymorphism and the combined value of the at least one susceptibility polymorphism present in the subject sample;
wherein the disease is selected from the group consisting of lung cancer, chronic obstructive pulmonary disease (COPD), occupational chronic obstructive pulmonary disease (OCOPD), and emphysema, and wherein a net protective score is predictive of a reduced risk of developing said disease and a net susceptibility score is predictive of an increased risk of developing said disease.

29. A method of assessing a human subject's risk of developing a disease having a genetic basis, comprising:
obtaining a biological sample from a human subject;
analyzing said sample for a presence or absence of at least one protective polymorphism and for a presence or absence of at least one susceptibility polymorphism, wherein said at least one protective polymorphism and said at least one susceptibility polymorphism are associated with a disease having a genetic basis, and wherein the total number of susceptibility and protective polymorphisms analyzed is seven or greater;
assigning a positive score for each protective polymorphism and a negative score for each susceptibility polymorphism or vice versa; and
calculating a net score for said subject, said net score representing a balance between a combined value of the at least one protective polymorphism and the combined value of the at least one susceptibility polymorphism present in the subject sample;
wherein the disease is selected from the group consisting of lung cancer, chronic obstructive pulmonary disease (COPD), occupational chronic obstructive pulmonary disease (OCOPD), and emphysema, and wherein a net protective score is predictive of a reduced risk of developing said disease and a net susceptibility score is predictive of an increased risk of developing said disease.

30. The method of claim 1, wherein the value assigned to one of the susceptibility and protective polymorphisms analysed is weighted.

31. The method of claim 27, wherein the value assigned to one of the susceptibility and protective polymorphisms analysed is weighted.

32. The method of claim 28, wherein the value assigned to one of the susceptibility and protective polymorphisms analysed is weighted.

33. The method of claim 29, wherein the value assigned to one of the susceptibility and protective polymorphisms analysed is weighted.

* * * * *